(12) United States Patent
Malley et al.

(10) Patent No.: US 10,611,805 B2
(45) Date of Patent: Apr. 7, 2020

(54) MODIFIED BIOTIN-BINDING PROTEIN, FUSION PROTEINS THEREOF AND APPLICATIONS

(71) Applicant: CHILDREN'S MEDICAL CENTER CORPORATION, Boston, MA (US)

(72) Inventors: Richard Malley, Beverly, MA (US); Yingjie Lu, West Roxbury, MA (US); Fan Zhang, West Roxbury, MA (US)

(73) Assignee: CHILDREN'S MEDICAL CENTER CORPORATION, Boston, MA (US)

( * ) Notice: Subject to any disclaimer, the term of this patent is extended or adjusted under 35 U.S.C. 154(b) by 0 days.

(21) Appl. No.: 15/992,343

(22) Filed: May 30, 2018

(65) Prior Publication Data

US 2019/0119335 A1   Apr. 25, 2019

Related U.S. Application Data

(60) Continuation of application No. 14/946,372, filed on Nov. 19, 2015, now Pat. No. 10,017,548, which is a division of application No. 14/116,492, filed as application No. PCT/US2012/037541 on May 11, 2012, now Pat. No. 9,499,593.

(60) Provisional application No. 61/609,974, filed on Mar. 13, 2012, provisional application No. 61/608,168, filed on Mar. 8, 2012, provisional application No. 61/484,934, filed on May 11, 2011.

(51) Int. Cl.
| | |
|---|---|
| C07H 21/04 | (2006.01) |
| C07K 14/31 | (2006.01) |
| A61K 39/09 | (2006.01) |
| A61K 39/385 | (2006.01) |
| A61K 47/54 | (2017.01) |
| A61K 47/61 | (2017.01) |
| A61P 31/04 | (2006.01) |
| A61K 39/00 | (2006.01) |

(52) U.S. Cl.
CPC ............ *C07K 14/31* (2013.01); *A61K 39/092* (2013.01); *A61K 39/385* (2013.01); *A61K 47/543* (2017.08); *A61K 47/557* (2017.08); *A61K 47/61* (2017.08); *A61P 31/04* (2018.01); *A61K 2039/55505* (2013.01); *A61K 2039/6031* (2013.01); *A61K 2039/6093* (2013.01); *A61K 2039/625* (2013.01); *A61K 2039/627* (2013.01); *A61K 2039/645* (2013.01); *A61K 2039/70* (2013.01); *C07K 2319/00* (2013.01); *C07K 2319/20* (2013.01); *Y02A 50/484* (2018.01)

(58) Field of Classification Search
CPC ...................................................... C07K 14/31
See application file for complete search history.

(56) References Cited

U.S. PATENT DOCUMENTS

| | | | |
|---|---|---|---|
| 6,287,568 | B1 | 9/2001 | Wang |
| 9,499,593 | B2 | 11/2016 | Malley |
| 10,017,548 | B2 | 7/2018 | Malley et al. |
| 2006/0251675 | A1 | 11/2006 | Hagen |
| 2007/0128183 | A1 | 6/2007 | Meinke |
| 2008/0032340 | A1 | 2/2008 | Ghosh |
| 2008/0112964 | A1 | 5/2008 | Kirkham |
| 2009/0054251 | A1 | 2/2009 | O'Connor |
| 2009/0148894 | A1 | 6/2009 | Broedel |
| 2009/0148897 | A1 | 6/2009 | Dai |
| 2010/0003266 | A1 | 1/2010 | Simon |
| 2010/0020945 | A1 | 1/2010 | Li |
| 2010/0022401 | A1 | 1/2010 | Norlund |
| 2010/0166802 | A1 | 7/2010 | Caplan |
| 2010/0209450 | A1 | 8/2010 | Biemans |
| 2013/0115230 | A1 | 5/2013 | Simon |
| 2014/0154286 | A1 | 6/2014 | Malley et al. |
| 2014/0154287 | A1 | 6/2014 | Malley et al. |
| 2015/0374811 | A1 | 12/2015 | Malley |
| 2016/0090404 | A1 | 3/2016 | Malley et al. |
| 2019/0119335 | A1 | 4/2019 | Malley et al. |

FOREIGN PATENT DOCUMENTS

| | | |
|---|---|---|
| EP | 1838345 B1 | 12/2010 |
| JP | H11502820 A | 3/1999 |
| JP | 2002504096 A | 2/2002 |
| JP | 2007504237 A | 3/2007 |
| JP | 2008509682 A5 | 9/2009 |
| JP | 2010517532 A | 5/2010 |
| JP | 2014517835 A | 7/2014 |
| RU | 2164943 C2 | 4/2001 |

(Continued)

OTHER PUBLICATIONS

Colino et al, "Parameters Underlying Distinct T Cell-Dependent Polysaccharide-Specific IgG Responses to an Intact Gram-Positive Bacterium versus a Soluble Conjugate Vaccine" Journal of Immunology 183:1551-1559 (2009).

(Continued)

*Primary Examiner* — Albert M Navarro
(74) *Attorney, Agent, or Firm* — Nixon Peabody, LLP; David S. Resnick; Susanna C. Benn

(57) ABSTRACT

The disclosure provides modified biotin-binding proteins which can be expressed in soluble form in high yield in bacteria. Also provided are fusion proteins comprising the modified biotin-binding protein and an antigen. The disclosure further provides non-hemolytic variants of alpha-hemolysin from *S. aureus* and fusion protein comprising non-hemolytic variant of alpha-hemolysin and a biotin-binding domains. Immunogenic compositions comprising the proteins are also disclosed and use of such immunogenic compositions for inducing an immune response or for vaccinating a subject are also disclosed.

14 Claims, 11 Drawing Sheets

Specification includes a Sequence Listing.

(56) References Cited

FOREIGN PATENT DOCUMENTS

| | | |
|---|---|---|
| RU | 2006117425 A | 12/2007 |
| RU | 2378008 C2 | 1/2010 |
| RU | 2407749 C2 | 12/2010 |
| WO | 1996029094 A1 | 9/1996 |
| WO | 1998047530 A2 | 10/1998 |
| WO | 2003094960 A2 | 11/2003 |
| WO | 2005037190 A2 | 4/2005 |
| WO | 2005039501 A2 | 5/2005 |
| WO | 2006017929 A1 | 2/2006 |
| WO | 2006067632 A2 | 6/2006 |
| WO | 2007026249 A2 | 3/2007 |
| WO | 2007081583 A2 | 7/2007 |
| WO | 2007150020 A1 | 12/2007 |
| WO | 2008094986 A2 | 8/2008 |
| WO | 2008152448 A2 | 12/2008 |
| WO | 2009021548 A1 | 2/2009 |
| WO | 2009029831 A1 | 3/2009 |
| WO | 2010053559 A1 | 5/2010 |
| WO | 2010071986 A1 | 7/2010 |
| WO | 2011008548 A1 | 1/2011 |
| WO | 2012155007 A1 | 11/2012 |
| WO | 2012155053 A1 | 11/2012 |

OTHER PUBLICATIONS

International Search Report for PCT/US2012/037412 (Multiple Antigen Presenting Immunogenic Composition, and Methods and Uses Thereof, filed May 11, 2012), issued by ISA/FIPS, 3 pages (dated Aug. 23, 2012).

International Search Report for PCT/US2012/037541 (Modified Biotin-Binding Protein, Fusion Proteins Thereof and Applications, filed May 11, 2012), issued by ISA/FIPS, 4 pages (dated Aug. 30, 2012).

Written Opinion for PCT/US2012/037412 (Multiple Antigen Presenting Immunogenic Composition, and Methods and Uses Thereof, filed May 11, 2012), issued by ISA/FIPS, 4 pages (dated Aug. 23, 2012).

Written Opinion for PCT/US2012/037541 (Modified Biotin-Binding Protein, Fusion Proteins Thereof and Applications, filed May 11, 2012), issued by ISA/FIPS, 3 pages. (dated Aug. 30, 2012).

AVCI et al., "A mechanism for glycoconjugate vaccine activation of the adaptive immune system and its implications for vaccine design", Nat Med 17(12) 1602-1609 (2011).

Colino et al., "Noncovalent association of protein and capsular polysaccharide on bacteria-sized latex beads as a model for polysaccharide-specific humoral immunity to intact gram-positive extracellular bacteria", J Immunol 191(6) 3254-3263 (2013).

Cortajarena et al., "A receptor-binding region in Escherichia coli alpha-haemolysin", J Biol Chem 278(21) 19159-19163 (2003).

Dagan et al., "Glycoconjugate vaccines and immune interference: A review", Vaccine 28(34) 5513-5523 (2010).

Database, UniProt KB/TrEMBL, B3Q265_RHIE6, Sep. 2, 2008.
Database, UniProt KB/TrEMBL, F2AA21_RHIET, May 31, 2011.
Database, UniProt KB/TrEMBL, Q8KKW2_RHIEC, Oct. 1, 2002.

Elgert, "Immunology: understanding the immune system ", John Wiley & Sons p. 111 (2009).

EP Communication dated Apr. 9, 2015 corresponding to EP Application No. 1278163631.

Fauvart et al., "Genome sequence of Rhizobium etli CNPAF512, a nitrogen-fixing symbiont isolated from bean root nodules in Brazil", J Bacteriol 193(12) 3158-3159 (2011).

Gaj et al., "The AviD-tag, a NeutrAvidin/avidin specific peptide affinity tag for the immobilization and purification of recombinant proteins", Protein Exp Purif 56(1) 54-61 (2007).

Gonzalez et al., "The mosaic structure of the symbiotic plasmid of Rhizobium etli CFN42 and its relation to other symbiotic genome compartments", Genome Biol 4(6) R36 (2003).

Grun et al., "One-step biotinylation procedure for carbohydrates to study carbohydrate-protein interactions", Anal Biochem 352(1) 54-63 (2006).

Helppolainen et al., "Bradavidin II from Bradyrhizobium japonicum: a new avidin-like biotin-binding protein", Biochim Biophys Acta 1784(7-8) 1002-1010 (2008).

Helppolanien et al., "Rhizavidin from Rhizobium etli: the first natural dimer in the avidin protein family", Biochem 405(3) 397-405 (2007).

Hermanson, Bioconjugate Tequniques, Elsevier Science, ProQuest Ebook Central, http://ebookcentral.proquest.com/lib.uspto-ebooks/details.action?docID=307203. Created from uspto-ebooks on Sep. 6, 2017, pp. 570-592 (1996).

Hsu et al., "Profiling carbohydrate-receptor interaction with recombinant innate immunity receptor-Fc fusion proteins", J Biol Chem 284(50) 34479-34489 (2009).

Huang et al., "Robust stimulation of humoral and cellular immune responses following vaccination with antigen-loaded beta-glucan particles", MBio 1(3) e00164-10 (2010).

Hytonen et al., "Efficient production of active chicken avidin using a bacterial signal peptide in Escherichia coli", Biochem J 384(Pt 2) 385-390 (2004).

Insel et al., "Response to oligosaccharide-protein conjugate vaccine against Hemophilus influenzae b in two patients with IgG2 deficiency unresponsive to capsular polysaccharide vaccine", N Engl J Med 315(8) 499-503 (1986).

Izard et al., "Signal peptides: exquisitely designed transport promoters", Mol Microbiol 13(5) 765-773 (1994).

Jin et al., "Conjugates of group A and W135 capsular polysaccharides of neisseria meningitidis bound to recombinant Staphylococcus aureusenterotoxin C1: preparation, physicochemical characterization, and immunological properties in mice", Infect Immun 73(12) 7887-7893 (2005).

Lees et al., "Enhanced immunogenicity of protein-dextran conjugates: I. Rapid stimulation of enhanced antibody responses to poorly immunogenic molecules", Vaccine 12(13) 1160-1166 (1994).

Pollabauer et al., "The influence of carrier protein on the immunogenicity of simultaneously administered conjugate vaccines in infants", Vaccine 27(11) 1674-1679 (2009).

Rosenberg, Protein Analysis and Purification, Springer Science+Business Media, New York, pp. 153-182 (1996).

Sanabria-Valentin et al., "Lipopolysaccharide modification strategies of Helicobacter pylori during persistent colonization", Dissertation, Department of Basic Medical Science, New York University, 2008.

Sano et al., In Methods in Enzymology vol. 326, pp. 305-307 (2000).

Scott et al., Immunogenicity of biotinylated hapten-avidin complexes, Mol Immunol 21(11) 1055-1060 (1984).

Sen et al., "In vivo humoral immune responses to isolated pneumococcal polysaccharides are dependent on the presence of associated TLR ligands", J Immunol 175(5) 3084-3091 (2005).

Takakura et al., "Tamavidin, a versatile affinity tag for protein purification and immobilization", J Biotechnol 145(4) 317-322 (2010).

Thermo Scientific Avidin-Biotin Technical Handbook, 2009, p. 16-17. Found on the Internet on May 5, 2016 at:https://www.thermofisher.com/content/dam/LifeTech/Images/integration/1601675_AvBi_HB_INTL.pdf.

Wardenburg et al., "Vaccine protection against Staphylococcus aureus pneumonia", J Exp Med 205(2) 287-294 (2008).

Zhang et al., "Multiple antigen-presenting system (MAPS) to induce comprehensive B- and T-cell immunity", Proc Natl Acad Sci USA 110(33) 13564-13569 (2013).

THE CONSTRUCT

MKKIWLALAGLVLAFSASAAQDP | Rhavi (45-179) | GGGGSSSVDKLAAALEHHHHHH

↑
SECRETION SIGNAL SEQUENCE

THE SPECIFIC MODIFICATIONS

- REMOVE THE FIRST 44 AMINO ACID RESIDUES OF FULL LENGTH RHIZAVIDIN
- ADD E coli SECRETION SIGNAL SEQUENCE (IN DASHED FRAME OF THE ABOVE CONSTRUCT) TO THE N-TERMINI OF Rhavi (45-179)
- SYNTHESIZE DNA SEQUENCE THAT ENCODES Rhavi (45-179) USING E coli OPTIMIZED EXPRESSION CODON

*FIG. 1*

SDS-PAGE OF PURIFIED RECOMBINANT RHIZAVIDIN (45-179)

*FIG. 2*

| MKKIWLALAGLVLAFSASA | AQDP | Rhavi (45-179) | GGGGSSS | Antigen X | LEHHHHHH |

1. rhavi-Pdt
2. rhavi-PsaA
3. rhavi-sp1733
4. rhavi-sp1534
5. rhavi-sp0435
6. rhavi-sp1458
7. rhavi-ESAT-6/Cfp10
8. rhavi-TB9.8/TB10.4
9. rhavi-MPT64
10. rhavi-MPT83

SDS-PAGE OF PURIFIED RHIZAVIDIN FUSION PROTEINS

THE CONSTRUCT

MKKVAAFVALSLLMAGCVSDP | Rhavi (45-179) | GGGGSSSVDKLAAALEHHHHHH

↑
SECRETION SEQUENCE/LIPIDATION BOX

THE SPECIFIC MODIFICATIONS

- REMOVE THE FIRST 44 AMINO ACID RESIDUES OF FULL LENGTH RHIZAVIDIN
- ADD E coli SIGNAL SEQUENCE/LIPIDATION BOX (IN DASHED FRAME OF THE ABOVE CONSTRUCT) TO THE N-TERMINI OF Rhavi (45-179)
- SYNTHESIZE DNA SEQUENCE THAT ENCODES Rhavi (45-179) USING E coli OPTIMIZED EXPRESSION CODON

*FIG. 5*

SDS-PAGE OF PURIFIED LIPIDATED RHIZAVIDIN

*FIG. 6*

THE CONSTRUCTS

1) Hla (WT/MUTANT)

M | Hla (27-319) | LEHHHHHH

2) Rhizavidin-Hla (WT/MUTANT) FUSION PROTEIN

MKKIWLALAGLVLAFSASAAQDP | rhizavidin (45-179) | GGGGSSS | Hla (27-319) | LEHHHHHH POINT MUTATIONS MADE ON Hla

- RESIDUE 205 W TO A
- RESIDUE 209-211: DRD TO AAA
- RESIDUE 213 W TO A

SDDS-PAGE OF PURIFIED WT Hla OR MUTANTS

SADS-PAGE OF PURIFIED RHIZAVIDIN FUSION PROTEINS OF WT OR MUTANT Hla

HEMOLYTIC ACTIVITY OF WT OR MUTANT Hla AND THEIR RHIZAVIDIN FUSION PROTEINS

INCORPORATION OF LIPIDATED RHIZAVIDIN OR Rhavi-Hla209 INTO MAPS COMPLEX ENHANCES T CELL RESPONSES TO OTHER ANTIGENS

FIG. 14

```
                              SEQUENCE LISTING

<160> NUMBER OF SEQ ID NOS: 58

<210> SEQ ID NO 1
<211> LENGTH: 135
<212> TYPE: PRT
<213> ORGANISM: Rhizobium sp.

<400> SEQUENCE: 1

Phe Asp Ala Ser Asn Phe Lys Asp Phe Ser Ser Ile Ala Ser Ala Ser
1               5                   10                  15

Ser Ser Trp Gln Asn Gln Ser Gly Ser Thr Met Ile Ile Gln Val Asp
            20                  25                  30

Ser Phe Gly Asn Val Ser Gly Gln Tyr Val Asn Arg Ala Gln Gly Thr
        35                  40                  45

Gly Cys Gln Asn Ser Pro Tyr Pro Leu Thr Gly Arg Val Asn Gly Thr
    50                  55                  60

Phe Ile Ala Phe Ser Val Gly Trp Asn Asn Ser Thr Glu Asn Cys Asn
65                  70                  75                  80

Ser Ala Thr Gly Trp Thr Gly Tyr Ala Gln Val Asn Gly Asn Asn Thr
                85                  90                  95

Glu Ile Val Thr Ser Trp Asn Leu Ala Tyr Glu Gly Gly Ser Gly Pro
            100                 105                 110

Ala Ile Glu Gln Gly Gln Asp Thr Phe Gln Tyr Val Pro Thr Thr Glu
        115                 120                 125

Asn Lys Ser Leu Leu Lys Asp
    130                 135

<210> SEQ ID NO 2
<211> LENGTH: 19
<212> TYPE: PRT
<213> ORGANISM: Escherichia coli

<400> SEQUENCE: 2

Met Lys Lys Ile Trp Leu Ala Leu Ala Gly Leu Val Leu Ala Phe Ser
1               5                   10                  15

Ala Ser Ala

<210> SEQ ID NO 3
<211> LENGTH: 17
<212> TYPE: PRT
<213> ORGANISM: Escherichia coli

<400> SEQUENCE: 3

Met Lys Lys Val Ala Ala Phe Val Ala Leu Ser Leu Leu Met Ala Gly
1               5                   10                  15

Cys

<210> SEQ ID NO 4
<211> LENGTH: 179
<212> TYPE: PRT
<213> ORGANISM: Rhizobium sp.

<400> SEQUENCE: 4

Met Ile Ile Thr Ser Leu Tyr Ala Thr Phe Gly Thr Ile Ala Asp Gly
```

```
                1               5                   10                  15
        Arg Arg Thr Ser Gly Gly Lys Thr Met Ile Arg Thr Asn Ala Val Ala
                        20                  25                  30

Ala Leu Val Phe Ala Val Ala Thr Ser Ala Leu Ala Phe Asp Ala Ser
                        35                  40                  45

Asn Phe Lys Asp Phe Ser Ser Ile Ala Ser Ala Ser Ser Ser Trp Gln
                        50                  55                  60

Asn Gln Ser Gly Ser Thr Met Ile Ile Gln Val Asp Ser Phe Gly Asn
         65                 70                  75                  80

Val Ser Gly Gln Tyr Val Asn Arg Ala Gln Gly Thr Gly Cys Gln Asn
                        85                  90                  95

Ser Pro Tyr Pro Leu Thr Gly Arg Val Asn Gly Thr Phe Ile Ala Phe
                        100                 105                 110

Ser Val Gly Trp Asn Asn Ser Thr Glu Asn Cys Asn Ser Ala Thr Gly
                        115                 120                 125

Trp Thr Gly Tyr Ala Gln Val Asn Gly Asn Asn Thr Glu Ile Val Thr
                        130                 135                 140

Ser Trp Asn Leu Ala Tyr Glu Gly Gly Ser Gly Pro Ala Ile Glu Gln
         145                150                 155                 160

Gly Gln Asp Thr Phe Gln Tyr Val Pro Thr Thr Glu Asn Lys Ser Leu
                        165                 170                 175

Leu Lys Asp

<210> SEQ ID NO 5
<211> LENGTH: 44
<212> TYPE: PRT
<213> ORGANISM: Rhizobium sp.

<400> SEQUENCE: 5

Met Ile Ile Thr Ser Leu Tyr Ala Thr Phe Gly Thr Ile Ala Asp Gly
 1               5                   10                  15

Arg Arg Thr Ser Gly Gly Lys Thr Met Ile Arg Thr Asn Ala Val Ala
                20                  25                  30

Ala Leu Val Phe Ala Val Ala Thr Ser Ala Leu Ala
                35                  40

<210> SEQ ID NO 6
<211> LENGTH: 20
<212> TYPE: PRT
<213> ORGANISM: Rhizobium sp.

<400> SEQUENCE: 6

Met Ile Arg Thr Asn Ala Val Ala Ala Leu Val Phe Ala Val Ala Thr
 1               5                   10                  15

Ser Ala Leu Ala
                20

<210> SEQ ID NO 7
<211> LENGTH: 23
<212> TYPE: PRT
<213> ORGANISM: Unknown
<220> FEATURE:
<223> OTHER INFORMATION: Description of Unknown: Signal
      peptide

<400> SEQUENCE: 7

Met Ala Pro Phe Glu Pro Leu Ala Ser Gly Ile Leu Leu Leu Leu Trp
 1               5                   10                  15
```

Leu Ile Ala Pro Ser Arg Ala
            20

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Gln Asp Pro
1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val Ser Asp Pro
1

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 10

His His His His His His
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Asp Lys Leu Ala Ala Ala Leu Glu
1               5

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Gly Gly Ser Ser Ser Val Asp Lys Leu Ala Ala Ala Leu Glu
1               5                   10                  15

<210> SEQ ID NO 13
<211> LENGTH: 14
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 13

Val Asp Lys Leu Ala Ala Ala Leu Glu His His His His
1               5                   10

<210> SEQ ID NO 14
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Gly Gly Gly Ser Ser Ser Val Asp Lys Leu Ala Ala Ala Leu Glu
1               5                   10                  15

His His His His His His
            20

<210> SEQ ID NO 15
<211> LENGTH: 180
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Lys Lys Ile Trp Leu Ala Leu Ala Gly Leu Val Leu Ala Phe Ser
1               5                   10                  15

Ala Ser Ala Ala Gln Asp Pro Phe Asp Ala Ser Asn Phe Lys Asp Phe
                20                  25                  30

Ser Ser Ile Ala Ser Ala Ser Ser Trp Gln Asn Gln Ser Gly Ser
            35                  40                  45

Thr Met Ile Ile Gln Val Asp Ser Phe Gly Asn Val Ser Gly Gln Tyr
    50                  55                  60

Val Asn Arg Ala Gln Gly Thr Gly Cys Gln Asn Ser Pro Tyr Pro Leu
65                  70                  75                  80

Thr Gly Arg Val Asn Gly Thr Phe Ile Ala Phe Ser Val Gly Trp Asn
                85                  90                  95

Asn Ser Thr Glu Asn Cys Asn Ser Ala Thr Gly Trp Thr Gly Tyr Ala
            100                 105                 110

Gln Val Asn Gly Asn Asn Thr Glu Ile Val Thr Ser Trp Asn Leu Ala
        115                 120                 125

Tyr Glu Gly Gly Ser Gly Pro Ala Ile Glu Gln Gly Gln Asp Thr Phe
    130                 135                 140

Gln Tyr Val Pro Thr Thr Glu Asn Lys Ser Leu Leu Lys Asp Gly Gly
145                 150                 155                 160

Gly Gly Ser Ser Ser Val Asp Lys Leu Ala Ala Ala Leu Glu His His
                165                 170                 175

His His His His
        180

<210> SEQ ID NO 16
<211> LENGTH: 21
<212> TYPE: PRT
<213> ORGANISM: Escherichia coli

<400> SEQUENCE: 16

-continued

Met Asn Ser Lys Lys Leu Cys Cys Ile Cys Val Leu Phe Ser Leu Leu
1               5                   10                  15

Ala Gly Cys Ala Ser
            20

<210> SEQ ID NO 17
<211> LENGTH: 19
<212> TYPE: PRT
<213> ORGANISM: Escherichia coli

<400> SEQUENCE: 17

Met Arg Tyr Ser Lys Leu Thr Met Leu Ile Pro Cys Ala Leu Leu Leu
1               5                   10                  15

Ser Ala Cys

<210> SEQ ID NO 18
<211> LENGTH: 24
<212> TYPE: PRT
<213> ORGANISM: Escherichia coli

<400> SEQUENCE: 18

Met Phe Val Thr Ser Lys Lys Met Thr Ala Ala Val Leu Ala Ile Thr
1               5                   10                  15

Leu Ala Met Ser Leu Ser Ala Cys
            20

<210> SEQ ID NO 19
<211> LENGTH: 18
<212> TYPE: PRT
<213> ORGANISM: Escherichia coli

<400> SEQUENCE: 19

Met Ile Lys Arg Val Leu Val Ser Met Val Gly Leu Ser Leu Val
1               5                   10                  15

Gly Cys

<210> SEQ ID NO 20
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Lys Lys Val Ala Ala Phe Val Ala Leu Ser Leu Met Ala Gly
1               5                   10                  15

Cys Val Ser Asp Pro Phe Asp Ala Ser Asn Phe Lys Asp Phe Ser Ser
                20                  25                  30

Ile Ala Ser Ala Ser Ser Ser Trp Gln Asn Gln Ser Gly Ser Thr Met
            35                  40                  45

Ile Ile Gln Val Asp Ser Phe Gly Asn Val Ser Gly Gln Tyr Val Asn
        50                  55                  60

Arg Ala Gln Gly Thr Gly Cys Gln Asn Ser Pro Tyr Pro Leu Thr Gly
65                  70                  75                  80

Arg Val Asn Gly Thr Phe Ile Ala Phe Ser Val Gly Trp Asn Asn Ser
                85                  90                  95

Thr Glu Asn Cys Asn Ser Ala Thr Gly Trp Thr Gly Tyr Ala Gln Val
            100                 105                 110

Asn Gly Asn Asn Thr Glu Ile Val Thr Ser Trp Asn Leu Ala Tyr Glu
            115                 120                 125

Gly Gly Ser Gly Pro Ala Ile Glu Gln Gly Gln Asp Thr Phe Gln Tyr
    130                 135                 140

Val Pro Thr Thr Glu Asn Lys Ser Leu Leu Lys Asp
145                 150                 155

<210> SEQ ID NO 21
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Lys Lys Ile Trp Leu Ala Leu Ala Gly Leu Val Leu Ala Phe Ser
1               5                   10                  15

Ala Ser Ala Ala Gln Asp Pro Phe Asp Ala Ser Asn Phe Lys Asp Phe
            20                  25                  30

Ser Ser Ile Ala Ser Ala Ser Ser Trp Gln Asn Gln Ser Gly Ser
            35                  40                  45

Thr Met Ile Ile Gln Val Asp Ser Phe Gly Asn Val Ser Gly Gln Tyr
    50                  55                  60

Val Asn Arg Ala Gln Gly Thr Gly Cys Gln Asn Ser Pro Tyr Pro Leu
65                  70                  75                  80

Thr Gly Arg Val Asn Gly Thr Phe Ile Ala Phe Ser Val Gly Trp Asn
                85                  90                  95

Asn Ser Thr Glu Asn Cys Asn Ser Ala Thr Gly Trp Thr Gly Tyr Ala
            100                 105                 110

Gln Val Asn Gly Asn Asn Thr Glu Ile Val Thr Ser Trp Asn Leu Ala
            115                 120                 125

Tyr Glu Gly Gly Ser Gly Pro Ala Ile Glu Gln Gly Gln Asp Thr Phe
    130                 135                 140

Gln Tyr Val Pro Thr Thr Glu Asn Lys Ser Leu Leu Lys Asp Gly Gly
145                 150                 155                 160

Gly Gly Ser Ser Ala Asp Ser Asp Ile Asn Ile Lys Thr Gly Thr
            165                 170                 175

Thr Asp Ile Gly Ser Asn Thr Thr Val Lys Thr Gly Asp Leu Val Thr
            180                 185                 190

Tyr Asp Lys Glu Asn Gly Met His Lys Lys Val Phe Tyr Ser Phe Ile
    195                 200                 205

Asp Asp Lys Asn His Asn Lys Lys Leu Leu Val Ile Arg Thr Lys Gly
210                 215                 220

Thr Ile Ala Gly Gln Tyr Arg Val Tyr Ser Glu Gly Ala Asn Lys
225                 230                 235                 240

Ser Gly Leu Ala Trp Pro Ser Ala Phe Lys Val Gln Leu Gln Leu Pro
                245                 250                 255

Asp Asn Glu Val Ala Gln Ile Ser Asp Tyr Tyr Pro Arg Asn Ser Ile
            260                 265                 270

Asp Thr Lys Glu Tyr Met Ser Thr Leu Thr Tyr Gly Phe Asn Gly Asn
            275                 280                 285

Val Thr Gly Asp Asp Thr Gly Lys Ile Gly Gly Leu Ile Gly Ala Asn
    290                 295                 300

Val Ser Ile Gly His Thr Leu Lys Tyr Val Gln Pro Asp Phe Lys Thr
305                 310                 315                 320

```
Ile Leu Glu Ser Pro Thr Asp Lys Lys Val Gly Trp Lys Val Ile Phe
                325                 330                 335

Asn Asn Met Val Asn Gln Asn Trp Gly Pro Tyr Ala Ala Ser Trp
            340                 345                 350

Asn Pro Val Tyr Gly Asn Gln Leu Phe Met Lys Thr Arg Asn Gly Ser
                355                 360                 365

Met Lys Ala Ala Asp Asn Phe Leu Asp Pro Asn Lys Ala Ser Ser Leu
    370                 375                 380

Leu Ser Ser Gly Phe Ser Pro Asp Phe Ala Thr Val Ile Thr Met Asp
385                 390                 395                 400

Arg Lys Ala Ser Lys Gln Thr Asn Ile Asp Val Ile Tyr Glu Arg
                405                 410                 415

Val Arg Asp Asp Tyr Gln Leu His Trp Thr Ser Thr Asn Trp Lys Gly
                420                 425                 430

Thr Asn Thr Lys Asp Lys Trp Ile Asp Arg Ser Ser Glu Arg Tyr Lys
                435                 440                 445

Ile Asp Trp Glu Lys Glu Glu Met Thr Asn
    450                 455
```

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

```
Gly Gly Gly Gly Ser Ser Ser
1               5
```

<210> SEQ ID NO 23
<211> LENGTH: 293
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140
```

```
Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Ala Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Ile Asp Arg Ser Ser Glu Arg Tyr Lys Ile Asp Trp Glu Lys
        275                 280                 285

Glu Glu Met Thr Asn
    290
```

<210> SEQ ID NO 24
<211> LENGTH: 293
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Ala Asn Pro Val Tyr Gly
            180                 185                 190

Asn Gln Leu Phe Met Lys Thr Arg Asn Gly Ser Met Lys Ala Ala Asp
```

```
            195                 200                 205
Asn Phe Leu Asp Pro Asn Lys Ala Ser Ser Leu Leu Ser Ser Gly Phe
        210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Ile Asp Arg Ser Ser Glu Arg Tyr Lys Ile Asp Trp Glu Lys
        275                 280                 285

Glu Glu Met Thr Asn
        290

<210> SEQ ID NO 25
<211> LENGTH: 293
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Ala Ala Ala Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
        210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255
```

-continued

```
Gln Leu His Trp Thr Ser Thr Asn Trp Lys Gly Thr Asn Thr Lys Asp
            260                 265                 270

Lys Trp Ile Asp Arg Ser Ser Glu Arg Tyr Lys Ile Asp Trp Glu Lys
        275                 280                 285

Glu Glu Met Thr Asn
    290
```

<210> SEQ ID NO 26
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Met Lys Lys Ile Trp Leu Ala Leu Ala Gly Leu Val Leu Ala Phe Ser
1               5                   10                  15

Ala Ser Ala Ala Gln Asp Pro Phe Asp Ala Ser Asn Phe Lys Asp Phe
            20                  25                  30

Ser Ser Ile Ala Ser Ala Ser Ser Trp Gln Asn Gln Ser Gly Ser
        35                  40                  45

Thr Met Ile Ile Gln Val Asp Ser Phe Gly Asn Val Ser Gly Gln Tyr
50                  55                  60

Val Asn Arg Ala Gln Gly Thr Gly Cys Gln Asn Ser Pro Tyr Pro Leu
65                  70                  75                  80

Thr Gly Arg Val Asn Gly Thr Phe Ile Ala Phe Ser Val Gly Trp Asn
            85                  90                  95

Asn Ser Thr Glu Asn Cys Asn Ser Ala Thr Gly Trp Thr Gly Tyr Ala
            100                 105                 110

Gln Val Asn Gly Asn Asn Thr Glu Ile Val Thr Ser Trp Asn Leu Ala
            115                 120                 125

Tyr Glu Gly Gly Ser Gly Pro Ala Ile Glu Gln Gly Gln Asp Thr Phe
        130                 135                 140

Gln Tyr Val Pro Thr Thr Glu Asn Lys Ser Leu Leu Lys Asp Gly Gly
145                 150                 155                 160

Gly Gly Ser Ser Ser Ala Asp Ser Asp Ile Asn Ile Lys Thr Gly Thr
            165                 170                 175

Thr Asp Ile Gly Ser Asn Thr Thr Val Lys Thr Gly Asp Leu Val Thr
            180                 185                 190

Tyr Asp Lys Glu Asn Gly Met His Lys Lys Val Phe Tyr Ser Phe Ile
        195                 200                 205

Asp Asp Lys Asn His Asn Lys Lys Leu Leu Val Ile Arg Thr Lys Gly
    210                 215                 220

Thr Ile Ala Gly Gln Tyr Arg Val Tyr Ser Glu Gly Ala Asn Lys
225                 230                 235                 240

Ser Gly Leu Ala Trp Pro Ser Ala Phe Lys Val Gln Leu Gln Leu Pro
            245                 250                 255

Asp Asn Glu Val Ala Gln Ile Ser Asp Tyr Tyr Pro Arg Asn Ser Ile
            260                 265                 270

Asp Thr Lys Glu Tyr Met Ser Thr Leu Thr Tyr Gly Phe Asn Gly Asn
        275                 280                 285

Val Thr Gly Asp Asp Thr Gly Lys Ile Gly Gly Leu Ile Gly Ala Asn
    290                 295                 300

Val Ser Ile Gly His Thr Leu Lys Tyr Val Gln Pro Asp Phe Lys Thr
305                 310                 315                 320
```

Ile Leu Glu Ser Pro Thr Asp Lys Lys Val Gly Trp Lys Val Ile Phe
                325                 330                 335

Asn Asn Met Val Asn Gln Asn Ala Gly Pro Tyr Asp Arg Asp Ser Trp
            340                 345                 350

Asn Pro Val Tyr Gly Asn Gln Leu Phe Met Lys Thr Arg Asn Gly Ser
        355                 360                 365

Met Lys Ala Ala Asp Asn Phe Leu Asp Pro Asn Lys Ala Ser Ser Leu
    370                 375                 380

Leu Ser Ser Gly Phe Ser Pro Asp Phe Ala Thr Val Ile Thr Met Asp
385                 390                 395                 400

Arg Lys Ala Ser Lys Gln Gln Thr Asn Ile Asp Val Ile Tyr Glu Arg
                405                 410                 415

Val Arg Asp Asp Tyr Gln Leu His Trp Thr Ser Thr Asn Trp Lys Gly
            420                 425                 430

Thr Asn Thr Lys Asp Lys Trp Ile Asp Arg Ser Ser Glu Arg Tyr Lys
        435                 440                 445

Ile Asp Trp Glu Lys Glu Met Thr Asn Val Asp Lys Leu Ala Ala
    450                 455                 460

Ala Leu Glu His His His His His His
465                 470

<210> SEQ ID NO 27
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Lys Lys Ile Trp Leu Ala Leu Ala Gly Leu Val Leu Ala Phe Ser
1               5                   10                  15

Ala Ser Ala Ala Gln Asp Pro Phe Asp Ala Ser Asn Phe Lys Asp Phe
            20                  25                  30

Ser Ser Ile Ala Ser Ala Ser Ser Trp Gln Asn Gln Ser Gly Ser
        35                  40                  45

Thr Met Ile Ile Gln Val Asp Ser Phe Gly Asn Val Ser Gly Gln Tyr
    50                  55                  60

Val Asn Arg Ala Gln Gly Thr Gly Cys Gln Asn Ser Pro Tyr Pro Leu
65                  70                  75                  80

Thr Gly Arg Val Asn Gly Thr Phe Ile Ala Phe Ser Val Gly Trp Asn
                85                  90                  95

Asn Ser Thr Glu Asn Cys Asn Ser Ala Thr Gly Trp Thr Gly Tyr Ala
            100                 105                 110

Gln Val Asn Gly Asn Asn Thr Glu Ile Val Thr Ser Trp Asn Leu Ala
        115                 120                 125

Tyr Glu Gly Gly Ser Gly Pro Ala Ile Glu Gln Gly Gln Asp Thr Phe
    130                 135                 140

Gln Tyr Val Pro Thr Thr Glu Asn Lys Ser Leu Leu Lys Asp Gly Gly
145                 150                 155                 160

Gly Gly Ser Ser Ser Ala Asp Ser Asp Ile Asn Ile Lys Thr Gly Thr
                165                 170                 175

Thr Asp Ile Gly Ser Asn Thr Thr Val Lys Thr Gly Asp Leu Val Thr
            180                 185                 190

Tyr Asp Lys Glu Asn Gly Met His Lys Lys Val Phe Tyr Ser Phe Ile

```
              195                 200                 205
Asp Asp Lys Asn His Asn Lys Lys Leu Leu Val Ile Arg Thr Lys Gly
    210                 215                 220

Thr Ile Ala Gly Gln Tyr Arg Val Tyr Ser Glu Glu Gly Ala Asn Lys
225                 230                 235                 240

Ser Gly Leu Ala Trp Pro Ser Ala Phe Lys Val Gln Leu Gln Leu Pro
                245                 250                 255

Asp Asn Glu Val Ala Gln Ile Ser Asp Tyr Tyr Pro Arg Asn Ser Ile
            260                 265                 270

Asp Thr Lys Glu Tyr Met Ser Thr Leu Thr Tyr Gly Phe Asn Gly Asn
        275                 280                 285

Val Thr Gly Asp Asp Thr Gly Lys Ile Gly Gly Leu Ile Gly Ala Asn
    290                 295                 300

Val Ser Ile Gly His Thr Leu Lys Tyr Val Gln Pro Asp Phe Lys Thr
305                 310                 315                 320

Ile Leu Glu Ser Pro Thr Asp Lys Lys Val Gly Trp Lys Val Ile Phe
                325                 330                 335

Asn Asn Met Val Asn Gln Asn Trp Gly Pro Tyr Asp Arg Asp Ser Ala
            340                 345                 350

Asn Pro Val Tyr Gly Asn Gln Leu Phe Met Lys Thr Arg Asn Gly Ser
        355                 360                 365

Met Lys Ala Ala Asp Asn Phe Leu Asp Pro Asn Lys Ala Ser Ser Leu
    370                 375                 380

Leu Ser Ser Gly Phe Ser Pro Asp Phe Ala Thr Val Ile Thr Met Asp
385                 390                 395                 400

Arg Lys Ala Ser Lys Gln Gln Thr Asn Ile Asp Val Ile Tyr Glu Arg
                405                 410                 415

Val Arg Asp Asp Tyr Gln Leu His Trp Thr Ser Thr Asn Trp Lys Gly
            420                 425                 430

Thr Asn Thr Lys Asp Lys Trp Ile Asp Arg Ser Ser Glu Arg Tyr Lys
        435                 440                 445

Ile Asp Trp Glu Lys Glu Glu Met Thr Asn Val Asp Lys Leu Ala Ala
    450                 455                 460

Ala Leu Glu His His His His His His
465                 470

<210> SEQ ID NO 28
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Lys Lys Ile Trp Leu Ala Leu Ala Gly Leu Val Leu Ala Phe Ser
1               5                   10                  15

Ala Ser Ala Ala Gln Asp Pro Phe Asp Ala Ser Asn Phe Lys Asp Phe
                20                  25                  30

Ser Ser Ile Ala Ser Ala Ser Ser Trp Gln Asn Gln Ser Gly Ser
            35                  40                  45

Thr Met Ile Ile Gln Val Asp Ser Phe Gly Asn Val Ser Gly Gln Tyr
        50                  55                  60

Val Asn Arg Ala Gln Gly Thr Gly Cys Gln Asn Ser Pro Tyr Pro Leu
65                  70                  75                  80
```

-continued

```
Thr Gly Arg Val Asn Gly Thr Phe Ile Ala Phe Ser Val Gly Trp Asn
                 85                  90                  95
Asn Ser Thr Glu Asn Cys Asn Ser Ala Thr Gly Trp Thr Gly Tyr Ala
            100                 105                 110
Gln Val Asn Gly Asn Asn Thr Glu Ile Val Thr Ser Trp Asn Leu Ala
        115                 120                 125
Tyr Glu Gly Gly Ser Gly Pro Ala Ile Glu Gln Gly Gln Asp Thr Phe
    130                 135                 140
Gln Tyr Val Pro Thr Thr Glu Asn Lys Ser Leu Leu Lys Asp Gly Gly
145                 150                 155                 160
Gly Gly Ser Ser Ser Ala Asp Ser Asp Ile Asn Ile Lys Thr Gly Thr
                165                 170                 175
Thr Asp Ile Gly Ser Asn Thr Thr Val Lys Thr Gly Asp Leu Val Thr
            180                 185                 190
Tyr Asp Lys Glu Asn Gly Met His Lys Lys Val Phe Tyr Ser Phe Ile
        195                 200                 205
Asp Asp Lys Asn His Asn Lys Lys Leu Leu Val Ile Arg Thr Lys Gly
    210                 215                 220
Thr Ile Ala Gly Gln Tyr Arg Val Tyr Ser Glu Glu Gly Ala Asn Lys
225                 230                 235                 240
Ser Gly Leu Ala Trp Pro Ser Ala Phe Lys Val Gln Leu Gln Leu Pro
                245                 250                 255
Asp Asn Glu Val Ala Gln Ile Ser Asp Tyr Tyr Pro Arg Asn Ser Ile
            260                 265                 270
Asp Thr Lys Glu Tyr Met Ser Thr Leu Thr Tyr Gly Phe Asn Gly Asn
        275                 280                 285
Val Thr Gly Asp Asp Thr Gly Lys Ile Gly Gly Leu Ile Gly Ala Asn
    290                 295                 300
Val Ser Ile Gly His Thr Leu Lys Tyr Val Gln Pro Asp Phe Lys Thr
305                 310                 315                 320
Ile Leu Glu Ser Pro Thr Asp Lys Lys Val Gly Trp Lys Val Ile Phe
                325                 330                 335
Asn Asn Met Val Asn Gln Asn Trp Gly Pro Tyr Ala Ala Ala Ser Trp
            340                 345                 350
Asn Pro Val Tyr Gly Asn Gln Leu Phe Met Lys Thr Arg Asn Gly Ser
        355                 360                 365
Met Lys Ala Ala Asp Asn Phe Leu Asp Pro Asn Lys Ala Ser Ser Leu
    370                 375                 380
Leu Ser Ser Gly Phe Ser Pro Asp Phe Ala Thr Val Ile Thr Met Asp
385                 390                 395                 400
Arg Lys Ala Ser Lys Gln Gln Thr Asn Ile Asp Val Ile Tyr Glu Arg
                405                 410                 415
Val Arg Asp Asp Tyr Gln Leu His Trp Thr Ser Thr Asn Trp Lys Gly
            420                 425                 430
Thr Asn Thr Lys Asp Lys Trp Ile Asp Arg Ser Ser Glu Arg Tyr Lys
        435                 440                 445
Ile Asp Trp Glu Lys Glu Glu Met Thr Asn Val Asp Lys Leu Ala Ala
    450                 455                 460
Ala Leu Glu His His His His His
465                 470

<210> SEQ ID NO 29
<211> LENGTH: 20
<212> TYPE: PRT
```

```
<213> ORGANISM: Chlamydia trachomatis

<400> SEQUENCE: 29

Asn Val Thr Gln Asp Leu Thr Ser Ser Thr Ala Lys Leu Glu Cys Thr
1               5                   10                  15

Gln Asp Leu Ile
            20

<210> SEQ ID NO 30
<211> LENGTH: 20
<212> TYPE: PRT
<213> ORGANISM: Chlamydia trachomatis

<400> SEQUENCE: 30

Ala Lys Leu Glu Cys Thr Gln Asp Leu Ile Ala Gln Gly Lys Leu Ile
1               5                   10                  15

Val Thr Asn Pro
            20

<210> SEQ ID NO 31
<211> LENGTH: 9
<212> TYPE: PRT
<213> ORGANISM: Chlamydia trachomatis

<400> SEQUENCE: 31

Ser Asn Leu Lys Arg Met Gln Lys Ile
1               5

<210> SEQ ID NO 32
<211> LENGTH: 9
<212> TYPE: PRT
<213> ORGANISM: Chlamydia trachomatis

<400> SEQUENCE: 32

Ala Ala Leu Tyr Ser Thr Glu Asp Leu
1               5

<210> SEQ ID NO 33
<211> LENGTH: 9
<212> TYPE: PRT
<213> ORGANISM: Chlamydia trachomatis

<400> SEQUENCE: 33

Phe Gln Glu Lys Asp Ala Asp Thr Leu
1               5

<210> SEQ ID NO 34
<211> LENGTH: 9
<212> TYPE: PRT
<213> ORGANISM: Chlamydia trachomatis

<400> SEQUENCE: 34

Gln Ser Val Asn Glu Leu Val Tyr Val
1               5

<210> SEQ ID NO 35
<211> LENGTH: 9
<212> TYPE: PRT
<213> ORGANISM: Chlamydia trachomatis

<400> SEQUENCE: 35

Leu Glu Phe Ala Ser Cys Ser Ser Leu
1               5
```

<210> SEQ ID NO 36
<211> LENGTH: 9
<212> TYPE: PRT
<213> ORGANISM: Chlamydia trachomatis

<400> SEQUENCE: 36

Ser Gln Ala Glu Gly Gln Tyr Arg Leu
1               5

<210> SEQ ID NO 37
<211> LENGTH: 9
<212> TYPE: PRT
<213> ORGANISM: Chlamydia trachomatis

<400> SEQUENCE: 37

Gly Gln Ser Val Asn Glu Leu Val Tyr
1               5

<210> SEQ ID NO 38
<211> LENGTH: 9
<212> TYPE: PRT
<213> ORGANISM: Chlamydia trachomatis

<400> SEQUENCE: 38

Gln Ala Val Leu Leu Leu Asp Gln Ile
1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Arg or Leu
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (6)..(6)
<223> OTHER INFORMATION: Tyr or Trp

<400> SEQUENCE: 39

Asp Xaa Ala Xaa Pro Xaa
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Arg or Leu
<220> FEATURE:
<221> NAME/KEY: MOD_RES
<222> LOCATION: (5)..(5)
<223> OTHER INFORMATION: Ser or Thr
<220> FEATURE:
<221> NAME/KEY: MOD_RES
<222> LOCATION: (7)..(7)
<223> OTHER INFORMATION: Tyr or Trp

```
<400> SEQUENCE: 40

Cys Asp Xaa Ala Xaa Pro Xaa Cys Gly
1               5

<210> SEQ ID NO 41
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Ser Pro Gly Ile Ser Gly Gly Gly Gly Gly Ile Leu Glu
1               5                   10

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 42

Leu Pro Xaa Thr Gly
1               5

<210> SEQ ID NO 43
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Pro Glu Pro
1

<210> SEQ ID NO 44
<211> LENGTH: 24
<212> TYPE: PRT
<213> ORGANISM: Listeria monocytogenes

<400> SEQUENCE: 44

Met Lys Lys Ile Met Leu Val Ile Thr Leu Ile Leu Val Ser Pro Ile
1               5                   10                  15

Ala Gln Gln Thr Glu Ala Lys Asp
            20

<210> SEQ ID NO 45
<211> LENGTH: 29
<212> TYPE: PRT
<213> ORGANISM: Lactococcus lactis

<400> SEQUENCE: 45

Met Lys Lys Lys Ile Ile Ser Ala Ile Leu Met Ser Thr Val Ile Leu
1               5                   10                  15

Ser Ala Ala Ala Pro Leu Ser Gly Val Tyr Ala Asp Thr
            20                  25
```

<210> SEQ ID NO 46
<211> LENGTH: 31
<212> TYPE: PRT
<213> ORGANISM: Bacillus anthracis

<400> SEQUENCE: 46

Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala Glu Val
            20                  25                  30

<210> SEQ ID NO 47
<211> LENGTH: 29
<212> TYPE: PRT
<213> ORGANISM: Listeria monocytogenes

<400> SEQUENCE: 47

Met Asn Met Lys Lys Ala Thr Ile Ala Ala Thr Ala Gly Ile Ala Val
1               5                   10                  15

Thr Ala Phe Ala Ala Pro Thr Ile Ala Ser Ala Ser Thr
            20                  25

<210> SEQ ID NO 48
<211> LENGTH: 54
<212> TYPE: PRT
<213> ORGANISM: Listeria monocytogenes

<400> SEQUENCE: 48

Met Gln Lys Thr Arg Lys Glu Arg Ile Leu Glu Ala Leu Gln Glu Glu
1               5                   10                  15

Lys Lys Asn Lys Lys Ser Lys Lys Phe Lys Thr Gly Ala Thr Ile Ala
            20                  25                  30

Gly Val Thr Ala Ile Ala Thr Ser Ile Thr Val Pro Gly Ile Glu Val
        35                  40                  45

Ile Val Ser Ala Asp Glu
    50

<210> SEQ ID NO 49
<211> LENGTH: 28
<212> TYPE: PRT
<213> ORGANISM: Bacillus anthracis

<400> SEQUENCE: 49

Met Lys Lys Leu Lys Met Ala Ser Cys Ala Leu Val Ala Gly Leu Met
1               5                   10                  15

Phe Ser Gly Leu Thr Pro Asn Ala Phe Ala Glu Asp
            20                  25

<210> SEQ ID NO 50
<211> LENGTH: 31
<212> TYPE: PRT
<213> ORGANISM: Staphylococcus aureus

<400> SEQUENCE: 50

Met Ala Lys Lys Phe Asn Tyr Lys Leu Pro Ser Met Val Ala Leu Thr
1               5                   10                  15

Leu Val Gly Ser Ala Val Thr Ala His Gln Val Gln Ala Ala Glu
            20                  25                  30

<210> SEQ ID NO 51

<211> LENGTH: 59
<212> TYPE: PRT
<213> ORGANISM: Listeria monocytogenes

<400> SEQUENCE: 51

Met Thr Asp Lys Lys Ser Glu Asn Gln Thr Glu Lys Thr Glu Thr Lys
1               5                   10                  15

Glu Asn Lys Gly Met Thr Arg Arg Glu Met Leu Lys Leu Ser Ala Val
            20                  25                  30

Ala Gly Thr Gly Ile Ala Val Gly Ala Thr Gly Leu Gly Thr Ile Leu
        35                  40                  45

Asn Val Val Asp Gln Val Asp Lys Ala Leu Thr
    50                  55

<210> SEQ ID NO 52
<211> LENGTH: 53
<212> TYPE: PRT
<213> ORGANISM: Bacillus subtillis

<400> SEQUENCE: 52

Met Ala Tyr Asp Ser Arg Phe Asp Glu Trp Val Gln Lys Leu Lys Glu
1               5                   10                  15

Glu Ser Phe Gln Asn Asn Thr Phe Asp Arg Arg Lys Phe Ile Gln Gly
            20                  25                  30

Ala Gly Lys Ile Ala Gly Leu Gly Leu Gly Leu Thr Ile Ala Gln Ser
        35                  40                  45

Val Gly Ala Phe Gly
    50

<210> SEQ ID NO 53
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Lys Lys Val Ala Ala Phe Val Ala Leu Ser Leu Leu Met Ala Gly
1               5                   10                  15

Cys Val Ser Pro Asp Phe Asp Ala Ser Asn Phe Lys Asp Phe Ser Ser
            20                  25                  30

Ile Ala Ser Ala Ser Ser Ser Trp Gln Asn Gln Ser Gly Ser Thr Met
        35                  40                  45

Ile Ile Gln Val Asp Ser Phe Gly Asn Val Ser Gly Gln Tyr Val Asn
    50                  55                  60

Arg Ala Gln Gly Thr Gly Cys Gln Asn Ser Pro Tyr Pro Leu Thr Gly
65                  70                  75                  80

Arg Val Asn Gly Thr Phe Ile Ala Phe Ser Val Gly Trp Asn Asn Ser
                85                  90                  95

Thr Glu Asn Cys Asn Ser Ala Thr Gly Trp Thr Gly Tyr Ala Gln Val
            100                 105                 110

Asn Gly Asn Asn Thr Glu Ile Val Thr Ser Trp Asn Leu Ala Tyr Glu
        115                 120                 125

Gly Gly Ser Gly Pro Ala Ile Glu Gln Gly Gln Asp Thr Phe Gln Tyr
    130                 135                 140

Val Pro Thr Thr Glu Asn Lys Ser Leu Leu Lys Asp Gly Gly Gly Gly
145                 150                 155                 160

```
Ser Ser Ser Ala Asp Ser Asp Ile Asn Ile Lys Thr Gly Thr Thr Asp
            165                 170                 175

Ile Gly Ser Asn Thr Thr Val Lys Thr Gly Asp Leu Val Thr Tyr Asp
        180                 185                 190

Lys Glu Asn Gly Met His Lys Lys Val Phe Tyr Ser Phe Ile Asp Asp
    195                 200                 205

Lys Asn His Asn Lys Lys Leu Leu Val Ile Arg Thr Lys Gly Thr Ile
210                 215                 220

Ala Gly Gln Tyr Arg Val Tyr Ser Glu Glu Gly Ala Asn Lys Ser Gly
225                 230                 235                 240

Leu Ala Trp Pro Ser Ala Phe Lys Val Gln Leu Gln Leu Pro Asp Asn
            245                 250                 255

Glu Val Ala Gln Ile Ser Asp Tyr Tyr Pro Arg Asn Ser Ile Asp Thr
            260                 265                 270

Lys Glu Tyr Met Ser Thr Leu Thr Tyr Gly Phe Asn Gly Asn Val Thr
        275                 280                 285

Gly Asp Asp Thr Gly Lys Ile Gly Gly Leu Ile Gly Ala Asn Val Ser
    290                 295                 300

Ile Gly His Thr Leu Lys Tyr Val Gln Pro Asp Phe Lys Thr Ile Leu
305                 310                 315                 320

Glu Ser Pro Thr Asp Lys Lys Val Gly Trp Lys Val Ile Phe Asn Asn
            325                 330                 335

Met Val Asn Gln Asn Ala Gly Pro Tyr Asp Arg Asp Ser Trp Asn Pro
            340                 345                 350

Val Tyr Gly Asn Gln Leu Phe Met Lys Thr Arg Asn Gly Ser Met Lys
        355                 360                 365

Ala Ala Asp Asn Phe Leu Asp Pro Asn Lys Ala Ser Ser Leu Leu Ser
    370                 375                 380

Ser Gly Phe Ser Pro Asp Phe Ala Thr Val Ile Thr Met Asp Arg Lys
385                 390                 395                 400

Ala Ser Lys Gln Gln Thr Asn Ile Asp Val Ile Tyr Glu Arg Val Arg
            405                 410                 415

Asp Asp Tyr Gln Leu His Trp Thr Ser Thr Asn Trp Lys Gly Thr Asn
            420                 425                 430

Thr Lys Asp Lys Trp Ile Asp Arg Ser Ser Glu Arg Tyr Lys Ile Asp
        435                 440                 445

Trp Glu Lys Glu Glu Met Thr Asn Val Asp Lys Leu Ala Ala Ala Leu
    450                 455                 460

Glu His His His His His
465                 470

<210> SEQ ID NO 54
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Lys Lys Val Ala Ala Phe Val Ala Leu Ser Leu Leu Met Ala Gly
1               5                   10                  15

Cys Val Ser Pro Asp Phe Asp Ala Ser Asn Phe Lys Asp Phe Ser Ser
            20                  25                  30

Ile Ala Ser Ala Ser Ser Ser Trp Gln Asn Gln Ser Gly Ser Thr Met
        35                  40                  45
```

Ile Ile Gln Val Asp Ser Phe Gly Asn Val Ser Gly Gln Tyr Val Asn
            50                  55                  60

Arg Ala Gln Gly Thr Gly Cys Gln Asn Ser Pro Tyr Pro Leu Thr Gly
65                  70                  75                  80

Arg Val Asn Gly Thr Phe Ile Ala Phe Ser Val Gly Trp Asn Asn Ser
                85                  90                  95

Thr Glu Asn Cys Asn Ser Ala Thr Gly Trp Thr Gly Tyr Ala Gln Val
            100                 105                 110

Asn Gly Asn Asn Thr Glu Ile Val Thr Ser Trp Asn Leu Ala Tyr Glu
            115                 120                 125

Gly Gly Ser Gly Pro Ala Ile Glu Gln Gly Gln Asp Thr Phe Gln Tyr
            130                 135                 140

Val Pro Thr Thr Glu Asn Lys Ser Leu Leu Lys Asp Gly Gly Gly
145                 150                 155                 160

Ser Ser Ser Ala Asp Ser Asp Ile Asn Ile Lys Thr Gly Thr Thr Asp
                165                 170                 175

Ile Gly Ser Asn Thr Thr Val Lys Thr Gly Asp Leu Val Thr Tyr Asp
                180                 185                 190

Lys Glu Asn Gly Met His Lys Val Phe Tyr Ser Phe Ile Asp Asp
            195                 200                 205

Lys Asn His Asn Lys Lys Leu Leu Val Ile Arg Thr Lys Gly Thr Ile
210                 215                 220

Ala Gly Gln Tyr Arg Val Tyr Ser Glu Glu Gly Ala Asn Lys Ser Gly
225                 230                 235                 240

Leu Ala Trp Pro Ser Ala Phe Lys Val Gln Leu Gln Leu Pro Asp Asn
                245                 250                 255

Glu Val Ala Gln Ile Ser Asp Tyr Tyr Pro Arg Asn Ser Ile Asp Thr
            260                 265                 270

Lys Glu Tyr Met Ser Thr Leu Thr Tyr Gly Phe Asn Gly Asn Val Thr
            275                 280                 285

Gly Asp Asp Thr Gly Lys Ile Gly Gly Leu Ile Gly Ala Asn Val Ser
            290                 295                 300

Ile Gly His Thr Leu Lys Tyr Val Gln Pro Asp Phe Lys Thr Ile Leu
305                 310                 315                 320

Glu Ser Pro Thr Asp Lys Lys Val Gly Trp Lys Val Ile Phe Asn Asn
                325                 330                 335

Met Val Asn Gln Asn Trp Gly Pro Tyr Asp Arg Asp Ser Ala Asn Pro
            340                 345                 350

Val Tyr Gly Asn Gln Leu Phe Met Lys Thr Arg Asn Gly Ser Met Lys
            355                 360                 365

Ala Ala Asp Asn Phe Leu Asp Pro Asn Lys Ala Ser Ser Leu Leu Ser
            370                 375                 380

Ser Gly Phe Ser Pro Asp Phe Ala Thr Val Ile Thr Met Asp Arg Lys
385                 390                 395                 400

Ala Ser Lys Gln Gln Thr Asn Ile Asp Val Ile Tyr Glu Arg Val Arg
                405                 410                 415

Asp Asp Tyr Gln Leu His Trp Thr Ser Thr Asn Trp Lys Gly Thr Asn
            420                 425                 430

Thr Lys Asp Lys Trp Ile Asp Arg Ser Ser Glu Arg Tyr Lys Ile Asp
            435                 440                 445

Trp Glu Lys Glu Glu Met Thr Asn Val Asp Lys Leu Ala Ala Leu
    450                 455                 460

```
Glu His His His His His
465                 470

<210> SEQ ID NO 55
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Lys Lys Val Ala Ala Phe Val Ala Leu Ser Leu Leu Met Ala Gly
1               5                   10                  15

Cys Val Ser Pro Asp Phe Asp Ala Ser Asn Phe Lys Asp Phe Ser Ser
            20                  25                  30

Ile Ala Ser Ala Ser Ser Trp Gln Asn Gln Ser Gly Ser Thr Met
        35                  40                  45

Ile Ile Gln Val Asp Ser Phe Gly Asn Val Ser Gly Gln Tyr Val Asn
    50                  55                  60

Arg Ala Gln Gly Thr Gly Cys Gln Asn Ser Pro Tyr Pro Leu Thr Gly
65                  70                  75                  80

Arg Val Asn Gly Thr Phe Ile Ala Phe Ser Val Gly Trp Asn Asn Ser
                85                  90                  95

Thr Glu Asn Cys Asn Ser Ala Thr Gly Trp Thr Gly Tyr Ala Gln Val
            100                 105                 110

Asn Gly Asn Asn Thr Glu Ile Val Thr Ser Trp Asn Leu Ala Tyr Glu
        115                 120                 125

Gly Gly Ser Gly Pro Ala Ile Glu Gln Gly Gln Asp Thr Phe Gln Tyr
    130                 135                 140

Val Pro Thr Thr Glu Asn Lys Ser Leu Leu Lys Asp Gly Gly Gly Gly
145                 150                 155                 160

Ser Ser Ser Ala Asp Ser Asp Ile Asn Ile Lys Thr Gly Thr Thr Asp
                165                 170                 175

Ile Gly Ser Asn Thr Thr Val Lys Thr Gly Asp Leu Val Thr Tyr Asp
            180                 185                 190

Lys Glu Asn Gly Met His Lys Lys Val Phe Tyr Ser Phe Ile Asp Asp
        195                 200                 205

Lys Asn His Asn Lys Lys Leu Leu Val Ile Arg Thr Lys Gly Thr Ile
    210                 215                 220

Ala Gly Gln Tyr Arg Val Tyr Ser Glu Glu Gly Ala Asn Lys Ser Gly
225                 230                 235                 240

Leu Ala Trp Pro Ser Ala Phe Lys Val Gln Leu Gln Leu Pro Asp Asn
                245                 250                 255

Glu Val Ala Gln Ile Ser Asp Tyr Tyr Pro Arg Asn Ser Ile Asp Thr
            260                 265                 270

Lys Glu Tyr Met Ser Thr Leu Thr Tyr Gly Phe Asn Gly Asn Val Thr
        275                 280                 285

Gly Asp Asp Thr Gly Lys Ile Gly Gly Leu Ile Gly Ala Asn Val Ser
    290                 295                 300

Ile Gly His Thr Leu Lys Tyr Val Gln Pro Asp Phe Lys Thr Ile Leu
305                 310                 315                 320

Glu Ser Pro Thr Asp Lys Lys Val Gly Trp Lys Val Ile Phe Asn Asn
                325                 330                 335

Met Val Asn Gln Asn Trp Gly Pro Tyr Ala Ala Ala Ser Trp Asn Pro
            340                 345                 350
```

```
Val Tyr Gly Asn Gln Leu Phe Met Lys Thr Arg Asn Gly Ser Met Lys
            355                 360                 365

Ala Ala Asp Asn Phe Leu Asp Pro Asn Lys Ala Ser Ser Leu Leu Ser
        370                 375                 380

Ser Gly Phe Ser Pro Asp Phe Ala Thr Val Ile Thr Met Asp Arg Lys
385                 390                 395                 400

Ala Ser Lys Gln Gln Thr Asn Ile Asp Val Ile Tyr Glu Arg Val Arg
                405                 410                 415

Asp Asp Tyr Gln Leu His Trp Thr Ser Thr Asn Trp Lys Gly Thr Asn
            420                 425                 430

Thr Lys Asp Lys Trp Ile Asp Arg Ser Ser Glu Arg Tyr Lys Ile Asp
        435                 440                 445

Trp Glu Lys Glu Glu Met Thr Asn Val Asp Lys Leu Ala Ala Ala Leu
    450                 455                 460

Glu His His His His His
465                 470

<210> SEQ ID NO 56
<211> LENGTH: 23
<212> TYPE: PRT
<213> ORGANISM: Unknown
<220> FEATURE:
<223> OTHER INFORMATION: Description of Unknown: Signal
      peptide

<400> SEQUENCE: 56

Met Lys Lys Ile Trp Leu Ala Leu Ala Gly Leu Val Leu Ala Phe Ser
1               5                   10                  15

Ala Ser Ala Ala Gln Asp Pro
            20

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Leu Glu His His His His His His
1               5

<210> SEQ ID NO 58
<211> LENGTH: 21
<212> TYPE: PRT
<213> ORGANISM: Unknown
<220> FEATURE:
<223> OTHER INFORMATION: Description of Unknown: Signal
      peptide

<400> SEQUENCE: 58

Met Lys Lys Val Ala Ala Phe Val Ala Leu Ser Leu Leu Met Ala Gly
1               5                   10                  15

Cys Val Ser Asp Pro
            20
```

MODIFIED BIOTIN-BINDING PROTEIN, FUSION PROTEINS THEREOF AND APPLICATIONS

CROSS REFERENCE TO RELATED APPLICATIONS

This application is a continuation application of U.S. Ser. No. 14/946,372 filed Nov. 19, 2015, which is a divisional application of U.S. Ser. No. 14/116,492 filed Jan. 27, 2014, now U.S. Pat. No. 9,499,593 issued Nov. 22, 2016, which application is a 35 U.S.C. § 371 National Phase Entry Application of International Application No. PCT/US2012/037541 filed May 11, 2012, which designates the U.S., and which claims benefit under 35 U.S.C. § 119(e) of the U.S. Provisional Application Ser. No. 61/484,934 filed May 11, 2011, U.S. Provisional Application Ser. No. 61/608,168, filed Mar. 8, 2012, and U.S. Provisional Application Ser. No. 61/609,974, filed Mar. 13, 2012, the contents of each of which is are incorporated fully herein by reference in their entireties.

GOVERNMENT SUPPORT

This invention was made with government support under Grant Numbers AI066013 and AI067737 awarded by the National Institutes of Health. The Government has certain rights in the invention.

SEQUENCE LISTING

The instant application contains a Sequence Listing which has been submitted in ASCII format via EFS-Web and is hereby incorporated by reference in its entirety. Said ASCII copy, created on May 29, 2018, is named 701039-074341_SL and is 55,307 bytes in size.

TECHNICAL FIELD

The present disclosure relates to biotin-binding proteins and the fusion proteins/compositions comprising such biotin-binding proteins. Also described herein are methods for expressing biotin-binding proteins and/or the fusion proteins thereof in high yield and in soluble in bacteria.

BACKGROUND

Biotin-binding protein and their derivatives can be widely used in various applications. However, production or purification of recombinant biotin-binding proteins can be very difficult. When expressed in E. coli, most biotin-binding proteins tend to accumulate in inclusion bodies, denaturing, refolding and tedious downstream processing are required in the preparation of active proteins. Expression in E. coli is preferable because of the low cost of production and the potential for further engineering; thus, biotin-binding proteins that can be efficiently produced in E. coli are highly sought after. Further, expression E. coli also provides the possibility to generate recombinant fusion proteins containing biotin-binding protein for various applications.

Accordingly, there is need in the art for biotin-binding proteins and fusion proteins containing biotin-binding proteins which can be expressed in soluble form in high yields in E. coli.

SUMMARY

One objective of the present disclosure is to provide a recombinant biotin-binding protein, which can be expressed in soluble form in high yields in E. coli. Accordingly, the present disclosure provides biotin-binding proteins and compositions comprising the same. In some embodiments, the recombinant biotin-binding protein comprises an E. coli signal sequence fused to the N-terminus of an amino acid sequence comprising amino acids 45-179 (FDASNFKDF-SSIASASSSWQNQSGSTMIIQVDSFGNVSGQYVN-RAQGTGCQNSPYPLTGRVNGTFIA FSVG-WNNSTENCNSATGWTGYAQVNGNNTEIVTSWNLA-YEGGSGPAIEQGQDTFQYVPTTENKSL LKD, SEQ ID NO: 1) of wild-type Rhizavidin (rhavi). In some embodiments, the E. coli signal sequence is MKKIWLALAGLV-LAFSASA (SEQ ID No: 2). The signal sequence can be fused with the sequence comprising amino acids 45-179 of wild-type rhavi by a flexible peptide linker.

Provided herein is also a method of expressing a biotin-binding protein in soluble form in high yield in E. coli. In some embodiments, the method comprising expressing a biotin-binding protein in E. coli, wherein the native signal sequence of the biotin-binding protein has been replaced by an E. coli signal sequence. In some embodiments, the signal sequence is MKKIWLALAGLVLAFSASA (SEQ ID No: 2)

In yet another aspect, the invention provides biotin-binding fusion protein comprising a biotin-binding domain and a protein or a peptide.

In another aspect provided herein is a lipidated biotin-binding protein. As used herein, the term "lipidated biotin-binding protein" refers to a biotin-binding protein that is covalently linked with a lipid. The lipidated biotin-binding proteins are ligands or agonists of Toll like receptor 2. Accordingly, also provided herein are methods for inducing an immune response in subject. The method comprising administering to the subject a composition comprising a lipidated biotin-binding protein.

Provided herein is also a method of expressing a lipidated biotin-binding protein in E. coli. In some embodiments, the method comprises expressing a lipidated biotin-binding protein in E. coli, wherein the native signal sequence of the biotin-binding protein has been replaced by an E. coli signal sequence containing a lipidation motif. In some embodiments, the signal sequence is MKKVAAFVALSLLMAGC (SEQ ID No: 3)

In still another aspect, provided herein is a non-hemolytic derivative of Staphylococcal aureus alpha-hemolysin (Hla). The Hla derivative described herein can be in the form of a fusion protein, wherein the fusion protein comprises both the Hla derivative domain and a biotin-binding domain. In some embodiments of this aspect, the biotin-binding domain is a biotin-binding protein described herein.

Like the lipidated biotin-binding proteins, the Hla variants or their fusion proteins with biotin-binding proteins described herein are also ligands or agonists of Toll like receptors or other pattern recognition receptors (PRRs). Accordingly, also provided herein are methods for inducing an immune response in subject. In some embodiments, the method comprising administering to the subject a composition comprising a non-hemolytic Hla variants or their fusion proteins with biotin-binding protein described herein.

In yet still another aspect, provided herein is an immunogenic composition or vaccine composition comprising a biotin-binding protein, a lipidated biotin-binding protein, a biotin-binding fusion protein comprising a biotin-binding domain and an antigenic protein or peptide. In some embodiments of this aspect, the antigenic protein is a non-hemolytic derivative of Hla described herein.

Provided herein also is a method of vaccinating a subject, e.g., a mammal, e.g., a human with the immunogenic compositions as disclosed herein, the method comprising administering a vaccine composition as disclosed herein to the subject.

BRIEF DESCRIPTION OF THE DRAWINGS

FIG. 1 is a schematic representation of a modified biotin-binding protein according to an embodiment disclosed herein. FIG. 1 discloses SEQ ID NOS: 56 and 14, respectively, in order of appearance.

FIG. 2 is a SDS-PAGE of a purified recombinant biotin-binding protein described herein.

FIG. 3 discloses SEQ ID NOS: 56, 22 and 57, respectively, in order of appearance.

FIG. 5 is a schematic representation of lipidated biotin-binding protein according to an embodiment disclosed herein. FIG. 5 discloses SEQ ID NOS: 58 and 14, respectively, in order of appearance.

FIG. 6 is a SDS-PAGE of a lipidated biotin-binding protein described herein.

FIG. 8 discloses SEQ ID NOS: 57, 56, 22 and 57, respectively, in order of appearance.

FIG. 14 is a bar graph showing that multiple antigen presenting system (MAPS) complex containing lipidated rhizavidin or rhavi-Hla209 induces stronger T cell responses to the antigens.

DETAILED DESCRIPTION OF EXEMPLARY EMBODIMENTS

Figures 3, 4:
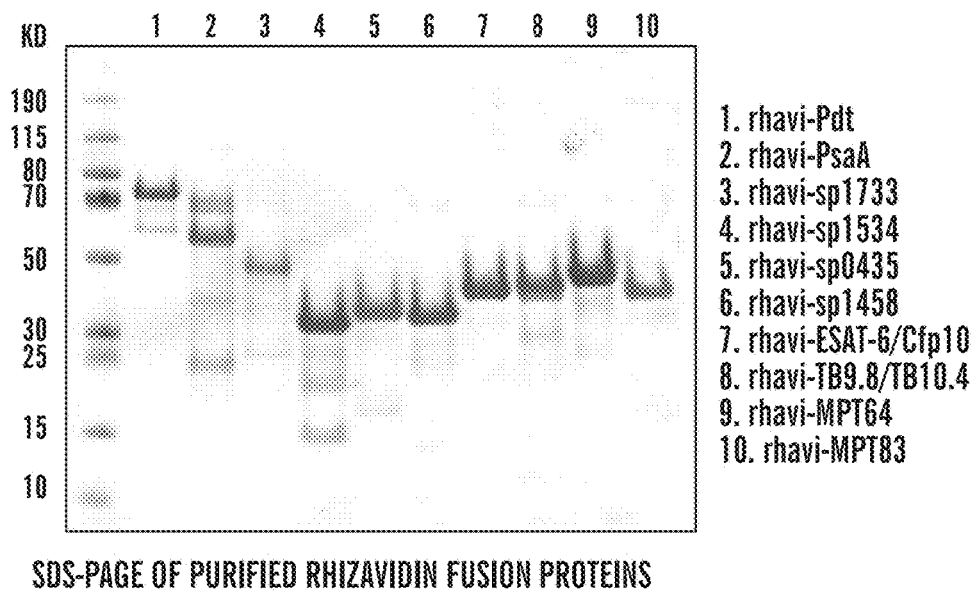
FIG. 3 is a schematic representation of a fusion protein comprising a biotin-binding protein and an antigen X.
FIG. 4 is an exemplary SDS-PAGE of purified rhizavidin fusion proteins

It should be understood that this invention is not limited to the particular composition, methodology, protocols, and reagents, etc., described herein and as such can vary. The terminology used herein is for the purpose of describing particular embodiments only, and is not intended to limit the scope of the present invention, which is defined solely by the claims.

Without wishing to be bound by a theory, low expression of a biotin-binding protein in the art can be due to bad-folding caused by the disulfide bond in each monomer of the biotin-binding protein which does not form, or forms at very low levels, in the cytoplasm of E. coli. Now the inventors have discovered that correct-folding can be achieved by transporting into the periplasmic space of E coli. Thus, correct folding of recombinant biotin-binding proteins can be improved by replacing the complete native signal sequence of a biotin-binding protein with an E. coli secretion signal sequence. Without wishing to be bound by a theory, this facilitates the translocation of recombinant protein into the periplasmic space of E. coli cells. Translocation of recombinant protein into the periplasmic space of E. coli then can provide the functionally important disulfide bond in the biotin-binding protein (e.g., in Rhizavidin) and the protein can fold correctly in a soluble form and in high yields.

In one aspect, provided herein is a biotin-binding protein that can be expressed in a soluble form and high yield in E. coli. As used herein, the term "biotin-binding protein" refers to a protein, which non-covalently binds to biotin or an analogue or derivative thereof. High yield means that the protein can be expressed in a soluble form in E. coli at an amount of about 10 mg/L, 11 mg/L, 12 mg/L, 13 mg/L, 14 mg/L, 15 mg/L, 20 mg/L, 25 mg/L, 30 mg/L, 35 mg/L, 30 mg/L, 35 mg/L, 40 mg/L, 45 mg/L, 50 mg/L or more.

In some embodiments, the biotin-binding protein can be a recombinant protein. The coding sequence for the biotin-binding protein can be optimized using E. coli expression codons, to avoid any difficulty during expression in E. coli due to rare codons present in original gene.

Generally, the biotin-binding protein comprises a biotin-binding domain. As used herein, a "biotin-binding domain" refers to a polypeptide sequence that binds to biotin. While a complete biotin-binding protein can be used as a biotin-binding domain, only the biotin-binding portion of the protein can be used. In some embodiments, the biotin-binding domain is from Rhizavidin.

In some embodiments, the biotin-binding domain consists of, or consists essentially of, the amino acid sequence corresponding to amino acids 45-179 of the wild-type Rhizavidin. Amino acid sequence of the wild-type Rhizavidin is:

(SEQ ID NO: 4)
MIITSLYATFGTIADGRRTSGGKTMIRTNAVAALVFAVATSALAFDASNF

KDFSSIASASSSWQNQSGSTMIIQVDSFGNVSGQYVNRAQGTGCQNSPYP

LTGRVNGTFIAFSVGWNNSTENCNSATGWTGYAQVNGNNTEIVTSWNLAY

EGGSGPAIEQGQDTFQYVPTTENKSLLKD

In other words, the biotin-binding domain does not comprise (i.e., lacks) lacks amino acids 1-44 (MIITSLYATFG-TIADGRRTSGGKTMIRTNAVAALVFAVATSALA, SEQ ID NO: 5). of the wild-type Rhizavidin. In some embodiments, the biotin-binding domain comprises the amino acid sequence (SEQ ID NO: 1)
FDASNFKDFSSIASASSSWQNQSGSTMIIQVDSFGNVSGQYVNRAQGTGC

QNSPYPLTGRVNGTFIAFSVGWNNSTENCNSATGWTGYAQVNGNNTEIVT

SWNLAYEGGSGPAIEQGQDTFQYVPTTENKSLLKD.

In some embodiments, the biotin-binding domain comprises an amino acid sequence having at least 50% identity, at least 55% identity, at least 60% identity, at least 65% identity, at least 70% identity, at least 75% identity, at least 80% identity, preferably at least 85% identity, at least 90% identity, at least 95% identity, at least 96% identity, at least 97% identity, at least 98% identity, or at least 99% identity, and more preferably at least 99.3% identity to SEQ ID NO: 1).

While, Helppolainen et al. (Biochem J., 2007, 405: 397-405) describe removing only first 24 residues of the full length Rhizavidin, the inventors have discovered that the first 44 residues of full length Rhizavidin are unnecessary for the core structure and function of Rhizavidin. Further, unexpectedly, amino acids 25-44 (MIRTNAVAALVFAVAT-SALA, SEQ ID NO: 6) of the full length Rhizavidin reduce the solubility and secretion of Rhizavidin expressed in *E. coli* as replacement of the first 44 residues of full length Rhizavidin with an *E. coli* signal peptide led to an increase in the solubility and secretion in *E. coli* of biotin proteins described herein.

In the biotin-binding protein described herein, the biotin-binding domain can be extended on the N- or C-terminus by one or more amino acids with the proviso that the N-terminus of the biotin-binding domain does not comprise an amino acid sequence corresponding to an amino acid sequence 1-44 of the wild-type Rhizavidin. The inventors have discovered that truncating the first 44 amino acids on the N-terminus of the wild type Rhizavidin can dramatically increase expression of the biotin-binding protein in soluble form in *E. coli*. Thus, the biotin-binding protein described herein can comprise the sequence $X^1$-$X^2$-$X^3$, wherein $X^2$ is a peptide having the amino acid sequence corresponding to amino acids 45-179 of the wild-type Rhizavidin and $X^1$ and $X^3$ are independently absent or a peptide of 1 to about 100 amino acids with the proviso that the N-terminus of $X^1$ does not comprise an amino acid sequence corresponding to N-terminus of amino acids 1-44 of the wild-type Rhizavidin.

In some embodiments, the biotin-binding proteins can comprise a signal peptide conjugated to the N-terminus of the biotin-binding protein, i.e. $X^1$ can comprise a signal peptide. The signal peptide is also called a leader peptide in the N-terminus, which may or may not be cleaved off after the translocation through the membrane. Secretion/signal peptides are described in more detail below. In some embodiments, the signal sequence is MKKIWLALAGLV-LAFSASA (SEQ ID NO: 2), MAPFEPLASGILLLL-WLIAPSRA (SEQ ID NO: 7), MKKVAAFVALSLLMAGC (SEQ ID NO: 3), or a derivative or functional portion thereof.

The signal peptide can be linked to the N-terminus of the biotin-binding domain either directly (e.g., via a bond) or indirectly (e.g., by a linker). In some embodiments, the signal peptide can be linked to the N-terminus of the biotin-binding domain by a peptide linker. The peptide linker sequence can be of any length. For example, the peptide linker sequence can be one, two, three, four, five, six, seven, eight, nine, ten, eleven, twelve, thirteen, fourteen, fifteen or more amino acids in length. In some embodiments, the peptide linker is four amino acids in length.

The peptide linker sequence can comprise any amino acid sequence. For example, the peptide linker can comprise an amino acid sequence which can be cleaved by a signal peptidase. In some embodiments, the peptide linker comprises the amino acid sequence AQDP (SEQ ID NO: 8) or VSDP (SEQ ID NO: 9).

In the biotin-binding protein, the biotin-binding domain can be conjugated at its C-terminus to a peptide of 1-100 amino acids. Such peptides at the C-terminus can be used for purification tags, linkers to other domains, and the like.

In some embodiments, the biotin-binding protein comprises on its N- or C-terminus one or more (e.g., one, two, three, four, five, six, seven, eight, nine, ten or more) purification tags. Examples of purification tags include, but are not limited to a histidine tag, a c-my tag, a Halo tag, a Flag tag, and the like. In some embodiments, the biotin-binding protein comprises on its C-terminus a histidine tag, e.g. a $(His)_6$ (SEQ ID NO. 10).

A purification tag can be conjugated to the biotin-binding protein by a peptide linker to enhance the probability that the tag is exposed to the outside. The length of the linker can be at least one (e.g., one, two, three, four, five six, seven, eight, nine, ten, eleven, twelve, thirteen, fourteen, or fifteen) amino acid. The linker peptide can comprise any amino acid sequence without limitations. In some embodiments, the linker peptide comprises the amino acid sequence VDK-LAAALE (SEQ ID NO: 11) or GGGGSSSVDKLAAALE (SEQ ID NO: 12).

In some embodiments, the biotin-binding protein comprises on its C-terminus the amino acid sequence VDK-LAAALEHHHHH (SEQ ID NO: 13) or GGGGSSSVDK-LAAALEHHHHHH (SEQ ID NO: 14).

In some embodiments, the biotin-binding protein comprises the amino acid sequence:

(SEQ ID NO: 15)
MKKIWLALAGLVLAFSASAAQDPFDASNFKDFSSIASASSSWQNQSGSTM

IIQVDSFGNVSGQYVNRAQGTGCQNSPYPLTGRVNGTFIAFSVGWNNSTE

NCNSATGWTGYAQVNGNNTEIVTSWNLAYEGGSGPAIEQGQDTFQYVPTT

ENKSLLKDGGGGSSSVDKLAAALEHHHHHH.

Compared with known biotin-binding proteins which form tetramers, the biotin-binding protein described herein form a dimer. Without wishing to be bound by a theory, forming a dimer can further improve expression of the biotin-binding protein described herein as a soluble protein in *E. coli*.

Although biotin-binding proteins are known in the art, the biotin-binding protein described herein comprises significant differences from avidin and avidin-like proteins currently known in the art. First, currently known avidins are quite difficult to express as soluble proteins in *E. coli*. However, as the inventors have demonstrated, the biotin-binding protein described herein can be expressed as a soluble protein in *E. coli* in high yield.

The biotin-binding proteins described herein can be obtained in a soluble form in high yields, e.g., over 30 mg per liter of culture, by expression in *E. coli*. Thus, the biotin-binding proteins described herein are more soluble than those described in the art and reflect underlying differences. Without wishing to be bound by a theory, the difference in solubility can be attributed to underlying physical and/or chemical and/or structural differences between biotin-binding proteins described herein and other biotin-binding proteins known in the art.

Second, the biotin-binding protein described herein comprises a biotin-binding domain which consists of amino acids 45-179 of wild-type Rhizavidin. While, wild-type Rhizavidin and a partially truncated portion thereof are known in the art, there is no teaching or suggestion in the art that a biotin-binding protein comprising the amino acids sequence of amino acids 45-179 of wild-type Rhizavidin and having an *E. coli* signal sequence would lead to a soluble protein that can be obtained in high yield in *E. coli*. According to Helppolainen et al. (Biochem J., 2007, 405: 397-405) the amino acids 25-44 of the wild type Rhizavidin comprise a putative signal sequence. However, as discusses herein, the inventors have discovered and demonstrated that replacement of the putative signal sequence with an *E. coli* signal sequence leads to increase in soluble form of the biotin-binding protein expression in *E. coli*.

Third, the biotin-binding protein described comprises a peptide of amino acid sequence GGGGSSSVDKLAAALE-HHHHHH (SEQ ID NO: 14). This peptide at the C-terminus provides a histidine tag for purification and a place for insertion of other domains, e.g. antigenic domains, in the biotin protein. Further, while Helppolainen et al. (Biochem J., 2007, 405: 397-405) describe expression of Rhizavidin in *E. coli*, there is no teaching or suggestion in Helppolainen et al. for conjugating an additional peptide to the C-terminus of the biotin-binding domain of Rhizavidin.

Fourth, Rhizavidin has a lower sequence homology to egg avidin (22.4% sequence identity and 35.0% similarity) compared with other avidin-like proteins. Thus, the biotin-binding protein described herein is different avidin and other avidin-like proteins.

Fifth, the biotin-binding protein described herein has a low isoelectric point (pI) compared to the avidin and other avidin-like molecules. The isoelectric point of the wild type Rhizavidin is 4.0 (Helppolainen et al., Biochem J., 2007, 405: 397-405). The isoelectric point of other known biotin-binding proteins is generally over 6.1 (see Helppolainen et al., Biochem J., 2007, 405: 397-405). In comparison, the pI of the biotin-binding protein described herein is 5.4. The acidic pI of the binding-protein described herein leads to reduced non-specific binding. A problem in the use of currently known avidin and avidin-like peptides is non-specific binding thereof. Currently known avidin and avidin-like peptides can non-specifically bind to not only cells but also DNAs, proteins, and biological materials such as membranes. For example, in detection of a material using the avidin-biotin binding, avidin non-specifically binds to materials other than the object material to be detected to increase the background. One reason for the high non-specific binding of avidin include its high isoelectric point. Avidin is a strongly basic protein, having a significantly high isoelectric point of 10 or more, and is positively charged as a whole. Accordingly, it is believed that avidin readily binds to biological materials, which are negatively charged in many cases. Thus, the low pI of the biotin-binding protein described herein is advantageous over the currently known avidin and avidin-like peptides.

Sixth, size of the biotin-binding protein described herein is a relatively small compared to currently known avidin and avidin-like proteins. The biotin-binding protein is smaller than 28 kDa (dimer size). However, most of the currently known avidin and avidin-like proteins all have sizes larger than 60 kDa (tetramer size). Wild-type Rhizavidin is said to be about 29 kDa (dimer size) in size. Small size of the biotin-binding protein can be used to increase loading of binding conjugation between molecules interest. For example, the biotin-binding protein can be used to conjugate first molecule of interest with a second molecule of interest. One of the molecules of interest can be linked to one or more biotin or biotin-like molecules and the second molecule can be linked, conjugated or fused to the biotin-binding protein. Given the small size of the biotin-protein described herein, the biotin or biotin-like molecules can be spaced closer together on the to permit binding of more relative to if the second molecule was a larger currently known avidin or avidin-like molecule.

Seventh, the biotin-binding protein described herein is a dimer. Forming a dimer can further improve expression of the biotin-binding protein described herein as a soluble protein in *E. coli*. Additionally, because the biotin-binding protein forms a dimer rather than tetramer like all other known avidin-like proteins, 1) the structural complexity of the fusion antigens is reduced; 2) the difficulty of expressing recombinant biotin-binding protein fusion proteins is similarly reduced, 3) the steric hindrance of manipulations of biotin-binding protein fusions is minimized, which is advantageous for further manipulations with, for example, but not limited to, biotin, biotin mimetics or biotin derivatives, and 4) solubility of biotin-binding protein fusions is greatly enhanced. Thus, demonstrating underlying differences between the biotin-binding proteins described herein and those known in the art.

Eighth, the biotin-binding protein described herein reduces the risk of an immunogenic composition comprising the same inducing an egg-related allergic reaction in a subject. Moreover, antibody to biotin-binding domain described herein has no apparent cross-reactivity to egg avidin (and vice versa).

Further, a biotin-binding protein described herein can have improved properties, such as a reduction in non-specific binding or a further improvement in biotin binding, while retaining the characteristics of wild-type Rhizavidin. The use of the biotin-binding protein described herein for detection, for example, in immunoassay or nucleic acid hybridization assay, for measuring an analyte utilizing avidin-biotin binding can reduce background, increase sensitivity, and maintain the binding property with biotin in severe conditions.

This study clearly demonstrates the advantages and differences of the biotin-binding proteins described herein over avidin and other avidin-like proteins. Thus, the biotin-binding proteins described herein have a potential as a powerful and versatile tool in a wide range of applications utilizing avidin-biotin technology.

Without limitations, a biotin-binding protein can be used in any methodology, composition, or system requiring the use of an avidin-biotin system. As one of ordinary skill is well aware, the avidin-biotin system can be used for numerous laboratory methods, such as bioconjugation; target molecule detection; target molecule isolation, purification, or enrichment from a sample; protein detection; nucleic acid detection; protein isolation, purification, or enrichment; nucleic acid isolation, purification, or enrichment; ELISA; flow cytometry; and the like.

Accordingly, exemplary uses for the recombinant biotin-binding proteins described herein include, but are not limited to, bioconjugation; target molecule detection; target molecule isolation, purification, or enrichment from a sample; protein detection; nucleic acid detection; protein isolation, purification, or enrichment; nucleic acid isolation, purification, or enrichment; ELISA; flow cytometry; and the like.

In some embodiments, the biotin-binding protein described herein can be used as part of the affinity pair in the multiple antigen presenting system (MAPS) as described in U.S. Provisional application No. 61/48,934, filed May 11, 2012; No. 61/608,168, filed Mar. 8, 2012; and No. 61/609,974, filed Mar. 13, 2012, and PCT application no. PCT/US12/37412, filed May 11, 2012, content of all of which is incorporated herein by reference in its entirety. MAPS is also described in more detail herein below. Without wishing to be bound by a theory, use of a biotin-binding protein described herein reduces the risk of the MAPS inducing an egg-related allergic reaction in a subject. Moreover, antibody to recombinant modified Rhizavidin has no apparent cross-reactivity to egg avidin (and vice versa).

Lipidated Biotin-Binding Protein

In another aspect provided herein is a lipidated biotin-binding protein. As used herein, the term "lipidated biotin-binding protein" refers to a biotin-binding protein that is covalently conjugated with a lipid. The lipid moieties could be a diacyl or triacyl lipid.

The lipidated biotin-binding protein can be made using a lipidation sequence. As used herein, the term "lipidation sequence" refers to an amino acid sequence that facilitates lipidation in a bacteria, e.g., E. coli, of a polypeptide carrying the lipidating sequence. The lipidation sequence can be present at the N-terminus or the C-terminus of the protein. The lipidation sequence can be linked to the recombinant biotin-binding protein to form a fusion protein, which is in lipidated form when expressed in E. coli by conventional recombinant technology. In some embodiments, a lipidation sequence is located at the N-terminus of the biotin-binding protein.

Any lipidation sequence known to one of ordinary skill in the art can be used. In some embodiments, the lipidating sequence is MKKVAAFVALSLLMAGC (SEQ ID NO: 3) or a derivative or functional portion thereof. Other exemplary lididationg sequences include, but are not limited to, MNSKKLCCICVLFSLLAGCAS (SEQ ID NO: 16), MRYSKLTMLIPCALLLSAC (SEQ ID NO: 17), MFVTSKKMTAAVLAITLAMSLSAC (SEQ ID NO: 18), MIKRVLVVSMVGLSLVGC (SEQ ID NO: 19), and derivatives or functional portions thereof.

In some embodiments, the lipidation sequence can be fused to the biotin-binding protein via a peptide linker, wherein the peptide linker attaches the lipidating sequence to the biotin-binding protein.

In some embodiment, the peptide linker comprises the amino acid sequence VSDP (SEQ ID NO: 9).

In one embodiment, the biotin-binding lipid protein comprises the amino acid sequence (SEQ ID NO: 20)
MKKVAAFVALSLLMAGCVSDPFDASNFKDFSSIASASSSWQNQSGSTMII

QVDSFGNVSGQYVNRAQGTGCQNSPYPLTGRVNGTFIAFSVGWNNSTENC

NSATGWTGYAQVNGNNTEIVTSWNLAYEGGSGPAIEQGQDTFQYVPTTEN

KSLLKD.

The lipidated biotin-binding proteins are ligands for Toll Like Receptors (TLRs). As such, the lipidated biotin-binding proteins described herein can be used as TLR ligands. For example, the lipidated biotin-binding protein can be used in compositions to induce TLR2 stimulation. This can be useful for inducing immunogenicity to other antigens/pathogens. Thus, the biotin-binding lipoproteins can be used in immunogenic compositions as a co-stimulation factor or adjuvant for an antigen.

As used herein, the term "Toll Like Receptor" is meant to refer in general to any Toll-like receptor of any species of organism. A TLR can be from any mammalian species. TLRs have been identified in various mammalian species including, but not limited to, for example, humans, guinea pigs, and mice. A specific TLR can be identified with additional reference to species of origin (e.g., human, murine, etc. . . . ), a particular receptor (e.g., TLR2, TLR3, TLR9, etc. . . . ), or both. In some embodiments, the lipidated biotin-binding protein is a ligand for TLR2.

Toll-like receptors (TLRs) are a family of germline encoded transmembrane proteins that facilitate pathogen recognition and activation of the innate immune system. Toll-like receptors (TLRs) are pattern recognition receptors (PRRs), and are expressed by cells of the innate immune system, including macrophages, dendritic cells and NK cells. Examples of known ligands for TLRs include gram positive bacteria (TLR-2), bacterial endotoxin (TLR-4), flagellin protein (TLR-5), bacterial DNA (TLR-9), double-stranded RNA and poly I:C (TLR-3), and yeast (TLR-2). Other ligands that bind an endocytic pattern recognition receptor, a scavenger receptor or a mannose-binding receptor can also be contemplated by the instant invention. TLRs engage conserved pathogen-derived ligands and subsequently activate the TLR/IL-1R signal transduction pathway to induce a variety of effector genes. Toll-like receptors (TLRs) represent an important group of PRRs that can sense pathogen- or microbe-associated molecular patterns. They are widely expressed in blood, spleen, lung, muscle and intestines by many types of cells, notably dendritic cells (DCs) but also macrophages, epithelial cells, and lymphocytes.

Whereas some TLRs located on the cell surface are specific for microbial lipids and proteins, others associated with endosomal compartments inside cells are specific for nucleic acids. Ligation of the TLRs by their specific ligands results in conformational changes in the receptors, leading to downstream signal transduction that primarily involves MyD88- and TRIF-dependent pathways. Except for TLR3, all other TLRs can signal through the MyD88 pathway to induce pro-inflammatory cytokines that involve activation of intracellular protein kinase cascades including IB kinase (IKK)-NF-B, and extracellular signal regulated protein kinase (ERK), c-Jun N-terminal kinase (JNK) and p38 mitogen-activation protein kinases (MAPKs). The TRIF pathway, independent of MyD88, is utilized by both TLR3 and TLR4 and mediates the induction of type I interferons.

The recombinant biotin-binding lipoproteins described herein have enhanced immunogenicity. Without wishing to be bound by a theory, lipid moieties at the N-terminals of the lipoproteins or lipopeptides contribute to the adjuvant activity. Accordingly, additional embodiments provide immunogenic or vaccine compositions for inducing an immunological response, comprising the isolated biotin-binding lipoprotein, or a suitable vector for in vivo expression thereof, or both, and a suitable carrier, as well as to methods for eliciting an immunological or protective response comprising administering to a host the isolated recombinant biotin-binding lipoprotein, the vector expressing the recombinant biotin-binding lipoprotein, or a composition containing the recombinant lipoprotein or vector, in an amount sufficient to elicit the response.

An immunological or immunogenic composition comprising the biotin-binding lipoprotein elicits an immunological response—local or systemic. The response can, but need not, be protective. It is to be noted that as used herein, the terms "immunological composition" and "immunogenic composition" include a "vaccine composition" (as the two former terms can be protective compositions). Without limitations, a lipidated biotin-binding protein described herein can be used as an antigen, adjuvant, or a co-stimulator in an immunological, immunogenic, or vaccine composition. Further, since the lipidated biotin-binding protein comprises a biotin-binding domain, the lipidated protein can be assembled to the polymer backbone of the MAPS. Accordingly, provided herein are also methods of inducing an immunological response in a host mammal. The method comprising administering to the host an immunogenic, immunological or vaccine composition comprising a lipidated biotin-binding protein described herein and a pharmaceutically acceptable carrier or diluent.

In some embodiments, the lipidated biotin-binding protein is a fusion protein comprising a lipidated biotin-binding protein and a protein or peptide.

Non-Hemolytic Hla

Hemolysins are exotoxins produced by bacteria that cause lysis of red blood cells. While highly immunogenic, their use in vaccines is limited because they cause lysis of red blood cells. Accordingly, in another aspect, provided herein are variants of staphylococcal *aureus* alpha-hemolysin (Hla), its fusion construct with biotin-binding protein and its uses. These variants, designated herein as "mHla," have substantially non-hemolytic, i.e., have substantially low hemolytic activity. As used herein, the phrase "substantially non-hemolytic" means an inability to lyse red blood cells at equivalent titers of wild-type Hla. The term "wild-type Hla" is accorded the usual definition associated with such phrase, i.e., Hla that is naturally secreted by a capable bacterial source. "Wild-type Hla," by definition, does not include, e.g., Hla fusion products derived via recombinant DNA techniques. In some embodiments, hemolytic activity of mHla is at least 5%, at least 10%, at least 15%, at least 20%, at least 20%, at least 30%, at least 30%, at least 35%, at least 40%, at least 45%, at least 50%, at least 55%, at least 60%, at least 65%, at least 70%, at least 75%, at least 80%, at least 85%, at least 90%, at least 95% lower than an equivalent titers of wild-type Hla. In some embodiments, the mHla has no detectable hemolytic activity. The inventors have also discovered that hemolytic activity of mHla can be further reduced by linking the mHla with a biotin-binding protein. Accordingly, the present disclosure also describes fusion proteins comprising a mHla protein and a biotin-binding protein.

As provided herein, a non-hemolytic Hla can be created wherein residue W205 or W213 is substituted with alanine (A) or the tripeptide DRD209-211 is substituted with a tri-alanine peptide (AAA) in the wild-type Hla. The mutated Hla protein can be expressed and purified in an *E. coli* expression system. The mutants can be made by point mutation using quick change mutagenesis. For example, the nucleotide sequence of a nucleic acid encoding the wild-type Hla can be changed to replace a given amino acid in the wild-type Hla to another amino acid.

In some embodiments, the mHla is a fusion protein comprising the mHla and a biotin-binding protein. In some embodiments, the biotin-binding mHla fusion protein comprises the amino acid sequence (SEQ ID NO: 21)
MKKIWLALAGLVLAFSASAAQDPFDASNFKDFSSIASASSSWQNQSGST

MIIQVDSFGNVSGQYVNRAQGTGCQNSPYPLTGRVNGTFIAFSVGWNNS

TENCNSATGWTGYAQVNGNNTEIVTSWNLAYEGGSGPAIEQGQDTFQYV

PTTENKSLLKDGGGGSSSADSDINIKTGTTDIGSNTTVKTGDLVTYDKE

NGMHKKVFYSFIDDKNHNKKLLVIRTKGTIAGQYRVYSEEGANKSGLAW

PSAFKVQLQLPDNEVAQISDYYPRNSIDTKEYMSTLTYGFNGNVTGDDT

-continued
GKIGGLIGANVSIGHTLKYVQPDFKTILESPTDKKVGWKVIFNNMVNQN

WGPYAAASWNPVYGNQLFMKTRNGSMKAADNFLDPNKASSLLSSGFSPD

FATVITMDRKASKQQTNIDVIYERVRDDYQLHWTSTNWKGTNTKDKWID

RSSERYKIDWEKEEMTN.

The Hla variants described herein are ligands for Toll Like Receptors (TLRs). As such, the Hla variants described herein can be used as TLR ligands. For example, the Hla variants can be used in compositions to induce TLR2 stimulation. This can be useful for inducing immunogenicity to other antigens/pathogens. Thus, the Hla variants described herein can be used in immunogenic compositions as a co-stimulation factor or adjuvant for an antigen. Further, when the mHla is fused with a biotin-binding protein, the fusion protein can be conjugated to the polymer backbone of the MAPS.

In some embodiments, the mHla can be used as a co-stimulatory factor in an immunogenic or vaccine composition.

Further, since the mHla induce an immune response in the subject, the mHla can be used as in an immunogenic or vaccine composition for vaccinating a subject against *S. aureus*.

The mHla described herein have enhanced immunogenicity. Accordingly, additional embodiments provide immunogenic or vaccine compositions for inducing an immunological response, comprising the mHla, or a suitable vector for in vivo expression thereof, or both, and a suitable carrier, as well as to methods for eliciting an immunological or protective response comprising administering to a host the isolated mHla, the vector expressing the mHla, or a composition containing the mHla or vector, in an amount sufficient to elicit the response.

An immunological or immunogenic composition comprising the mHla can elicit an immunological response— local or systemic. The response can, but need not, be protective. Accordingly, a non-hemolytic mutant of Hla described herein can be as an antigen, adjuvant, or a co-stimulator in an immunological, immunogenic, or vaccine composition.

Further, provided herein are also methods of inducing an immunological response in a host mammal. The method comprising administering to the host an immunogenic, immunological or vaccine composition comprising a non-hemolytic mutant of Hla described herein and a pharmaceutically acceptable carrier or diluent.

In another aspect, provided herein are fusion proteins comprising a biotin-binding protein described herein linked to an antigenic protein or peptide. These fusion proteins are also referred to as biotin-binding fusion proteins and as antigen fusion proteins herein. The biotin-binding protein and the antigenic protein or peptide can be linked in any configuration, e.g., biotin-binding protein can in the N-terminal and the antigenic peptide in the C-terminal of the fusion protein or vice versa.

In some embodiments, the biotin-binding protein and the antigenic protein or peptide are linked to each other by a peptide linker. Without limitations, the peptide linker can comprise any amino acid sequence and can be of any length. For example, the peptide linker sequence can be one, two, three, four, five, six, seven, eight, nine, ten, eleven, twelve, thirteen, fourteen, fifteen or more amino acids in length. In some embodiments, the peptide linker linking the antigen domain to the biotin-binding domain is eight amino-acids in length.

In some embodiments, the peptide linker linking the antigen domain to the biotin-binding domain has the amino acids sequence GGGGSSS (SEQ ID NO: 22).

In some embodiments, the antigenic protein is a non-hemolytic Hla described herein.

In some embodiments, the non-hemolytic Hla protein is a fusion protein comprising a biotin-binding protein and a non-hemolytic Hla described herein.

In some embodiments, the non-hemolytic Hla protein is a fusion protein comprising a lipidated biotin-binding protein and a non-hemolytic Hla described herein.

Immunogenic Compositions

In another aspect, provided herein are immunogenic compositions comprising an antigen fusion protein, a lipidated biotin-binding, or a non-hemolytic variant of Hla described herein. In addition, provided herein are also immunogenic compositions and vaccine compositions comprising an immunogenic complex that comprises at least one antigen fusion protein, or multiple antigen fusion proteins, attached to a polymer scaffold for use in eliciting an immune response to each of the antigens attached to the polymer, and optionally to the polymer itself, when administered to a subject. Without wishing to be bound by a theory, the immunogenic composition described herein stimulates a humoral and cellular immune response: it can generate antibody and the Th1/Th17 responses to multiple protein antigens using a single MAPS immunogenic construct. A combination of B- and T-cell immunity to the organism represents an optimal vaccine strategy against many diseases, including pneumococcal disease associated invasive infection and nasopharyngeal carriage. In some embodiments, the immunogenic composition is a vaccine or is included in a vaccine.

Accordingly, the embodiments herein provide for an immunogenic composition and methods useful for raising an immune response in a subject, which can be used on its own or in conjunction or admixture with essentially any existing vaccine approaches.

In some embodiments, an immunogenic composition as disclosed herein comprises at least 2 antigens, or at 3 least antigens, or at least 5 antigens, or between 2-10 antigens, or between 10-15 antigens, or between 15-20 antigens, or between 20-50 antigens, or between 50-100 antigens, or more than 100 antigens, inclusive. In some embodiments, where an immunogenic composition as disclosed herein comprises at least 2 antigens, the antigens can be the same antigen or at least 2 different antigens. In some embodiments, the antigens can be from the same or different pathogens, or can be different epitopes or parts of the same antigenic protein, or can be the same antigen which is specific to different serotypes or seasonal variations of the same pathogen (e.g., influenza virus A, B, and C).

In some embodiments, an immunogenic composition as disclosed herein comprises an antigen from a pathogenic organism or an abnormal tissue. In some embodiments, the antigen is a tumor antigen. In some embodiments, an antigen can be at least one antigen selected from antigens of pathogens or parasites, such as antigens of *Streptococcus pneumoniae, Mycobacterium tuberculosis* or *M. tetanus, Bacillus anthracis*, HIV, seasonal or epidemic influenza antigens (such as H1N1 or H5N1), *Bordetella pertussis, Staphylococcus aureus, Neisseria meningitides* or *N. gonorrhoeae*, HPV, *Chlamydia trachomatis*, HSV or other herpes viruses, or Plasmodia sp. These antigens may include peptides, proteins, glycoproteins, or polysaccharides. In some embodiments, the antigen is a toxoid or portion of a toxin.

In some embodiments, an immunogenic composition as disclosed herein comprises an antigenic polysaccharide, for example, such as Vi antigen (*Salmonella typhi* capsular polysaccharide), pneumococcal capsular polysaccharides, pneumococcal cell wall polysaccharide, Hib (*Haemophilus influenzae* type B) capsular polysaccharide, meningococcal capsular polysaccharides, and other bacterial capsular or cell wall polysaccharides, or any combinations thereof. The polysaccharide may have a protein component, e.g., a glycoprotein such as those from viruses.

In some embodiments, an immunogenic composition as disclosed herein further comprises at least one co-stimulation factor associated with the polymer or polysaccharide, where the co-stimulation factor can be associated directly or indirectly. For example, in some embodiment, a co-stimulation factor can be covalently attached to the polymer. For example, in some embodiments, a co-stimulation factor can be covalently attached to the first affinity molecule, which is then cross-linked to the polymer. For example, in some embodiments, a co-stimulation factor can be attached to a complementary affinity molecule, which associates with a first affinity molecule to link the co-stimulator factor to the polymer. In some embodiments, a co-stimulation factor is an adjuvant. In alternative embodiments, a co-stimulatory factor can be any known to one of ordinary skill in the art, and includes any combination, for example, without limitation, Toll like receptor agonists (agonists for TLR2, 3, 4, 5 7, 8, 9, etc.), NOD agonists, or agonists of the inflammasome.

In some embodiments, the co-stimulatory factor can be a lipidated biotin-binding protein or a non-hemolytic variant of alpha-hemolysin or the fusion protein of mHla with biotin-binding protein described herein.

Another aspect of the present invention relates to the use of the immunogenic composition as disclosed herein to be administered to a subject to elicit an immune response in the subject. In some embodiments, the immune response is an antibody/B cell response, a $CD4^+$ T-cell response (including Th1, Th2 and Th17 cells) and/or a $CD8^+$ T-cell response. In some embodiments, at least one adjuvant is administered in conjunction with the immunogenic composition.

Another aspect of the present invention relates to a method for inducing an immune response in a subject to at least one antigen, comprising administering to the subject the immunogenic composition as disclosed herein.

Another aspect of the present invention relates to a method of vaccinating an animal, e.g., a bird, a mammal or a human, against at least one antigen comprising administering a vaccine composition comprising the immunogenic composition as disclosed herein.

In all aspects as disclosed herein, an animal or a subject can be a human. In some embodiments, the subject can be an agricultural or non-domestic animal, or a domestic animal. In some embodiments, a vaccine composition comprising the immunogenic composition as disclosed herein can be administered via subcutaneous, intranasal, oral, sublingual, vaginal, rectal, intradermal, intraperitoneal, or intra muscular injection.

In all aspects as disclosed herein, an immune response is an antibody/B-cell response, a $CD4^+$ T-cell response (including Th1, Th2 and Th17 responses) or a CD8+ T-cell response against protein/peptide antigen(s). In some embodiments, an immune response is an antibody/B-cell response against the polymer, e.g., a pneumococcal polysaccharide. In some embodiments, at least one adjuvant is administered in conjunction with the immunogenic composition.

Another aspect of the present invention relates to the use of the immunogenic composition as disclosed herein for use in a diagnostic for exposure to a pathogen or immunogenic agent.

Multiple Antigen Presenting System

Also provided herein is also an immunogenic multiple antigen presenting system (MAPS), useful for the production of immunogenic compositions, such as those useful in vaccines. In particular, the present invention relates to compositions comprising an immunogenic complex comprising at least one type of polymer, e.g., a polysaccharide, that can, optionally, be antigenic; at least one antigenic protein or peptide; and at least one complementary affinity-molecule pair comprising (i) a first affinity molecule that associates with the polymer, and (ii) a complementary affinity molecule that associates with the protein or peptide; such that the first and complementary affinity molecules serve as an indirect link between the polymer with the antigenic protein or peptide. Accordingly, the polymer can attach at least 1, or at least 2, or a plurality of the same or different protein or peptide antigens. In some embodiments, the polymer is antigenic, e.g., the polymer is a pneumococcal capsular polysaccharide. In some embodiments, the protein or peptide antigens are recombinant protein or peptide antigens.

The immunogenic compositions as disclosed herein can elicit both humoral and cellular responses to one or multiple antigens at the same time. The immunogenic compositions provide for a long-lasting memory response, potentially protecting a subject from future infection. This allows for a single immunogenic composition that raises a high titer of functional anti-polysaccharide antibody, and is similar or compares favorably with the antibody level induced by conventional conjugate vaccine. Moreover, there is no restriction to specific carrier protein, and various antigen proteins can be used in MAPS construct to generate a robust anti-polysaccharide antibody response.

Additionally, the strong antibody response and Th17/Th1 responses are specific to multiple protein antigens presented via the MAPS composition. This presents a major advantage, as a means for eliciting two forms of immunity with one construct. In addition to a more conventional immune response to an antigenic polysaccharide conjugated to a protein carrier, the present invention provides for a T-cell response and, more specifically, Th17 and Th1 responses to proteins injected systemically. Moreover, the present immunogenic composition can incorporate ligands onto the polymer backbone. This provides a potential to enhance specific B-cell or T-cell responses by modifying protein/polymer ratio, complex size, or by incorporating specific co-stimulatory factor, such as TLR2/4 ligands, etc., into the composition.

Compared with typical conjugation technology, which involves harsh treatment of proteins, the present methods avoid risk of denaturation of other modification of the peptide antigen. This provides a substantial advantage of preserving the antigenicity of the included proteins and increases the probability that the protein itself will serve as an antigen (rather than just a carrier). Similarly, the present methods avoid unnecessary modification/damage of the polysaccharide backbone, because there is no heavy chemical cross-linking: biotinylation can be precisely controlled to react with specific functional groups of the polysaccharide, and the biotinylation level can be easily adjusted. This is advantageous in avoiding the typical process of conjugation, that results in damage to critical side chains or epitopes, which may cause reduced immunogenicity and protection.

The present the affinity-based assembly provides easy and highly flexible preparation of the immunogenic composition. It is highly specific and stable; it can remain in the cold for months and retain its potency. The assembly process is simple enough to ensure high reproducibility; there are only a few steps required, which reduces the risk of lot-to-lot variation, of great industrial advantage. The MAPS assembly is highly efficient (over 95%), even at low concentrations of protein and polysaccharide (such as 0.1 mg/ml); this is a major advantage, because inefficiencies in conjugate manufacture (typically efficiencies are in the <50% range) represent a major hurdle and reason for the high cost of vaccines. For formulation: it is easy to adjust the composition and physical properties of the final product. The protein:polymer ratio in the complex is adjustable; with moderate biotinylation of polymer, protein:polymer can be 10:1 (w/w) or more; conversely, the ratio can be 1:10 or less if such is the interest based on immunological goals. Additionally, the size of the immunogenic MAPS composition can be adjusted by the choice of polymer size. The methods of making the MAPS provide for ease in combining proteins and polymers with little modification. The possible multivalency of final product by loading multiple protein antigens, from the same or different pathogens (e.g., pneumococcus and tuberculosis), in single immunogenic construct, provides for a composition that can be used to decrease the number of vaccines required to immunize a subject against more than one disease. Moreover, the MAPS composition is highly stable; becoming dissociated only upon boiling and maintaining immunogenicity even after many months at 4° C. The immunogenicity of the MAPS complex may be limited by the stability of the antigenic protein or peptide component, which stability may be extended by inclusion in the MAPS complex. The specific antigens used herein exhibited stability at room temperature and after at least one freeze-thaw cycle. This provides an important advantage over current vaccines that are compromised if the "cold chain" is not maintained carefully.

Accordingly, one aspect of the present invention relates to an immunogenic composition comprising a polymer, at least one protein or peptide antigen, and at least one complementary affinity-molecule pair, where the complementary affinity-molecule pair comprises a first affinity molecule that associates with the polymer and a complementary affinity molecule that associates with the protein or peptide antigen, so that when the first affinity molecule associates with the complementary affinity molecule, it indirectly links the antigen to the polymer.

In some embodiments, the first affinity molecule is cross-linked to the polymer with a cross-linking reagent, for example, a cross-linking reagent selected from CDAP(1-cyano-4-dimethylaminopyridinium tetrafluoroborate), EDC (1-Ethyl-3-[3-dimethylaminopropyl] carbodiimide hydrochloride), sodium cyanoborohydride; cyanogen bromide; or ammonium bicarbonate/iodoacetic acid. In some embodiments, the first affinity molecule is cross-linked to carboxyl, hydroxyl, amino, phenoxyl, hemiacetal, and mecapto functional groups of the polymer. In some embodiments, the first affinity molecule is covalently bonded to the polymer.

In some embodiments, the first affinity molecule is biotin or a derivative thereof, or a molecule with similar structure or physical property as biotin, for example, an amine-PEG3-biotin ((+)-biotinylation-3-6,9-trixaundecanediamine) or derivative thereof.

In some embodiments, the protein or peptide antigen of the immunogenic composition is a fusion protein comprising the antigenic protein or peptide fused to the complementary affinity binding molecule. The fusion can be a genetic construct, i.e., a recombinant fusion peptide or protein. In some embodiments, an antigen can be covalently attached as a fusion protein to the complementary affinity molecule. In alternative embodiments, the antigen is non-covalently attached to the complementary affinity molecule.

In some embodiments, the complementary affinity molecule is a biotin-binding protein or a derivative or a functional portion thereof. In some embodiments, a complementary affinity molecule is an avidin-like protein or a derivative or a functional portion thereof, for example but not limited to, rhizavidin or a derivative thereof. In some embodiments, a complementary affinity molecule is avidin or streptavidin or a derivative or a functional portion thereof.

In some embodiments, a secretion signal peptide is located at the N-terminus of the avidin-like protein. Any signal sequence known to persons of ordinary skill in the art can be used; and in some embodiments, the signal sequence is MKKIWLALAGLVLAFSASA (SEQ ID NO: 2) or a derivative or functional portion thereof. In some embodiments, the antigen can be fused to a complementary affinity molecule via a flexible linker peptide, where the flexible linker peptide attaches the antigen to the complementary affinity molecule.

In some embodiments, the polymer component of the immunogen comprises a polymer derived from a living organism, e.g., a polysaccharide. In some embodiments, a polymer can be purified and isolated from a natural source, or is can be synthesized as with a natural composition/structure, or it can be a synthetic (e.g., with an artificial composition/structure) polymer. In some embodiments, a polymer is derived from an organism selected from the group consisting of: bacteria, archaea, or eukaryotic cells like fungi, insect, plant, or chimeras thereof. In some embodiments, the polymer is a polysaccharide derived from a pathogenic bacterium. In specific embodiments the polysaccharide is a pneumococcal capsular polysaccharide, a pneumococcal cell-wall polysaccharide, or a *Salmonella typhi* Vi polysaccharide.

In some embodiments, a polymer of the immunogenic composition as disclosed herein is branched chain polymer, e.g., a branched polysaccharide, or alternatively, can be a straight chain polymer, e.g., a single chain polymer, e.g., polysaccharide. In some embodiments, the polymer is a polysaccharide, for example, dextran or a derivative thereof. In some embodiments, a polymer, e.g., dextran polysaccharide can be of average molecular weight of 425 kD-500 kDa, inclusive, or in some embodiments, greater than 500 kDa. In some embodiments, a polymer, e.g., dextran polysaccharide can be of average molecular weight of 60 kD-90 kDa, inclusive, or in some embodiments, smaller than 70 kDa. The dextran polymer can be derived from a bacterium, such as *Leuconostoc mesenteroides*.

In some embodiments, an immunogenic composition as disclosed herein comprises at least 2 antigens, or at 3 least antigens, or at least 5 antigens, or between 2-10 antigens, or between 10-15 antigens, or between 15-20 antigens, or between 20-50 antigens, or between 50-100 antigens, or more than 100 antigens, inclusive. In some embodiments, where an immunogenic composition as disclosed herein comprises at least 2 antigens, the antigens can be the same antigen or at least 2 different antigens. In some embodiments, the antigens can be from the same or different pathogens, or can be different epitopes or parts of the same antigenic protein, or can be the same antigen which is specific to different serotypes or seasonal variations of the same pathogen (e.g., influenza virus A, B, and C).

In some embodiments, an immunogenic composition as disclosed herein comprises an antigen from a pathogenic organism or an abnormal tissue. In some embodiments, the antigen is a tumor antigen. In some embodiments, an antigen can be at least one antigen selected from antigens of pathogens or parasites, such as antigens of *Streptococcus pneumoniae, Mycobacterium tuberculosis* or *M. tetanus, Bacillus anthracis*, HIV, seasonal or epidemic influenza antigens (such as H1N1 or H5N1), *Bordetella pertussis, Staphylococcus aureus, Neisseria meningitides* or *N. gonorrhoeae*, HPV, *Chlamydia trachomatis*, HSV or other herpes viruses, or Plasmodia sp. These antigens may include peptides, proteins, glycoproteins, or polysaccharides. In some embodiments, the antigen is a toxoid or portion of a toxin.

In some embodiments, an immunogenic composition as disclosed herein comprises an antigenic polysaccharide, for example, such as Vi antigen (*Salmonella typhi* capsular polysaccharide), pneumococcal capsular polysaccharides, pneumococcal cell wall polysaccharide, Hib (*Haemophilus influenzae* type B) capsular polysaccharide, meningococcal capsular polysaccharides, the polysaccharide of *Bacillus anthracis* (the causative agent of anthrax), and other bacterial capsular or cell wall polysaccharides, or any combinations thereof. The polysaccharide may have a protein component, e.g., a glycoprotein such as those from viruses.

In some embodiments, an immunogenic composition as disclosed herein further comprises at least one co-stimulation factor associated with the polymer or polysaccharide, where the co-stimulation factor can be associated directly or indirectly. For example, in some embodiment, a co-stimulation factor can be covalently attached to the polymer. For example, in some embodiments, a co-stimulation factor can be covalently attached to the first affinity molecule, which is then cross-linked to the polymer. For example, in some embodiments, a co-stimulation factor can be attached to a complementary affinity molecule, which associates with a first affinity molecule to link the co-stimulation factor to the polymer. In some embodiments, a co-stimulation factor is an adjuvant. In alternative embodiments, a co-stimulatory factor can be any known to one of ordinary skill in the art, and includes any combination, for example, without limitation, Toll like receptor agonists (agonists for TLR2, 3, 4, 5 7,8, 9, etc.), NOD agonists, or agonists of the inflammasome.

Another aspect of the present invention relates to the use of the immunogenic composition as disclosed herein to be administered to a subject to elicit an immune response in the subject. In some embodiments, the immune response is an antibody/B cell response, a $CD4^+$ T-cell response (including Th1, Th2 and Th17 cells) and/or a $CD8^+$ T-cell response. In some embodiments, at least one adjuvant is administered in conjunction with the immunogenic composition.

Another aspect of the present invention relates to a method for inducing an immune response in a subject to at least one antigen, comprising administering to the subject the immunogenic composition as disclosed herein.

Another aspect of the present invention relates to a method of vaccinating an animal, e.g., a bird, a mammal or a human, against at least one antigen comprising administering a vaccine composition comprising the immunogenic composition as disclosed herein.

In all aspects as disclosed herein, an animal or a subject can be a human. In some embodiments, the subject can be an agricultural or non-domestic animal, or a domestic animal. In some embodiments, a vaccine composition comprising the immunogenic composition as disclosed herein can be administered via subcutaneous, intranasal, oral, sublingual, vaginal, rectal, intradermal, intraperitoneal, intra muscular injection, or via skin-patch for transcutaneous immunization.

In all aspects as disclosed herein, an immune response is an antibody/B-cell response, a $CD4^+$ T-cell response (including Th1, Th2 and Th17 responses) or a CD8+ T-cell response against protein/peptide antigen(s). In some embodiments, an immune response is an antibody/B-cell response against the polymer, e.g., a pneumococcal polysaccharide. In some embodiments, at least one adjuvant is administered in conjunction with the immunogenic composition.

Another aspect of the present invention relates to the use of the immunogenic composition as disclosed herein for use in a diagnostic for exposure to a pathogen or immunogenic agent.

Provided herein also is a method of vaccinating a subject, e.g., a mammal, e.g., a human with the immunogenic compositions as disclosed herein, the method comprising administering a vaccine composition as disclosed herein to the subject.

Generally, the immunogenic compositions and compositions comprising an immunogenic complex can comprise at least one antigen, or multiple antigens, attached to a polymer scaffold for use in eliciting an immune response to each of the antigens attached to the polymer, and optionally to the polymer itself, when administered to a subject. This multiple antigen presenting system (MAPS), stimulates a humoral and cellular immune response: it can generate anti-polysaccharide antibody and the B-cell/Th1/Th17 responses to multiple protein antigens using single MAPS immunogenic construct. A combination of B- and T-cell immunity to the organism might represent an optimal vaccine strategy against many diseases, including pneumococcal disease associated invasive infection and nasopharyngeal carriage. In some embodiments, the immunogenic composition is a vaccine or is included in a vaccine.

Accordingly, one aspect of the present invention relates to an immunogenic composition (multiple antigen presenting system, or MAPS) comprising at least one polymer, e.g., one polysaccharide, at least one protein or peptide antigen, and at least one complementary affinity-molecule pair comprising (i) a first affinity molecule associated with the polymer, and (ii) a complementary affinity molecule associated with the antigen, which serves to indirectly attach the antigen to the polymer (e.g., the first affinity molecule associates with the complementary affinity molecule to link the antigen to the polymer). Accordingly, as the polymer can be used as a scaffold to attach at least 1, or at least 2, or a more (e.g., a plurality) of the same or different antigens. The immunogenic compositions as disclosed herein can be used to elicit both humoral and cellular immunity to multiple antigens at the same time.

Accordingly, the embodiments herein provide for an immunogenic composition and methods useful for raising an immune response in a subject, which can be used on its own or in conjunction or admixture with essentially any existing vaccine approaches.

Figure 15:
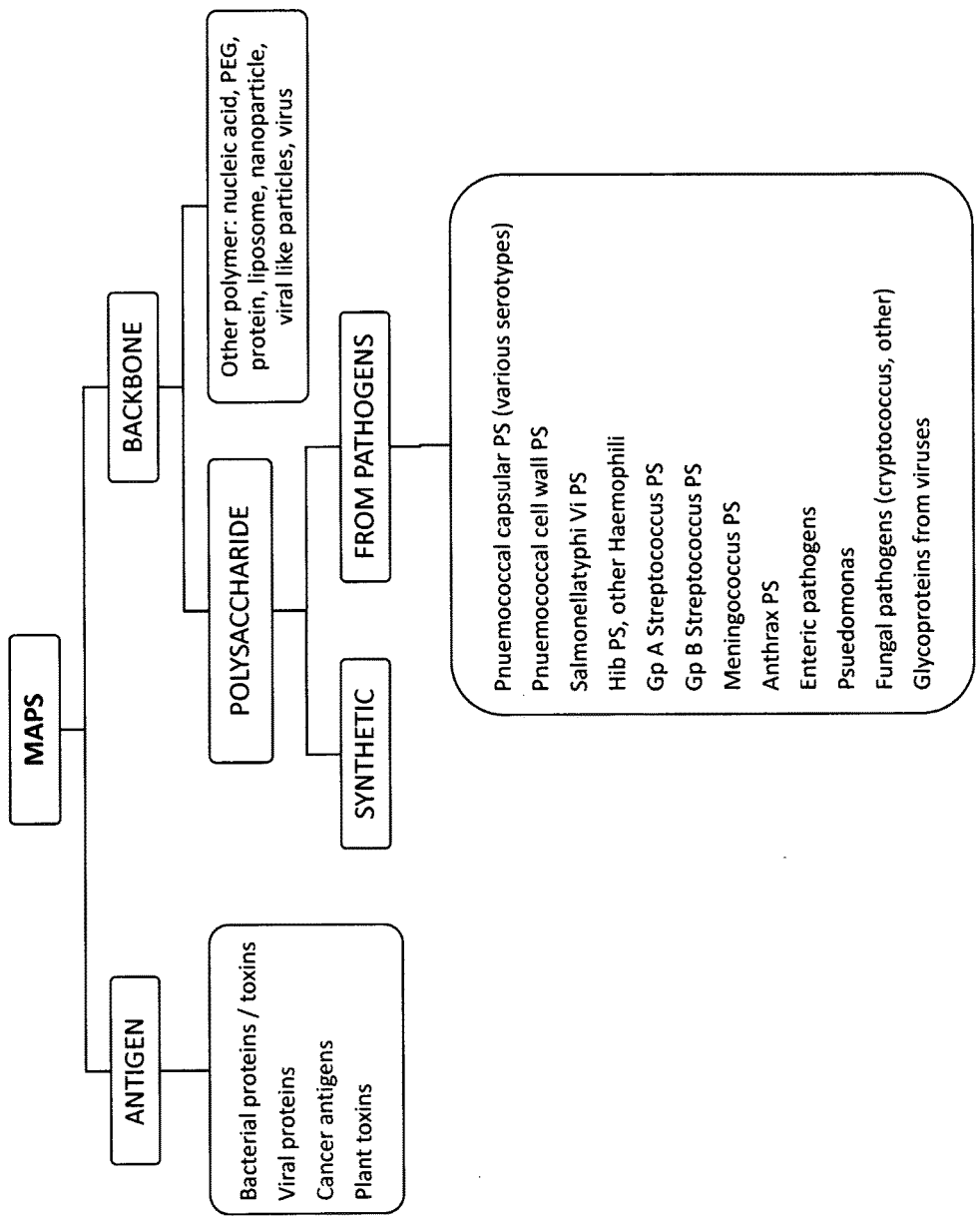
FIG. 15 shows a hierarchal schematic table and showing a variety of different embodiments of the MAPS platform, showing that the MAPS composition can be designed and manufactured to elicit a particular, broad spectrum, or variety of antigenic targets.

The MAPS is a flexible and versatile composition that can be designed and manufactured to elicit a particular, broad spectrum, or variety of antigenic targets. FIG. 15 is a hierarchal schematic and provides a simple example guide for envisioning the flexibility of MAPS embodiments.

Polymers

One component of MAP consists of a "backbone," typically a polymer. The polymer may be antigenic or non-antigenic. It can be made of a wide variety on substances, as described herein, with the caveat that the polymer serves as a means of presenting the associated antigen(s) to the immune system in immunogenic fashion. In some embodiments, the polymer is a synthetic polymer. In some embodiments, the polymer is a naturally occurring polymer, e.g., a polysaccharide derived or purified from bacterial cells. In some embodiments, the polysaccharide is derived or purified from eukaryotic cells, e.g., fungi, insect or plant cells. In yet other embodiments, the polymer is derived from mammalian cells, such as virus-infected cells or cancer cells. In general, such polymers are well known in the art and are encompassed for use in the methods and compositions as disclosed herein.

In some embodiments, a polymer is a polysaccharide selected from any of the following, dextran, Vi polysaccharide of *Salmonella typhi*, pneumococcal capsular polysaccharide, pneumococcal cell wall polysaccharide (CWPS), meningococcal polysaccharide, *Haemophilus influenzae* type b polysaccharide, or any another polysaccharide of viral, prokaryotic, or eukaryotic origin.

In some embodiments, the polysaccharide consists of or comprises an antigenic sugar moiety. For example, in some embodiments, a polysaccharide for use in the methods and immunogenic compositions as disclosed herein is a Vi polysaccharide of *Salmonella typhi*. The Vi capsular polysaccharide has been developed against bacterial enteric infections, such as typhoid fever. Robbins et al., 150 J. Infect. Dis. 436 (1984); Levine et al., 7 Baillieres Clin. Gastroenterol. 501 (1993). Vi is a polymer of $\alpha$-1$\rightarrow$4-galacturonic acid with an N acetyl at position C-2 and variable 0-acetylation at C-3. The virulence of *S. typhi* correlates with the expression of this molecule. Sharma et al., 101 PNAS 17492 (2004). The Vi polysaccharide vaccine of *S. typhi* has several advantages: Side effects are infrequent and mild, a single dose yields consistent immunogenicity and efficacy. Vi polysaccharide may be reliably standardized by physicochemical methods verified for other polysaccharide vaccines, Vi is stable at room temperature and it may be administered simultaneously with other vaccines without affecting immunogenicity and tolerability. Azze et al., 21 Vaccine 2758 (2003).

Thus, the Vi polysaccharide of *S. typhi* may be cross-linked to a first affinity molecule as disclosed herein, for attaching at least one antigen to the polysaccharide. In some embodiments, the antigen can be from the same or from another organism, such that the resulting immunogenic composition confers at least some level of immunity against one pathogen, or two different pathogens: if the antigen confers protection against pneumococcus, an immunogenic composition where the polymer scaffold is a Vi polysaccharide can raise an immunogenic response against both *S. typhi* and pneumococci. Other examples include combining sugars from encapsulated bacteria (such as meningococcus, *S. aureus*, pneumococcus, Hib, etc.) and tuberculosis antigens, to provide an immunogenic composition that raises an immune reponse against two different pathogens.

Other polysaccharide (PS) moieties that may be used in the present invention in alternative to dextran, bacterial cell wall polysaccharides (CWPS), etc., include carbohydrate antigens of cancers.

Further in regard to pneumococcal polysaccharides, the polysaccharide can be derived from any of the over 93 serotypes of pneumococcus that have been identified to date, for example, including but not limited to serotypes 1, 2, 3, 4, 5, 6A, 6B, 6C, 6D, 7F, 8, 9N, 9V, 10A, 11A, 12F, 14, 15B, 17F, 18C, 19A, 19F, 20, 22F, 23F, and 33F. Additional serotypes may be identified and included in the present immunogenic composition as described herein. More than one pneumococcal polysaccharide can be included as the polymer backbone of the present immunogenic compositions or in a vaccine comprising the present MAPS compositions.

The polysaccharide can also be derived from the invention, the immunogenic composition comprises *N. meningitidis* capsular polysaccharides from at least one, two, three or four of the serogroups A, C, W, W135, or Y.

A further embodiment comprises the Type 5, Type 8, or any of the polysaccharides or oligosaccharides of *Staphylococcus aureus*.

In some embodiments, the polymer is chimeric polymer comprising more than one type of polymer. For example a polymer of the immunogenic composition as disclosed herein can comprise a portion of polymer A, and the remaining portion of polymer B. There is no limit to the amount of different types of polymers which can be used in a single MAPS backbone entity. In some embodiments, where the polymer is a branched polymer, the chain polymer can be polymer A, and the branches can be at least 1 or at least 2 or at least 3 or more different polymers.

In some embodiments, the polymer is a branched polymer. In some embodiments, the polymer is a single chain polymer.

In some embodiments, the polymer is a polysaccharide comprising at least 10 carbohydrate repeating units, or at least 20, or at least 50, or at least 75, or at least 100, or at least 150, or at least 200, or at least 250, or at least 300, or at least 350, or at least 400, or at least 450, or at least 500, or more than 500 repeating units, inclusive.

In one aspect of the invention, the polysaccharide (PS) can have a molecular mass of <500 kDa or >500 kDa. In another aspect of the invention, the PS has a molecular mass of <70 kDa.

In some embodiments, a polymer is a large molecular weight polymer, e.g., a polymer can be of an average molecular weight of between about 425-500 kDa, inclusive, for example, at least 300 kDa, or at least 350 kDa, or at least 400 kDa, or at least 425 kDa, or at least 450 kDa, or at least 500 kDa or greater than 500 kDa, inclusive, but typically less than 500 kDa.

In some embodiments, a polymer can be a small molecular weight polymer, e.g., a polymer can be of an average molecular weight of between about 60 kDA to about 90 kDa, for example, at least 50 kDa, or at least 60 kDa, or at least 70 kDa, or at least 80 kDa, or at least 90 kDa, or at least 100 kDa, or greater than 100 kDa, inclusive, but generally less than about 120 kDa.

In some embodiments, the polymer is harvested and purified from a natural source; and in other embodiments, the polymer is synthetic. Methods to produce synthetic polymers, including synthetic polysaccharides, are known to persons of ordinary skill and are encompassed in the compositions and methods as disclosed herein.

Just a few of the polysaccharide polymers that can serve as a backbone for one or more antigens or antigen types are exemplified in Table 1:

TABLE 1

Example polysaccharide polymer MAPS backbone and associated example antigens

| Polysaccharide | | Protein Antigens | |
| --- | --- | --- | --- |
| | | Number of antigens | Antigen origins |
| Dextran | D90 (60-90 KD) | two | pneumococcus |
| | D150 (150 KD) | three | pneumococcus |
| | D270 (270 KD) | three | pneumococcus |
| | D500 (425-575 KD) | two; three; six | pneumococcus |
| Pneumococcal capsular polysaccharide | Serotype 1 | one, two, three, five | pneumococcus, tuberculosis, staphylococcus |
| | Serotype 3 | five | pneumococcus, tuberculosis |
| | Serotype 5 | one; two; three; five | pneumococcus, tuberculosis |
| | Serotype 6B | two | pneumococcus |
| | Serotype 7 | three | pneumococcus |
| | Serotype 14 | one; two; three; five | pneumococcus, tuberculosis |
| | Serotype 19 | three | pneumococcus |
| Pneumococcal cell wall polysaccharide | | five | pneumococcus |
| *S. typhi* Vi polysaccharide | | five | pneumococcus |

Additional polymers that can be used in the immunogenic MAPS compositions described herein include polyethylene glycol-based polymers, poly(ortho ester) polymers, polyacryl carriers, PLGA, polyethylenimine (PEI), polyamidoamine (PAMAM) dendrimers, β-amino ester polymers, polyphosphoester (PPE), liposomes, polymerosomes, nucleic acids, phosphorothioated oligonucleotides, chitosan, silk, polymeric micelles, protein polymers, virus particles, virus-like-particles (VLPs) or other micro-particles. See, e.g., El-Sayed et al., *Smart Polymer Carriers for Enhanced Intracellular Delivery of Therapeutic Molecules*, 5 Exp. Op. Biol. Therapy, 23 (2005). Biocompatible polymers developed for nucleic acid delivery may be adapted for use as a backbone herein. See, e.g., BIOCOMPATIBLE POL. NUCL. ACID. DELIV. (Domb et al., eds., John Wiley & Sons, Inc. Hoboken, N.J., 2011).

For example, VLPs resemble viruses, but are non-infectious because they do not contain any viral genetic material. The expression, including recombinant expression, of viral structural proteins, such as envelope or capsid components, can result in the self-assembly of VLPs. VLPs have been produced from components of a wide variety of virus families including Parvoviridae (e.g., adeno-associated virus), Retroviridae (e.g., HIV), and Flaviviridae (e.g., Hepatitis B or C viruses). VLPs can be produced in a variety of cell culture systems including mammalian cell lines, insect cell lines, yeast, and plant cells. Recombinant VLPs are particularly advantageous because the viral component can be fused to recombinant antigens as described herein.

Antigens

The fusion proteins and immunogenic compositions as disclosed herein can comprise any antigen that elicits an immune response in a subject. In some embodiments, at least one or more antigens are associated with the polymer of the composition. In some embodiments, at least 2, or at least 3, or at least 5, or at least 10, or at least 15, or at least 20, or at least 50, or at least 100, or more than 100 antigens can be associated with the polymer as disclosed herein. In some embodiments, where the immunogenic composition comprises more than one antigen, the antigens can be the same antigen or they can be a variety of different antigens associated with the polymer. In some embodiments, where the immunogenic composition comprises more than one antigen, the antigens can be antigens from the same pathogen or from different pathogens, or alternatively, can be different antigens from the same pathogen, or similar antigens from different serotypes of pathogens.

An antigen for use in the fusion proteins and immunogenic compositions and methods described herein can be any antigen, including, but not limited to pathogenic peptides, toxins, toxoids, subunits thereof, or combinations thereof (e.g., cholera toxin, tetanus toxoid).

In some embodiments, an antigen, which can be fused to the complementary affinity molecule, can be any antigen associated with an infectious disease, or cancer or immune disease. In some embodiments, an antigen can be an antigen expressed by any of a variety of infectious agents, including virus, bacterium, fungus or parasite.

In some embodiments, an antigen is derived (e.g., obtained) from a pathogenic organism. In some embodiments, the antigen is a cancer or tumor antigen, e.g., an antigen derived from a tumor or cancer cell.

In some embodiments, an antigen derived from a pathogenic organism is an antigen associated with an infectious disease; it can be derived from any of a variety of infectious agents, including virus, bacterium, fungus or parasite.

In some embodiments, a target antigen is any antigen associated with a pathology, for example an infectious disease or pathogen, or cancer or an immune disease such as an autoimmune disease. In some embodiments, an antigen can be expressed by any of a variety of infectious agents, including virus, bacterium, fungus or parasite. A target antigen for use in the methods and compositions as disclosed herein can also include, for example, pathogenic peptides, toxins, toxoids, subunits thereof, or combinations thereof (e.g., cholera toxin, tetanus toxoid).

Non-limiting examples of infectious viruses include: Retroviridae; Picornaviridae (for example, polio viruses, hepatitis A virus; enteroviruses, human coxsackie viruses, rhinoviruses, echoviruses); Calciviridae (such as strains that cause gastroenteritis); Togaviridae (for example, equine encephalitis viruses, rubella viruses); Flaviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bungaviridae (for example, Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papoviridae (papilloma viruses, polyoma viruses); Adenoviridae (most adenoviruses); Herpesviridae (herpes simplex virus (HSV) 1 and HSV-2, varicella zoster virus, cytomegalovirus (CMV), Marek's disease virus, herpes viruses); Poxviridae (variola viruses, vaccinia viruses, pox viruses); and Iridoviridae (such as African swine fever virus); and unclassified viruses (for example, the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses). The compositions and methods described herein are contemplated for use in treating infections with these viral agents.

Examples of fungal infections that may be addressed by inclusion of antigens in the present embodiments include aspergillosis; thrush (caused by *Candida albicans*); cryptococcosis (caused by *Cryptococcus*); and histoplasmosis. Thus, examples of infectious fungi include, but are not limited to, *Cryptococcus neoformans, Histoplasma capsulatum, Coccidioides immitis, Blastomyces dermatitidis, Chlamydia trachomatis, Candida albicans*. Components of these organisms can be included as antigens in the MAPS described herein.

In one aspect of the invention, an antigen is derived from an infectious microbe such as *Bordatella pertussis, Brucella, Enterococci* sp., *Neisseria meningitidis, Neisseria gonorrheae, Moraxella*, typeable or nontypeable *Haemophilus, Pseudomonas, Salmonella, Shigella, Enterobacter, Citrobacter, Klebsiella, E. coli, Helicobacter pylori, Clostridia, Bacteroides, Chlamydiaceae, Vibrio cholera, Mycoplasma, Treponemes, Borelia burgdorferi, Legionella pneumophilia, Mycobacteria* sps (such as *M. tuberculosis, M avium, M. intracellulare*, M. kansaii, *M. gordonae, M. leprae*), *Staphylococcus aureus, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Leptospira* sps., *Pasteurella multocida, Bacteroides* sp., *Fusobacterium nucleatum, Streptobacillus moniliformis, Treponema pallidium, Treponema pertenue*, and *Actinomyces israelii*. The compositions and methods described herein are contemplated for use in treating or preventing infections against these bacterial agents.

Additional parasite pathogens from which antigens can be derived include, for example: *Entamoeba histolytica, Plasmodium falciparum, Leishmania* sp., *Toxoplasma gondii, Rickettsia*, and the *Helminths*.

In another aspect of the invention, an antigen is a truncated pneumococcal PsaA protein, pneumolysin toxoid pneumococcal serine/threonine protein kinase (StkP), pneumococcal serine/threonine protein kinase repeating unit (StkPR), pneumococcal PcsB protein, staphylococcal alpha hemolysin, *Mycobacterium tuberculosis* mtb protein ESAT-6, *M. tuberculosis* cell wall core antigen, *Chlamydia* CT144, CT242 or CT812 polypeptides or fragments of these, *Chlamydia* DNA gyrase subunit B, *Chlamydia* sulfite synthesis/biphosphate phosphatase, *Chlamydia* cell division protein FtsY, *Chlamydia* methionyl-tRNA synthetase, *Chlamydia* DNA helicase (uvrD), *Chlamydia* ATP synthase subunit I (atpI), or *Chlamydia* metal dependent hydrolase.

An embodiment of the present invention provides for an immunogenic composition targeting the pathogen *Myocobacterium tuberculosis* (TB), an intracellular bacterial parasite. One example of a TB antigen is TbH9 (also known as Mtb 39A). Other TB antigens include, but are not limited to, DPV (also known as Mtb8.4), 381, Mtb41, Mtb40, Mtb32A, Mtb64, Mtb83, Mtb9.9A, Mtb9.8, Mtb16, Mtb72f, Mtb59f, Mtb88f, Mtb71f, Mtb46f and Mtb31f, wherein "f" indicates that it is a fusion or two or more proteins.

As noted above, an antigen can be derived from a *Chlamydia* species for use in the immunogenic compositions of the present invention. *Chlamydiaceae* (consisting of *Chlamydiae* and *Chlamydophila*), are obligate intracellular gram-negative bacteria. *Chlamydia trachomatis* infections are among the most prevalent bacterial sexually transmitted infections, and perhaps 89 million new cases of genital chlamydial infection occur each year. The *Chlamydia* of the present invention include, for example, *C. trachomatis, Chlamydophila pneumoniae, C. muridarum, C. suis, Chlamydophila abortus, Chlamydophila psittaci, Chlamydophila caviae, Chlamydophila fells, Chlamydophila pecorum*, and *C. pneumoniae*. Animal models of chlamydial infection have established that T-cells play a critical role both in the clearance of the initial infection and in protection from re-infection of susceptible hosts. Hence, the immunogenic compositions as disclosed herein can be used to provide particular value by eliciting cellular immune responses against chlamydial infection.

More specifically, Chlamydial antigens useful in the present invention include DNA gyrase subunit B, sulfite synthesis/biphosphate phosphatase, cell division protein FtsY, methionyl-tRNA synthetase, DNA helicase (uvrD); ATP synthase subunit I (atpI) or a metal-dependent hydrolase (U.S. Patent Application Pub. No. 20090028891). Additional *Chlamyidia trachomatis* antigens include CT144 polypeptide, a peptide having amino acid residues 67-86 of CT144, a peptide having amino acid residues 77-96 of CT144, CT242 protein, a peptide having amino acids 109-117 of CT242, a peptide having amino acids 112-120 of CT242 polypeptide, CT812 protein (from the pmpD gene), a peptide having amino acid residues 103-111 of the CT812 protein; and several other antigenic peptides from *C. trachomatis*: NVTQDLTSSTAKLECTQDLI (SEQ ID NO: 29), AKLECTQDLIAQGKLIVTNP (SEQ ID NO: 30), SNLKRMQKI (SEQ ID NO: 31), AALYSTEDL (SEQ ID NO: 32), FQEKDADTL (SEQ ID NO: 33), QSVNELVYV (SEQ ID NO: 34), LEFASCSSL (SEQ ID NO: 35), SQAEGQYRL (SEQ ID NO: 36), GQSVNELVY (SEQ ID NO: 37), and QAVLLLDQI (SEQ ID NO: 38). See WO 2009/020553. Additionally, *Chlamydia pneumoniae* antigens including homologues of the foregoing polypeptides (see U.S. Pat. No. 6,919,187), can be used an antigens in the immunogenic compositions and methods as disclosed herein.

Fungal antigens can be derived from *Candida* species and other yeast; or other fungi (*aspergillus*, other environmental fungi). Regarding other parasites, malaria as well as worms and amoebae may provide the antigenic antigen for use in the in the immunogenic compositions and methods as disclosed herein.

In some embodiments, where the antigen is to generate an anti-influenza immunogen, the surface glycoproteins hemagglutinin (HA) and neuraminidase (NA) are generally the antigens of choice. Both nucleoprotein (NP) polypeptide and matrix (M) are internal viral proteins and therefore not usually considered in vaccine design for antibody-based immunity. Influenza vaccines are used routinely in humans, and include vaccines derived from inactivated whole influenza virus, live attenuated influenza virus, or purified and inactivated materials from viral strains. For example, a traditional influenza vaccine can be manufactured using three potentially threatening strains of flu virus. These strains are usually grown in fertilized chicken eggs, which requires extensive processing including egg inoculation and incubation, egg harvest, virus purification and inactivation, processing and pooling the virus or viral components to the final vaccine formulation, and aseptic filling in the appropriate containers. Typically, this egg-based production cycle takes over 70 weeks. In the event of a major influenza epidemic, the availability of a potent and safe vaccine is a major concern. Additionally, there are risks associated with impurities in eggs, such as antibiotics and contaminants, that negatively impact vaccine sterility. Moreover, egg-derived flu vaccines are contraindicated for those with severe allergies to egg proteins and people with a history of Guillain-Barré syndrome. The present invention provides an alternative to the egg-based influenza vaccines, not only be avoiding egg-related selequae, but be providing a platform for the use of multiple influenza antigens in a highly controlled platform.

In some embodiments, an antigen for use in the immunogenic compositions as disclosed herein can also include those used in biological warfare, such as ricin, which may provoke a CMI response.

Additionally, the present invention also provides immunogenic compositions comprising antigens which raise an immune response against cancer. In these conjugates, an antigen is an antigen expressed by a cancer or tumor, or derived from a tumor. In some embodiments, such antigens are referred to herein as a "cancer antigen" and are typically a protein expressed predominantly on the cancer cells, such that the conjugate elicits both potent humoral and potent cellular immunity to this protein. A large number of cancer-associated antigens have been identified, several of which are now being used to make experimental cancer treatment vaccines and are thus suitable for use in the present embodiments. Antigens associated with more than one type of cancer include Carcinoembryonic antigen (CEA); Cancer/testis antigens, such as NY-ESO-1; Mucin-1 (MUC1) such as Sialyl Tn (STn); Gangliosides, such as GM3 and GD2; p53 protein; and HER2/neu protein (also known as ERBB2). Antigens unique to a specific type of cancer include a mutant form of the epidermal growth factor receptor, called EGFRvIII; Melanocyte/melanoma differentiation antigens, such as tyrosinase, MARTI, gp100, the lineage related cancer-testis group (MAGE) and tyrosinase-related antigens; Prostate-specific antigen; Leukaemia-associated antigens (LAAs), such as the fusion protein BCR-ABL, Wilms' tumour protein and proteinase 3; and Idiotype (Id) antibodies. See, e.g., Mitchell, 3 Curr. Opin. Investig. Drugs 150 (2002); Dao & Scheinberg, 21 Best Pract. Res. Clin. Haematol. 391 (2008).

Another approach in generating an immune response against cancer employs antigens from microbes that cause or contribute to the development of cancer. These vaccines have been used against cancers including hepatocellular carcinoma (hepatitis B virus, hepatitis C virus, *Opisthorchis viverrin*), lymphoma and nasoparyngeal carcinoma (Epstei-Barr virus), colorectal cancer, stomach cancer (*Helicobacter pylori*), bladder cancer (*Schisosoma hematobium*), T-cell leukemia (human T-cell lymphtropic virus), cervical cancer (human papillomavirus), and others. To date, there have been clinical trials for vaccines targeting Bladder Cancer, Brain Tumors, Breast Cancer, Cervical Cancer, Kidney Cancer, Melanoma, Multiple Myeloma, Leukemia, Lung Cancer, Pancreatic Cancer, Prostate Cancer, and Solid Tumors. See Pardoll et al., ABELOFF'S CLIN. ONCOL. (4th ed., Churchill Livingstone, Philadelphia 2008); Sioud, 360 Methods Mol. Bio. 277 (2007); Pazdur et al., 30 J. Infusion Nursing 30(3):173 (2007); Parmiani et al., 178 J. Immunol. 1975 (2007); Lollini et al., 24 Trends Immunol. 62 (2003); Schlom et al., 13 Clin. Cancer Res. 3776 (2007); Banchereau et al., 392 Nature 245 (1998); Finn, 358 New Engl. J. Med. 2704 (2008); Curigliano et al., 7 Exp. Rev. Anticancer Ther. 1225 (2007). Marek's Disease virus, a herpes virus that causes tumors in poultry, has long been managed by vaccine. Thus, the present embodiments encompass both preventive or prophylactic anti-cancer immunogenic compositions and treatment/therapeutic cancer vaccines.

Contemplated proliferative diseases and cancers include AIDS related cancers, acoustic neuroma, acute lymphocytic leukemia, acute myeloid leukemia, adenocystic carcinoma, adrenocortical cancer, agnogenic myeloid metaplasia, alopecia, alveolar soft-part sarcoma, anal cancer, angiosarcoma, astrocytoma, ataxia-telangiectasia, basal cell carcinoma (skin), bladder cancer, bone cancers, bowel cancer, brain and CNS tumors, breast cancer, carcinoid tumors, cervical cancer, childhood brain tumours, childhood cancer, childhood leukemia, childhood soft tissue sarcoma, chondrosarcoma, choriocarcinoma, chronic lymphocytic leukemia, chronic myeloid leukemia, colorectal cancers, cutaneous t-cell lymphoma, dermatofibrosarcoma-protuberans, desmoplastic-small-round-cell-tumour, ductal carcinoma, endocrine cancers, endometrial cancer, ependymoma, esophageal cancer, Ewing's sarcoma, extra-hepatic bile duct cancer, eye cancer, including, e.g., eye melanoma and retinoblastoma, fallopian tube cancer, fanconi anemia, fibrosarcoma, gall bladder cancer, gastric cancer, gastrointestinal cancers, gastrointestinal-carcinoid-tumour, genitourinary cancers, germ cell tumors, gestational-trophoblastic disease, glioma, gynecological cancers, hematological malignancies, hairy cell leukemia, head and neck cancer, hepatocellular cancer, hereditary breast cancer, Hodgkin's disease, human papillomavirus-related cervical cancer, hydatidiform mole, hypopharynx cancer, islet cell cancer, Kaposi's sarcoma, kidney cancer, laryngeal cancer, leiomyosarcoma, leukemia, Li-Fraumeni syndrome, lip cancer, liposarcoma, lung cancer, lymphedema, lymphoma, non-Hodgkin's lymphoma, male breast cancer, malignant-rhabdoid-tumour-of-kidney, medulloblastoma, melanoma, Merkel cell cancer, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, Nijmegen breakage syndrome, non-melanoma skin cancer, non-small-cell-lung-cancer-(NSCLC), oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal-tumours, pituitary cancer, polycythemia vera, prostate cancer, renal cell carcinoma, retinoblastoma, rhabdomyosarcoma, Rothmund-Thomson syndrome, salivary gland cancer, sarcoma, Schwannoma, Sezary syndrome, skin cancer, small cell lung cancer (SCLC), small intestine cancer, soft tissue sarcoma, spinal cord tumours, squamous-cell-carcinoma-(skin), stomach cancer, synovial sarcoma, testicular cancer, thymus cancer, thyroid cancer, transitional-cell-cancer-(bladder), transitional-cell-cancer (renal-pelvis/ureter), trophoblastic cancer, urethral cancer, urinary system cancer, uterine sarcoma, uterus cancer, vaginal cancer, vulva cancer, Waldenstrom's-macroglobulinemia, and Wilms' tumor.

In some embodiments, an antigen for use in the immunogenic compositions as disclosed herein can include antigens of autoimmune diseases, e.g., they can be "self-antigens." Autoimmune diseases contemplated for diagnosis according to the assays described herein include, but are not limited to alopecia areata, ankylosing spondylitis, antiphospholipid syndrome, Addison's disease, aplastic anemia, multiple sclerosis, autoimmune disease of the adrenal gland, autoimmune hemolytic anemia, autoimmune hepatitis, autoimmune oophoritis and orchitis, Behcet's Disease, bullous pemphigoid, cardiomyopathy, celiac sprue-dermatitis, chronic fatigue syndrome, chronic inflammatory demyelinating syndrome (CFIDS), chronic inflammatory polyneuropathy, Churg-Strauss syndrome, cicatricial pemphigoid, CREST Syndrome, cold agglutinin disease, Crohn's disease, dermatitis herpetiformis, discoid lupus, essential mixed cryoglobulinemia, fibromyalgia, glomerulonephritis, Grave's disease, Guillain-Barre, Hashimoto's thyroiditis, idiopathic pulmonary fibrosis, idiopathic thrombocytopenia purpura (ITP), IgA nephropathy, insulin dependent diabetes (Type I), Lichen Planus, lupus, Meniere's Disease, mixed connective tissue disease, myasthenia gravis, myocarditis, pemphigus vulgaris, pernicious anemia, polyarteritis *nodosa*, polychondritis, polyglandular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjogren's syndrome, stiff-man syndrome, Takayasu arteritis, temporal arteritis/giant cell arteritis, ulcerative colitis, uveitis, Wegener's syndrome, vasculitis and vitiligo. It is generally important to assess the potential or actual CMI responsiveness in subjects having, or suspected of having or being susceptible to an autoimmune disease.

In some embodiments, an antigen for use in the immunogenic compositions as disclosed herein can be an antigen which is associated with an inflammatory disease or condition. Examples of inflammatory disease conditions where antigens may be useful include but are not limited to acne, angina, arthritis, aspiration pneumonia, empyema, gastroenteritis, necrotizing enterocolitis, pelvic inflammatory disease, pharyngitis, pleurisy, chronic inflammatory demyelinating polyneuropathy, chronic inflammatory demyelinating polyradiculoneuropathy, and chronic inflammatory demyelinating polyneuropathy, among others.

In some embodiments, an antigen can be an intact (i.e., an entire or whole) antigen, or a functional portion of an antigen that comprises more than one epitope. In some embodiments, an antigen is a peptide functional portion of an antigen. By "intact" in this context is meant that the antigen is the full length antigen as that antigen polypeptide occurs in nature. This is in direct contrast to delivery of only a small portion or peptide of the antigen. Delivering an intact antigen to a cell enables or facilitates eliciting an immune response to a full range of epitopes of the intact antigen, rather than just a single or selected few peptide epitopes. Accordingly, the methods and immunogenic compositions described herein encompass intact antigens associated with the polymer for a more sensitive and have higher specificity of immune response as compared to use of a single epitope peptide-based antigen.

Alternatively, in some embodiments, an intact antigen can be divided into many parts, depending on the size of the initial antigen. Typically, where a whole antigen is a multimer polypeptide, the whole protein can be divided into sub-units and/or domains where each individual sub-unit or domain of the antigen can be associated with the polymer according to the methods as disclosed herein. Alternatively, in some embodiments, an intact antigen can be divided into functional fragments, or parts, of the whole antigen, for example, at least two, or at least 3, or at least 4, or at least 5, or at least 6, or at least 7, or at least 8, or at least 9, or at least 10, or at least 11, or at least 12, or at least 13, or at least 15, or at least 20, or at least 25, or more than 25 portions (e.g., pieces or fragments), inclusive, and where each individual functional fragment of the antigen can be associated with the polymer according to the methods as disclosed herein.

The fragmentation or division of a full length antigen polypeptide can be an equal division of the full length antigen polypeptide, or alternatively, in some embodiments, the fragmentation is asymmetrical or unequal. As a non-limiting example, where an antigen is divided into two overlapping fragments, an antigen can be divided into fragments of approximately the same (equal) size, or alternatively one fragment can be about 45% of the whole antigen and the other fragment can be about 65%. As further non-limiting examples, a whole antigen can be divided into a combination of differently sized fragments, for example, where an antigen is divided into two fragments, fragments can be divided into about 40% and about 70%, or about 45% and about 65%; or about 35% and about 75%; or about 25% and about 85%, inclusive, of the whole antigen. Any combination of overlapping fragments of a full length whole antigen is encompassed for use in the generation of a panel of overlapping polypeptides of an antigen. As an illustrative example only, where a antigen is divided into 5 portions, the portions can divided equally (i.e., each overlapping fragment is about 21% to 25% of the entire full length if the antigen) or unequally (i.e., an antigen can be divided into the following five overlapping fragments; fragment 1 is about 25%, fragment 2 is about 5%, fragment 3 is about 35%, fragment 4 is about 10% and fragment 5 is about 25% of the size of the full length antigen, provided each fragment overlaps with at least one other fragment).

Typically, a panel of antigen portions can substantially cover the entire length of the whole (or intact) antigen polypeptide. Accordingly, in some embodiments, an immunogenic composition comprises a polymer with many different, and/or overlapping fragments of the same intact antigen. Overlapping protein fragments of a antigen can be produced much quicker and cheaper, and with increased stability as compared to the use of peptide antigens alone. Further in some embodiments, antigens which are polypeptides larger than simple peptides are preferred as conformation is important for epitope recognition, and the larger antigen polypeptides or fragments will provide a benefit over peptide fragments.

One of ordinary skill in the art can divide a whole antigen into overlapping proteins of an antigen to create a panel of polypeptides of the antigen. By way of an illustrative example only, the TB-specific antigen TB1 (CFP also known as culture filtrate-10 or CFP-10) can be divided into, for example at least seventeen portions to generate a panel of seventeen different polypeptides, each comprising a different but overlapping TB-specific antigen TB1 (CFP) fragment. Culture filtrate protein (CFP-10) (Genbank AAC83445) is a 10 kDa, 100 amino acid residue protein fragment from *M. tuberculosis*. It is also known as L45 antigen homologous protein (LHP).

A target antigen for use in the methods and compositions described herein can be expressed by recombinant means, and can optionally include an affinity or epitope tag to facilitate purification, which methods are well-known in the art. Chemical synthesis of an oligopeptide, either free or conjugated to carrier proteins, can be used to obtain antigen of the invention. Oligopeptides are considered a type of polypeptide. An antigen can be expressed as a fusion with a complementary affinity molecule, e.g., but not limited to rhizavidin or a derivative or functional fragment thereof. Alternatively, it is also possible to prepare target antigen and then conjugate it to a complementary affinity molecule, e.g., but not limited to rhizavidin or a derivative or functional fragment thereof.

Polypeptides can also by synthesized as branched structures such as those disclosed in U.S. Pat. Nos. 5,229,490 and 5,390,111. Antigenic polypeptides include, for example, synthetic or recombinant B-cell and T-cell epitopes, universal T-cell epitopes, and mixed T-cell epitopes from one organism or disease and B-cell epitopes from another.

An antigen can obtained through recombinant means or chemical polypeptide synthesis, as well as antigen obtained from natural sources or extracts, can be purified by means of the antigen's physical and chemical characteristics, such as by fractionation or chromatography. These techniques are well-known in the art.

In some embodiments, an antigen can be solubilized in water, a solvent such as methanol, or a buffer. Suitable buffers include, but are not limited to, phosphate buffered saline $Ca^{2+}/Mg^{2+}$ free (PBS), normal saline (150 mM NaCl in water), and Tris buffer. Antigen not soluble in neutral buffer can be solubilized in 10 mM acetic acid and then diluted to the desired volume with a neutral buffer such as PBS. In the case of antigen soluble only at acid pH, acetate-PBS at acid pH can be used as a diluent after solubilization in dilute acetic acid. Glycerol can be a suitable non-aqueous solvent for use the compositions, methods and kits described herein.

Typically, when designing a protein vaccine against a pathogen, an extracellular protein or one exposed to the environment on a virus is often the ideal candidate as the antigen component in the vaccine. Antibodies generated against that extracellular protein become the first line of defense against the pathogen during infection. The antibodies bind to the protein on the pathogen to facilitate antibody opsonization and mark the pathogen for ingestion and destruction by a phagocyte such as a macrophage. Antibody opsonization can also kill the pathogen by antibody-dependent cellular cytotoxicity. The antibody triggers a release of lysis products from cells such as monocytes, neutrophils, eosinophils, and natural killer cells.

In one embodiment of the invention described herein, antigens for use in the compositions as disclosed herein all wild type proteins, as in the amino acid residues have the sequences found in naturally occurring viruses and have not been altered by selective growth conditions or molecular biological methods.

In one embodiment, the immunogenic compositions described as herein can comprise antigens which are glycosylated proteins. In other words, an antigen of interest can each be a glycosylated protein. In one embodiment of the immunogenic compositions as described herein, antigens, or antigen-fusion polypeptides are O-linked glycosylated. In another embodiment of the immunogenic compositions as described herein, antigens, or antigen-fusion polypeptides are N-linked glycosylated. In yet another embodiment of the immunogenic compositions as described herein, antigens, or antigen-fusion are both O-linked and N-linked glycosylated. In other embodiments, other types of glycosylations are possible, e.g., C-mannosylation. Glycosylation of proteins occurs predominantly in eukaryotic cells. N-glycosylation is important for the folding of some eukaryotic proteins, providing a co-translational and post-translational modification mechanism that modulates the structure and function of membrane and secreted proteins. Glycosylation is the enzymatic process that links saccharides to produce glycans, and attaches them to proteins and lipids. In N-glycosylation, glycans are attached to the amide nitrogen of asparagine side chain during protein translation. The three major saccharides forming glycans are glucose, mannose, and N-acetylglucosamine molecules. The N-glycosylation consensus is Asn-Xaa-Ser/Thr, where Xaa can be any of the known amino acids. O-linked glycosylation occurs at a later stage during protein processing, probably in the Golgi apparatus. In O-linked glycosylation, N-acetyl-galactosamine, O-fucose, O-glucose, and/or N-acetylglucosamine is added to serine or threonine residues. One skilled in the art can use bioinformatics software such as NetNGlyc 1.0 and NetOGlyc Prediction softwares from the Technical University of Denmark to find the N- and O-glycosylation sites in a polypeptide in the present invention. The NetNglyc server predicts N-Glycosylation sites in proteins using artificial neural networks that examine the sequence context of Asn-Xaa-Ser/Thr sequons. The NetNGlyc 1.0 and NetOGlyc 3.1 Prediction software can be accessed at the EXPASY website. In one embodiment, N-glycosylation occurs in the target antigen polypeptide of the fusion polypeptide described herein.

Affinity Molecule Pairs

As disclosed herein, in some embodiments, an antigen is connected to a polymer via complementary affinity pairs. This connecting of the antigen to the polymer is mediated by the polymer being connected to a first affinity molecule, which associates a second (e.g., complementary) affinity molecule, which is attached to the antigen. An example complementary affinity pair is biotin/biotin-binding protein.

Exemplary examples of the affinity complementary affinity pairs include, but without limitation, biotin-binding proteins or avidin-like proteins that bind to biotin. For example, where the first affinity binding molecule is biotin (which associates with the polymer), the complementary affinity molecule can be a biotin-binding protein or an avidin-like protein or a derivative thereof, e.g., but not limited to, avidin, rhizavidin, or streptavidin or variants, derivatives or functional portions thereof.

In some embodiments, the first affinity binding molecule is biotin, a biotin derivative, or a biotin mimic, for example, but not limited to, amine-PEG3-biotin (((+)-biotinylation-3-6,9-trixaundecanediamine) or a derivative or functional fragment thereof. A specific biotin mimetic has a specific peptide motif containing sequence of $DX_aAX_bPX_c$ (SEQ ID NO: 39), or $CDX_aAX_bPX_cCG$ (SEQ ID NO: 40), where $X_a$ is R or L, $X_b$ is S or T, and $X_a$ is Y or W. These motifs can bind avidin and Neutravidin, but streptavidin. See, e.g., Gaj et al., 56 Prot. Express. Purif. 54 (2006).

The linkage of the first affinity molecule to the polymer, and the complementary affinity molecule to the antigen can be a non-covalent linkage, or a chemical mechanism, for instance covalent binding, affinity binding, intercalation, coordinate binding and complexation. Covalent binding provides for very stable binding, and is particularly well-suited for the present embodiments. Covalent binding can be achieved either by direct condensation of existing side chains or by the incorporation of external bridging molecules.

For example, in some embodiments, an antigen can be non-covalently bonded to one of the pairs in a complementary affixing pair. In alternative embodiments, an antigen can be covalently bonded or fused to one of the pairs in a complementary affixing pair. Methods for generation of fusion proteins are well known in the art, and are discussed herein.

In other embodiments, a first affinity binding molecule is linked to the polymer by a non-covalent bond, or by a covalent bond. In some embodiments, a cross-linking reagent is used to covalently bond the first affinity binding molecule to the polymer as disclosed herein.

In some embodiments, the first affinity binding molecule associates with the complementary affinity molecule by non-covalent bond association as known in the art, including, but not limited to, electrostatic interaction, hydrogen bound, hydrophobic interaction (i.e., van der Waals forces), hydrophilic interactions, and other non-covalent interactions. Other higher order interactions with intermediate moieties are also contemplated.

In some embodiments, the complementary affinity molecule is an avidin-related polypeptide. In specific embodiments, the complementary affinity molecule is rhizavidin, such as recombinant rhizavidin. In particular, the recombinant rhizavidin is a modified rhizavidin that can be expressed in E. coli with a high yield. The typical yield is >30 mg per liter of E. coli culture. Rhizavidin has a lower sequence homology to egg avidin (22.4% sequence identity and 35.0% similarity) compared with other avidin-like proteins. Use of the modified rhizavidin reduces the risk of the MAPS inducing an egg-related allergic reaction in a subject. Moreover, antibody to recombinant modified rhizavidin has no apparent cross-reactivity to egg avidin (and vice versa).

More specifically, some embodiments comprise a modified rhizavidin designed for recombinant expression in E. coli. The coding sequence for the rhizavidin gene was optimized using E. coli expression codons, to avoid any difficulty during expression in E. coli due to rare codons present in original gene. To simplify the construct, after a bioinformatics and structure-based analysis, the first 44 residues of full length rhizavidin were removed, as these were found to be unnecessary for the core structure and function. The correct folding of recombinant protein was improved by added an E. coli secretion signal sequence to the N-terminal of the shortened rhizavidin (45-179), to facilitate the translocation of recombinant protein into the periplasmic space of E. coli cells where the functionally important disulfide bond in rhizavidin can form correctly. The modified recombinant rhizavidin forms a dimer, compared with known avidin-like proteins which form tetramers, further improving expression of the recombinant rhizavidin-antigen fusion as a soluble protein in E. coli.

Moreover, as discussed in further detail elsewhere herein, to improve the expression and solubility of fusion antigens in E. coli, a flexible linker region was added between rhizavidin and the antigen protein. Additionally, based on the biotinformatics and structural analysis, different antigen constructs were cloned and expressed: either full length antigen, or the important functional domain, or chimera proteins were comprising with two different antigens.

Additional affinity pairs that may be useful in the methods and compositions described herein include antigen-antibody, metal/ion-metal/ion-binding protein, lipid/lipid binding protein, saccharide/saccharide binding protein, amino acid/peptide/amino acid or peptide binding protein, enzyme-substrate or enzyme-inhibitor, ligand-agonist/receptor, or biotin mimetic. When using alternative affinity pairs, alternative means of attaching the respective polymer and antigen may also be employed, such as in vitro enzymatic reactions rather than genetic fusion. More specifically, antigen-antibody affinity pair provides for a very strong and specific interaction. The antigen can be any epitope including protein, peptide, nucleic acid, lipid, poly/oligosaccharide, ion, etc. The antibody can be any type of immunoglobulin, or the Ag-binding portion of an immunoglobulin, such as a Fab fragment. Regarding metal/ion-metal/ion binding protein, examples include Ni NTA vs. histidine-tagged protein, or Zn vs. Zn binding protein. Regarding lipid/lipid binding protein, examples include cholesterol vs. cholesterol binding protein. Regarding saccharide/saccharide binding protein, examples include maltose vs. maltose binding protein, mannose/glucose/oligosaccharide vs. lectin. Enzyme-substrate/inhibitors include substrates from a wide range of substances, including protein, peptide, amino acid, lipid, sugar, or ions. The inhibitor can be the analog of the real substrate which can generally bind to the enzymes more tightly and even irreversibly. For example, trypsin vs. soy trypsin inhibitor. The inhibitor can be natural or synthetic molecule. Regarding other ligand/agonist-receptor, ligand can be from a wide range of substance, including protein, peptide, amino acid, lipid, sugar, ion, agonist can be the analog of the real ligand. Examples include the LPS vs. TLR4 interaction.

Cross-Linking Reagents:

Many bivalent or polyvalent linking agents are useful in coupling protein molecules to other molecules. For example, representative coupling agents can include organic compounds such as thioesters, carbodiimides, succinimide esters, disocyanates, glutaraldehydes, diazobenzenes and hexamethylene diamines. This listing is not intended to be exhaustive of the various classes of coupling agents known in the art but, rather, is exemplary of the more common coupling agents. See Killen & Lindstrom, 133 J. Immunol. 1335 (1984); Jansen et al., 62 Imm. Rev. 185 (1982); Vitetta et al.

In some embodiments, cross-linking reagents agents described in the literature are encompassed for use in the methods, immunogenic compositions and kits as disclosed herein. See, e.g., Ramakrishnan, et al., 44 Cancer Res. 201 (1984) (describing the use of MBS (M-maleimidobenzoyl-N-hydroxysuccinimide ester)); Umemoto et al., U.S. Pat. No. 5,030,719 (describing the use of a halogenated acetyl hydrazide derivative coupled to an antibody by way of an oligopeptide linker). Particular linkers include: (a) EDC (1-ethyl-3-(3-dimethylamino-propyl) carbodiimide hydrochloride; (b) SMPT (4-succinimidyloxycarbonyl-alpha-methyl-alpha-(2-pyridyl-dithio)-toluene (Pierce Chem. Co., Cat. (21558G); (c) SPDP (succinimidyl-6 [3-(2-pyridyldithio) propionamido] hexanoate (Pierce Chem. Co., Cat #21651G); (d) Sulfo-LC-SPDP (sulfosuccinimidyl 6 [3-(2-pyridyldithio)-propianamide] hexanoate (Pierce Chem. Co. Cat. #2165-G); and (f) sulfo-NHS (N-hydroxysulfo-succinimide: Pierce Chem. Co., Cat. #24510) conjugated to EDC.

The linkages or linking agents described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage can be cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

Exemplary cross-linking molecules for use in the methods and immunogenic compositions as disclosed herein include, but are not limited to those listed in Tables 2 and 3.

TABLE 2

Exemplary homobifunctional crosslinkers*

| Crosslinking Target | Crosslinker Reactive Groups, Features | Example Products |
|---|---|---|
| Amine-to-Amine | NHS esters | DSG; DSS; BS3; TSAT (trifunctional); Bioconjugate Toolkit Reagent Pairs |
|  | NHS esters, PEG spacer | BS(PEG)5; BS(PEG)9 |
|  | NHS esters, thiol-cleavable | DSP; DTSSP |
|  | NHS esters, misc-cleavable | DST; BSOCOES; EGS; Sulfo-EGS |
|  | Imidoesters | DMA; DMP; DMS |
|  | Imidoesters, thiol-cleavable | DTBP |
|  | Other | DFDNB; THPP (trifunctional); Aldehyde-Activated Dextran Kit |
| Sulfhydryl-to-Sulfhydryl | Maleimides | BMOE; BMB; BMH; TMEA (trifunctional) |
|  | Maleimides, PEG spacer | BM(PEG)2; BM(PEG)3 |
|  | Maleimides, cleavable | BMDB; DTME |
|  | Pyridyldithiols (cleavable) | DPDPB |
|  | Other | HBVS (vinylsulfone) |
| Nonselective | Aryl azides | BASED (thiol-cleavable) |

*crosslinking reagents that have the same type of reactive group at either end. Reagents are classified by what chemical groups they cross link (left column) and their chemical composition (middle column). Products are listed in order of increasing length within each cell.

TABLE 3

Exemplary heterobifunctional crosslinkers*

| Crosslinking Targets | Crosslinker Reactive Groups, Features | Example Products |
|---|---|---|
| Amine-to-Sulfhydryl | NHS ester/Maleimide | AMAS; BMPS; GMBS and Sulfo-GMBS; MBS and Sulfo-MBS; SMCC and Sulfo-SMCC; EMCS and Sulfo-EMCS; SMPB and Sulfo-SMPB; SMPH; LC-SMCC; Sulfo-KMUS |
| | NHS ester/Maleimide, PEG spacer | SM(PEG)2; SM(PEG)4; SM(PEG)6; SM(PEG)8; SM(PEG)12; SM(PEG)24 |
| | NHS ester/Pyridyldithiol, cleavable | SPDP; LC-SPDP and Sulfo-LC-SPDP; SMPT; Sulfo-LC-SMPT |
| | NHS esters/Haloacetyl | SIA; SBAP; SIAB; Sulfo-SIAB |
| Amine-to-Nonselective | NHS ester/Aryl Azide | NHS-ASA ANB-NOS Sulfo-HSAB Sulfo-NHS-LC-ASA SANPAH and Sulfo-SANPAH |
| | NHS ester/Aryl Azide, cleavable | Sulfo-SFAD; Sulfo-SAND; Sulfo-SAED |
| | NHS ester/Diazirine | SDA and Sulfo-SDA; LC-SDA and Sulfo-LC-SDA |
| | NHS ester/Diazirine, cleavable | SDAD and Sulfo-SDAD |
| Amine-to-Carboxyl | Carbodiimide | DCC; EDC |
| Sulfhydryl-to-Nonselective | Pyridyldithiol/Aryl Azide | APDP |
| Sulfhydryl-to-Carbohydrate | Maleimide/Hydrazide | BMPH; EMCH; MPBH; KMUH |
| | Pyridyldithiol/Hydrazide | BMPH; EMCH; MPBH; KMUH |
| Carbohydrate-to-Nonselective | Hydrazide/Aryl Azide | ABH |
| Hydroxyl-to-Sulfhydryl | Isocyanate/Maleimide | PMPI |
| Amine-to-DNA | NHS ester/Psoralen | SPB |

*crosslinking reagents that have the different reactive groups at either end. Reagents are classified by what chemical groups they cross link (left column) and their chemical composition (middle column). Products are listed in order of increasing length within each cell.

Co-Stimulatory Factor

In some embodiments, the immunogenic composition as disclosed herein comprises at least one co-stimulatory molecule. In some embodiments, the co-stimulatory factor is cross-linked to the polymer. In some embodiments, the co-stimulatory factor is associated to the polymer by a complementary affinity pair similar to as an antigen is associated with the polymer. In some embodiments, where the complementary affinity pair which links the co-stimulatory factor to the polymer is the same, or a different complementary affinity pair which links the antigen to the polymer.

In some embodiments, at least one, or at least 2, or at least 3, or at least 5, or at least 10, or at least 15, or at least 20, or at least 50, or at least 100, or more than about 100, inclusive, co-stimulatory factors can be associated with the polymer as disclosed herein. In some embodiments, the co-stimulatory factors can be the same co-stimulator factor, or they can be a variety of different co-stimulatory factors associated with the polymer.

In some embodiments, the co-stimulator factor is a ligand/agonist of Toll like receptors, e.g., but not limited to TLR1, TLR2, TLR3, TLR4, TLR5, TLR6, TLR7, TLR8, TLR9, TLR10, TLR11, etc. In some embodiments, a co-stimulator factor is a NOD ligand/agonist, or an activator/agonist of the inflammasome. Without wishing to be bound by theory, the inflammasome is a multiprotein oligomer consisting of caspase 1, PYCARD, NALP and sometimes caspase 5 or caspase 11 and promotes the maturation of inflammatory cytokines interleukin 1-β and interleukin 18.

In some embodiments, a co-stimulator factor is a cytokine. In some embodiments, a cytokine is selected from the group consisting of: GM-CSF; IL-1α; IL-1β; IL-2; IL-3; IL-4; IL-5; IL-6; IL-7; IL-8; IL-10; IL-12; IL-23; IFN-α; IFN-β; IFN-β; IFN-γ; MIP-1α; MIP-1β; TGF-β; TNFα, and TNFβ. In some embodiments, the co-stimulatory factor is an adjuvant, which may be associated with the polymer, as just discussed, or may be added to the MAPS composition prior to or concurrent with administration to a subject. Adjuvants are further described elsewhere herein.

Production of Recombinant Proteins

Recombinant proteins may be conveniently expressed and purified by a person skilled in the art, or by using commercially available kits, for example PROBOND™ Purification System (Invitrogen Corp., Carlsbad, Calif.). In some embodiments, recombinant antigens can be synthesized and purified by protein purification methods using bacterial expression systems, yeast expression systems, baculovirus/insect cell expression system, mammalian cell expression systems, or transgenic plant or animal systems as known to persons of ordinary skill in the art.

The proteins, polypeptides and fusion polypeptides described herein can all be synthesized and purified by protein and molecular methods that are well known to one skilled in the art. Molecular biology methods and recombinant heterologous protein expression systems are used. For example, recombinant protein can be expressed in bacteria, mammalian, insect, yeast, or plant cells; or in transgenic plant or animal hosts.

In one embodiment, provided herein is an isolated polynucleotide encoding a fusion polypeptide or a non-fusion polypeptide described herein. Conventional polymerase chain reaction (PCR) cloning techniques can be used to construct a chimeric or fusion coding sequence encoding a fusion polypeptide as described herein. A coding sequence can be cloned into a general purpose cloning vector such as pUC19, pBR322, pBLUESCRIPT® vectors (Stratagene, Inc.) or pCR TOPO® (Invitrogen). The resultant recombinant vector carrying the nucleic acid encoding a polypeptide as described herein can then be used for further molecular biological manipulations such as site-directed mutagenesis to create a variant fusion polypeptide as described herein or can be subcloned into protein expression vectors or viral vectors for protein synthesis in a variety of protein expression systems using host cells selected from the group consisting of mammalian cell lines, insect cell lines, yeast, bacteria, and plant cells.

Each PCR primer should have at least 15 nucleotides overlapping with its corresponding templates at the region to be amplified. The polymerase used in the PCR amplification should have high fidelity such as PfuULTRA® polymerase (Stratagene) for reducing sequence mistakes during the PCR amplification process. For ease of ligating several separate PCR fragments together, for example in the construction of a fusion polypeptide, and subsequently inserting into a cloning vector, the PCR primers should also have distinct and unique restriction digestion sites on their flanking ends that do not anneal to the DNA template during PCR amplification. The choice of the restriction digestion sites for each pair of specific primers should be such that the fusion polypeptide coding DNA sequence is in-frame and will encode the fusion polypeptide from beginning to end with no stop codons. At the same time the chosen restriction digestion sites should not be found within the coding DNA sequence for the fusion polypeptide. The coding DNA sequence for the intended polypeptide can be ligated into cloning vector pBR322 or one of its derivatives, for amplification, verification of fidelity and authenticity of the chimeric coding sequence, substitutions/or specific site-directed mutagenesis for specific amino acid mutations and substitutions in the polypeptide.

Alternatively the coding DNA sequence for the polypeptide can be PCR cloned into a vector using for example, the TOPO® cloning method comprising topoisomerase-assisted TA vectors such as pCR®-TOPO, pCR®-Blunt II-TOPO, pENTR/D-TOPO®, and pENTR/SD/D-TOPO®. (Invitrogen, Inc., Carlsbad, Calif.). Both pENTR/D-TOPO®, and pENTR/SD/D-TOPO® are directional TOPO entry vectors which allow the cloning of the DNA sequence in the 5'→3' orientation into a GATEWAY® expression vector. Directional cloning in the 5'→3' orientation facilitates the unidirectional insertion of the DNA sequence into a protein expression vector such that the promoter is upstream of the 5' ATG start codon of the fusion polypeptide coding DNA sequence, enabling promoter driven protein expression. The recombinant vector carrying the coding DNA sequence for the fusion polypeptide can be transfected into and propagated in general cloning E. coli such as XL1Blue, SURE® (STRATAGENE®) and TOP-10 cells (Invitrogen).

One skilled in the art would be able to clone and ligate the coding region of the antigen of interest with the coding region of the complementary affinity molecule to construct a chimeric coding sequence for a fusion polypeptide comprising the antigen or a fragment thereof and the complementary affinity molecule of a derivative thereof using specially designed oligonucleotide probes and polymerase chain reaction (PCR) methodologies that are well known in the art. One skilled in the art would also be able to clone and ligate the chimeric coding sequence for a fusion protein into a selected vector, e.g., bacterial expression vector, an insect expression vector or baculovirus expression vector. The coding sequences of antigen and the target antigen polypeptide or fragment thereof should be ligated in-frame and the chimeric coding sequence should be ligated downstream of the promoter, and between the promoter and the transcription terminator. Subsequent to that, the recombinant vector is transfected into regular cloning E. coli, such as XL1Blue. Recombinant E. coli harboring the transfer vector DNA is then selected by antibiotic resistance to remove any E. coli harboring non-recombinant plasmid DNA. The selected transformant E. coli are grown and the recombinant vector DNA can be subsequently purified for transfection into S. frugiperda cells.

In some embodiments, the antigens as disclosed herein can comprise a signal peptide for translocation into periplasmic space of bacteria. The signal peptide is also called a leader peptide in the N-terminus, which may or may not be cleaved off after the translocation through the membrane. One example of a signal peptide is MKKIWLALAGLV-LAFSASA (SEQ ID NO: 2) as disclosed herein. Another signal sequence is MAPFEPLASGILLLLWLIAPSRA (SEQ ID NO: 7). Other examples of signal peptides can be found at SPdb, a Signal Peptide Database, which is found at the world wide web site of "proline.bic.nus.edu.sg/spdb/".

In some embodiments, where the antigen is fused to a biotin-binding protein, the signal sequence can be located at the N-terminal of the biotin-binding protein. In some embodiments, the signal sequence is cleaved off from the biotin-binding protein after translocation into the periplasmic space of E. coli.

In some embodiments, where the antigen is fused to a complementary affinity protein, the signal sequence can be located at the N-terminal of the complementary affinity protein. For example, if an antigen is fused to an avidin-like protein, the signal sequence can be located at the N-terminal of the complementary affinity protein. In some embodiments, the signal sequence is cleaved off from the complementary affinity protein before the complementary affinity protein associates with the first affinity molecule.

In some embodiments, an antigen and/or complementary affinity protein as described herein lacks a signal sequence.

The polypeptides described herein can be expressed in a variety of expression host cells e.g., bacteria, yeasts, mammalian cells, insect cells, plant cells, algal cells such as Chlamadomonas, or in cell-free expression systems. In some embodiments the nucleic acid can be subcloned from the cloning vector into a recombinant expression vector that is appropriate for the expression of fusion polypeptide in bacteria, mammalian, insect, yeast, or plant cells or a cell-free expression system such as a rabbit reticulocyte expression system. Some vectors are designed to transfer coding nucleic acid for expression in mammalian cells, insect cells and year in one single recombination reaction. For example, some of the GATEWAY® (Invitrogen) destination vectors are designed for the construction of baculovirus, adenovirus, adeno-associated virus (AAV), retrovirus, and lentiviruses, which upon infecting their respective host cells, permit heterologous expression of fusion polypeptides in the appropriate host cells. Transferring a gene into a destination vector is accomplished in just two steps according to manufacturer's instructions. There are GATEWAY® expression vectors for protein expression in insect cells, mammalian cells, and yeast. Following transformation and selection in E. coli, the expression vector is ready to be used for expression in the appropriate host.

Examples of other expression vectors and host cells are the strong CMV promoter-based pcDNA3.1 (Invitrogen) and pCINEO vectors (Promega) for expression in mammalian cell lines such as CHO, COS, HEK-293, Jurkat, and MCF-7; replication incompetent adenoviral vector vectors pADENO-X™, pAd5F35, pLP-ADENO™-X-CMV (CLONTECH®), pAd/CMVN5-DEST, pAd-DEST vector (Invitrogen) for adenovirus-mediated gene transfer and expression in mammalian cells; pLNCX2, pLXSN, and pLAPSN retrovirus vectors for use with the RETRO-X™ system from Clontech for retroviral-mediated gene transfer and expression in mammalian cells; pLenti4/V5-DEST™, pLenti6N5-DEST™, and pLenti6.2N5-GW/lacZ (Invitrogen) for lentivirus-mediated gene transfer and expression in mammalian cells; adenovirus-associated virus expression vectors such as pAAV-MCS, pAAV-IRES-hrGFP, and pAAV-RC vector (Stratagene) for adeno-associated virus-mediated gene transfer and expression in mammalian cells; BACpak6 baculovirus (Clontech) and pFASTBAC™ HT (Invitrogen) for the expression in *S. frugiperda* 9 (Sf9), Sf11, Tn-368 and BTI-TN-5B4-1 insect cell lines; pMT/BiP/V5-His (Invitrogen) for the expression in *Drosophila schneider* S2 cells; *Pichia* expression vectors pPICZα, pPICZ, pFLDα and pFLD (Invitrogen) for expression in *P. pastoris* and vectors pMETα and pMET for expression in *P. methanolica*; pYES2/GS and pYD1 (Invitrogen) vectors for expression in yeast *S. cerevisiae*.

Recent advances in the large scale expression heterologous proteins in *Chlamydomonas reinhardtii* are described. Griesbeck., 34 Mol. Biotechnol. 213 (2006); Fuhrmann, 94 Methods Mol Med. 191 (2006). Foreign heterologous coding sequences are inserted into the genome of the nucleus, chloroplast and mitochondria by homologous recombination. The chloroplast expression vector p64 carrying the most versatile chloroplast selectable marker aminoglycoside adenyl transferase (aadA), which confer resistance to spectinomycin or streptomycin, can be used to express foreign protein in the chloroplast. The biolistic gene gun method can be used to introduce the vector in the algae. Upon its entry into chloroplasts, the foreign DNA is released from the gene gun particles and integrates into the chloroplast genome through homologous recombination.

Also included in the invention are complementary affinity molecule fused to an antigen. In some embodiments, the fusion construct can also optionally comprise purification tags, and/or secretion signal peptides. These fusion proteins may be produced by any standard method. For example, for production of a stable cell line expressing an antigen-complementary affinity molecule fusion protein, PCR-amplified antigen nucleic acids may be cloned into the restriction site of a derivative of a mammalian expression vector. For example, KA, which is a derivative of pcDNA3 (Invitrogen) contains a DNA fragment encoding an influenza virus hemagglutinin tag (HA). Alternatively, vector derivatives encoding other tags, such as c-myc or poly Histidine tags, can be used. The antigen-complementary affinity molecule fusion expression construct may be co-transfected, with a marker plasmid, into an appropriate mammalian cell line (e.g., COS, HEK293T, or NIH 3T3 cells) using, for example, LIPOFECTAMINE™ (Gibco-BRL, Gaithersburg, Md.) according to the manufacturer's instructions, or any other suitable transfection technique known in the art. Suitable transfection markers include, for example, β-galactosidase or green fluorescent protein (GFP) expression plasmids or any plasmid that does not contain the same detectable marker as the antigen-complementary affinity molecule fusion protein. The fusion protein expressing cells can be sorted and further cultured, or the tagged antigen-complementary affinity molecule fusion protein can be purified. In some embodiments, an antigen-complementary affinity molecule fusion protein is amplified with a signal peptide. In alternative embodiments, a cDNA encoding an antigen-complementary affinity molecule fusion protein can be amplified without the signal peptide and subcloned into a vector (pSecTagHis) having a strong secretion signal peptide. In another example, antigen-complementary affinity molecule fusion protein can have an alkaline phosphatase (AP) tag, or a histadine (His) tag for purification. Any method known to persons of ordinary skill in the art for protein purification of the antigen and/or antigen-complementary affinity molecule fusion protein is encompassed for use in the methods of the invention.

In some embodiments, any of the polypeptides described herein is produced by expression from a recombinant baculovirus vector. In another embodiment, any of the polypeptides described herein is expressed by an insect cell. In yet another embodiment, any of the polypeptides described herein is isolated from an insect cell. There are several benefits of protein expression with baculovirus in insect cells, including high expression levels, ease of scale-up, production of proteins with posttranslational modifications, and simplified cell growth. Insect cells do not require $CO_2$ for growth and can be readily adapted to high-density suspension culture for large-scale expression. Many of the post-translational modification pathways present in mammalian systems are also utilized in insect cells, allowing the production of recombinant protein that is antigenically, immunogenically, and functionally similar to the native mammalian protein.

Baculoviruses are DNA viruses in the family Baculoviridae. These viruses are known to have a narrow host-range that is limited primarily to Lepidopteran species of insects (butterflies and moths). The baculovirus *Autographa californica* Nuclear Polyhedrosis Virus (AcNPV), which has become the prototype baculovirus, replicates efficiently in susceptible cultured insect cells. AcNPV has a double-stranded closed circular DNA genome of about 130,000 base-pairs and is well characterized with regard to host range, molecular biology, and genetics. The Baculovirus Expression Vector System (BEVS) is a safe and rapid method for the abundant production of recombinant proteins in insect cells and insects. Baculovirus expression systems are powerful and versatile systems for high-level, recombinant protein expression in insect cells. Expression levels up to 500 mg/l have been reported using the baculovirus expression system, making it an ideal system for high-level expression. Recombinant baculoviruses that express foreign genes are constructed by way of homologous recombination between baculovirus DNA and chimeric plasmids containing the gene sequence of interest. Recombinant viruses can be detected by virtue of their distinct plaque morphology and plaque-purified to homogeneity.

Recombinant fusion proteins described herein can be produced in insect cells including, but not limited to, cells derived from the Lepidopteran species *S. frugiperda*. Other insect cells that can be infected by baculovirus, such as those from the species *Bombyx mori, Galleria mellanoma, Trichplusia ni*, or *Lamanthria dispar*, can also be used as a suitable substrate to produce recombinant proteins described herein. Baculovirus expression of recombinant proteins is well known in the art. See U.S. Pat. Nos. 4,745,051; 4,879,236; 5,179,007; 5,516,657; 5,571,709; 5,759,809. It will be understood by those skilled in the art that the expression system is not limited to a baculovirus expression system. What is important is that the expression system directs the N-glycosylation of expressed recombinant proteins. The recombinant proteins described herein can also be expressed in other expression systems such as Entomopox viruses (the poxviruses of insects), cytoplasmic polyhedrosis viruses (CPV), and transformation of insect cells with the recombinant gene or genes constitutive expression. A good number of baculovirus transfer vectors and the corresponding appropriately modified host cells are commercially available, for example, pAcGP67, pAcSECG2TA, pVL1392, pVL1393, pAcGHLT, and pAcAB4 from BD Biosciences; pBAC-3, pBAC-6, pBACgus-6, and pBAC-surf-1 from NOVAGEN®, and pPolh-FLAG and pPolh-MAT from SIGMA ALDRICH®.

The region between the promoter and the transcriptional terminator can have multiple restriction enzyme digestion sites for facilitating cloning of the foreign coding sequence, in this instance, the coding DNA sequence for an antigen polypeptide, and a complementary affinity molecule. Additional sequences can be included, e.g., signal peptides and/or tag coding sequences, such as His-tag, MAT-Tag, FLAG tag, recognition sequence for enterokinase, honeybee melittin secretion signal, beta-galactosidase, glutathione S-transferase (GST) tag upstream of the MCS for facilitating the secretion, identification, proper insertion, positive selection of recombinant virus, and/or purification of the recombinant protein.

In some embodiments, the fusion protein can comprise an N-terminal signal sequence as disclosed herein. In some embodiments, the signal sequence is attached to the N-terminal of the complementary affinity molecule as disclosed herein.

In some embodiments, a fusion polypeptide as described herein has a spacer peptide, e.g., a 14-residue spacer (GSP-GISGGGGGILE) (SEQ ID NO: 41) separating antigen from the complementary affinity molecule. The coding sequence of such a short spacer can be constructed by annealing a complementary pair of primers. One of skill in the art can design and synthesize oligonucleotides that will code for the selected spacer. Spacer peptides should generally have nonpolar amino acid residues, such as glycine and proline.

Standard techniques known to those of skill in the art can be used to introduce mutations (to create amino acid substitutions in an antigen polypeptide sequence of the fusion polypeptide described herein, e.g., in the antigen in the nucleotide sequence encoding the fusion polypeptide described herein, including, for example, site-directed mutagenesis and PCR-mediated mutagenesis. Preferably, the variant fusion polypeptide has less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions, inclusive, relative to the fusion polypeptides described herein.

Certain silent or neutral missense mutations can also be made in the DNA coding sequence that do not change the encoded amino acid sequence or the capability to promote transmembrane delivery. These types of mutations are useful to optimize codon usage, or to improve recombinant protein expression and production.

Specific site-directed mutagenesis of a coding sequence for the fusion polypeptide in a vector can be used to create specific amino acid mutations and substitutions. Site-directed mutagenesis can be carried out using, e.g., the QUICKCHANGE® site-directed mutagenesis kit from Stratagene according to the manufacturer's instructions.

In one embodiment, described herein are expression vectors comprising the coding DNA sequence for the polypeptides described herein for the expression and purification of the recombinant polypeptide produced from a protein expression system using host cells selected from, e.g., bacteria, mammalian, insect, yeast, or plant cells. The expression vector should have the necessary 5' upstream and 3' downstream regulatory elements such as promoter sequences, ribosome recognition and TATA box, and 3' UTR AAUAAA transcription termination sequence for efficient gene transcription and translation in its respective host cell. The expression vector is, preferably, a vector having the transcription promoter selected from a group consisting of CMV (cytomegalovirus) promoter, RSV (Rous sarcoma virus) promoter, β-actin promoter, SV40 (simian virus 40) promoter and muscle creatine kinase promoter, and the transcription terminator selected from a group consisting of SV40 poly(A) and BGH terminator; more preferably, an expression vector having the early promoter/enhancer sequence of cytomegalovirus and the adenovirus tripartite leader/intron sequence and containing the replication origin and poly(A) sequence of SV40. The expression vector can have additional coding regions, such as those encoding, for example, 6x-histidine (SEQ ID NO: 10), V5, thioredoxin, glutathione-S-transferase, c-Myc, VSV-G, HSV, FLAG, maltose binding peptide, metal-binding peptide, HA and "secretion" signals (Honeybee melittin, □α-factor, PHO, Bip), which can be incorporated into the expressed fusion polypeptide. In addition, there can be enzyme digestion sites incorporated after these coding regions to facilitate their enzymatic removal if they are not needed. These additional nucleic acids are useful for the detection of fusion polypeptide expression, for protein purification by affinity chromatography, enhanced solubility of the recombinant protein in the host cytoplasm, and/or for secreting the expressed fusion polypeptide out into the culture media or the spheroplast of the yeast cells. The expression of the fusion polypeptide can be constitutive in the host cells or it can be induced, e.g., with copper sulfate, sugars such as galactose, methanol, methylamine, thiamine, tetracycline, infection with baculovirus, and (isopropyl-beta-D-thiogalactopyranoside) IPTG, a stable synthetic analog of lactose.

In another embodiment, the expression vector comprising a polynucleotide described herein is a viral vector, such as adenovirus, adeno-associated virus (AAV), retrovirus, and lentivirus vectors, among others. Recombinant viruses provide a versatile system for gene expression studies and therapeutic applications.

In some embodiments, the fusion polypeptides described herein are expressed from viral infection of mammalian cells. The viral vectors can be, for example, adenovirus, adeno-associated virus (AAV), retrovirus, and lentivirus. A simplified system for generating recombinant adenoviruses is presented by He et al., 95 PNAS 2509 (1998). The gene of interest is first cloned into a shuttle vector, e.g., pAdTrack-CMV. The resultant plasmid is linearized by digesting with restriction endonuclease PmeI, and subsequently cotransformed into E. coli. BJ5183 cells with an adenoviral backbone plasmid, e.g. pADEASY-1 of Stratagene's ADEASY™ Adenoviral Vector System. Recombinant adenovirus vectors are selected for kanamycin resistance, and recombination confirmed by restriction endonuclease analyses. Finally, the linearized recombinant plasmid is transfected into adenovirus packaging cell lines, for example HEK 293 cells (El-transformed human embryonic kidney cells) or 911 (El-transformed human embryonic retinal cells). Fallaux, et al. 7 Human Gene Ther. 215 (1996). Recombinant adenovirus are generated within the HEK 293 cells.

Recombinant lentivirus has the advantage of delivery and expression of fusion polypeptides in dividing and non-dividing mammalian cells. The HIV-1 based lentivirus can effectively transduce a broader host range than the Moloney Leukemia Virus (MoMLV)-based retroviral systems. Preparation of the recombinant lentivirus can be achieved using, for example, the pLenti4N5-DEST™, pLenti6N5-DEST™ or pLenti vectors together with VIRAPOWER™ Lentiviral Expression systems from Invitrogen, Inc.

Recombinant adeno-associated virus (rAAV) vectors are applicable to a wide range of host cells including many different human and non-human cell lines or tissues. rAAVs are capable of transducing a broad range of cell types and transduction is not dependent on active host cell division. High titers, >$10^8$ viral particle/ml, are easily obtained in the supernatant and $10^{11}$-$10^{12}$ viral particle/ml with further concentration. The transgene is integrated into the host genome so expression is long term and stable.

Large scale preparation of AAV vectors is made by a three-plasmid cotransfection of a packaging cell line: AAV vector carrying the coding nucleic acid, AAV RC vector containing AAV rep and cap genes, and adenovirus helper plasmid pDF6, into 50×150 mm plates of subconfluent 293 cells. Cells are harvested three days after transfection, and viruses are released by three freeze-thaw cycles or by sonication.

AAV vectors can be purified by two different methods depending on the serotype of the vector. AAV2 vector is purified by the single-step gravity-flow column purification method based on its affinity for heparin. Auricchio et. al., 12 Human Gene Ther. 71 (2001); Summerford & Samulski, 72 J. Virol. 1438 (1998); Summerford & Samulski, 5 Nat. Med. 587 (1999). AAV2/1 and AAV2/5 vectors are currently purified by three sequential CsCl gradients.

Without wishing to be bound to theory, when proteins are expressed by a cell, including a bacterial cell, the proteins are targeted to a particular part in the cell or secreted from the cell. Thus, protein targeting or protein sorting is the mechanism by which a cell transports proteins to the appropriate positions in the cell or outside of it. Sorting targets can be the inner space of an organelle, any of several interior membranes, the cell's outer membrane, or its exterior via secretion. This delivery process is carried out based on information contained in the protein itself. Correct sorting is crucial for the cell; errors can lead to diseases.

With some exceptions, bacteria lack membrane-bound organelles as found in eukaryotes, but they may assemble proteins onto various types of inclusions such as gas vesicles and storage granules. Also, depending on the species of bacteria, bacteria may have a single plasma membrane (Gram-positive bacteria), or both an inner (plasma) membrane and an outer cell wall membrane, with an aqueous space between the two called the periplasm (Gram-negative bacteria). Proteins can be secreted into the environment, according to whether or not there is an outer membrane. The basic mechanism at the plasma membrane is similar to the eukaryotic one. In addition, bacteria may target proteins into or across the outer membrane. Systems for secreting proteins across the bacterial outer membrane may be quite complex and play key roles in pathogenesis. These systems may be described as type I secretion, type II secretion, etc.

In most Gram-positive bacteria, certain proteins are targeted for export across the plasma membrane and subsequent covalent attachment to the bacterial cell wall. A specialized enzyme, sortase, cleaves the target protein at a characteristic recognition site near the protein C-terminus, such as an LPXTG motif (SEQ ID NO: 42) (where X can be any amino acid), then transfers the protein onto the cell wall. A system analogous to sortase/LPXTG ("LPXTG" disclosed as SEQ ID NO: 42), having the motif PEP-CTERM (SEQ ID NO: 43), termed exosortase/PEP-CTERM ("PEP" disclosed as SEQ ID NO: 43), is proposed to exist in a broad range of Gram-negative bacteria.

Proteins with appropriate N-terminal targeting signals are synthesized in the cytoplasm and then directed to a specific protein transport pathway. During, or shortly after its translocation across the cytoplasmic membrane, the protein is processed and folded into its active form. Then the translocated protein is either retained at the periplasmic side of the cell or released into the environment. Since the signal peptides that target proteins to the membrane are key determinants for transport pathway specificity, these signal peptides are classified according to the transport pathway to which they direct proteins. Signal peptide classification is based on the type of signal peptidase (SPase) that is responsible for the removal of the signal peptide. The majority of exported proteins are exported from the cytoplasm via the general "Secretory (Sec) pathway". Most well known virulence factors (e.g. exotoxins of *Staphylococcus aureus*, protective antigen of *Bacillus anthracis*, lysteriolysin O of *Listeria monocytogenes*) that are secreted by Gram-positive pathogens have a typical N-terminal signal peptide that would lead them to the Sec-pathway. Proteins that are secreted via this pathway are translocated across the cytoplasmic membrane in an unfolded state. Subsequent processing and folding of these proteins takes place in the cell wall environment on the trans-side of the membrane. In addition to the Sec system, some Gram-positive bacteria also contain the Tat-system that is able to translocate folded proteins across the membrane. Pathogenic bacteria may contain certain special purpose export systems that are specifically involved in the transport of only a few proteins. For example, several gene clusters have been identified in mycobacteria that encode proteins that are secreted into the environment via specific pathways (ESAT-6) and are important for mycobacterial pathogenesis. Specific ATP-binding cassette (ABC) transporters direct the export and processing of small antibacterial peptides called bacteriocins. Genes for endolysins that are responsible for the onset of bacterial lysis are often located near genes that encode for holin-like proteins, suggesting that these holins are responsible for endolysin export to the cell wall. Wooldridge, BACT. SECRETED PROTS: SECRETORY MECHS. & ROLE IN PATHOGEN. (Caister Academic Press, 2009)

In some embodiments, the signal sequence useful in the present invention is OmpA Signal sequence, however any signal sequence commonly known by persons of ordinary skill in the art which allows the transport and secretion of antimicrobial agents outside the bacteriophage infected cell are encompassed for use in the present invention.

Signal sequence that direct secretion of proteins from bacterial cells are well known in the art, for example as disclosed in International application WO 2005/071088. For example, one can use some of the non-limited examples of signal peptide shown in Table 4, which can be attached to the amino-terminus or carboxyl terminus of the antimicrobial peptide (Amp) or antimicrobial polypeptide to be expressed by the antimicrobial-agent engineered bacteriophage, e.g., AMP-engineered bacteriophage. Attachment can be via fusion or chimera composition with selected antigen or antigen-complementary affinity molecule fusion protein resulting in the secretion from the bacterium infected with the antimicrobial-agent engineered bacteriophage, e.g. AMP-engineered bacteriophage.

TABLE 4

Example signal peptides to direct secretion of a protein or peptide antigen or antigen-complementary affinity molecule fusion protein of a bacterial cell

| Secretion Pathway | Signal Peptide Amino Acid sequence (NH$_2$-CO$_2$) | Gene | Genus/Species |
|---|---|---|---|
| secA1 | MKKIMLVITLILVSPIAQQTEAKD (SEQ ID NO: 44) | Hly (LLO) | Listeria monocytogenes |
|  | MKKKIISAILMSTVILSAAAPLSGVYADT (SEQ ID NO: 45) | Usp45 | Lactococcus lactis |
|  | MKKRKVLIPLMALSTILVSSTGNLEVIQAEV (SEQ ID NO: 46) | Pag (protective antigen) | Bacillus anthracis |
| secA2 | MNMKKATIAATAGIAVTAFAAPTIASAST (SEQ ID NO: 47) | lap (invasion-associated protein p60) | Listeria monocytogenes |
|  | MQKTRKERILEALQEEKKNKKSKKFKTGATIAGVTAIATSITVPGIEVIVSADE (SEQ ID NO: 48) | NamA lmo2691 (autolysin) | Listeria monocytogenes |
|  | MKKLKMASCALVAGLMFSGLTPNAFAED (SEQ ID NO: 49) | *BA_0281 (NLP/P60 family) | Bacillus anthracis |
|  | MAKKFNYKLPSMVALTLVGSAVTAHQVQAAE (SEQ ID NO: 50) | * atl (autolysin) | Staphylococcus aureus |
| Tat | MTDKKSENQTEKTETKENKGMTRREMLKLSAVAGTGIAVGATGLGTILNVVDQVDKALT (SEQ ID NO: 51) | lmo0367 | Listeria monocytogenes |
|  | MAYDSRFDEWVQKLKEESFQNNTFDRRKFIQGAGKIAGLGLGLTIAQSVGAFG (SEQ ID NO: 52 ) | PhoD (alkaline phosphatase) | Bacillus subtillis |

The polypeptides as described herein, e.g., antigens or antigen-complementary affinity molecule fusion protein can be expressed and purified by a variety methods known to one skilled in the art, for example, the fusion polypeptides described herein can be purified from any suitable expression system. Fusion polypeptides can be purified to substantial purity by standard techniques, including selective precipitation with such substances as ammonium sulfate; column chromatography, immunopurification methods, and others; which are well-known in the art. See, e.g., Scopes, PROTEIN PURIFICATION: PRINCIPLES & PRACTICE (1982); U.S. Pat. No. 4,673,641.

A number of procedures can be employed when recombinant proteins are purified. For example, proteins having established molecular adhesion properties can be reversibly fused to the protein of choice. With the appropriate ligand, the protein can be selectively adsorbed to a purification column and then freed from the column in a relatively pure form. The fused protein is then removed by enzymatic activity. Finally, the protein of choice can be purified using affinity or immunoaffinity columns.

After the protein is expressed in the host cells, the host cells can be lysed to liberate the expressed protein for purification. Methods of lysing the various host cells are featured in "Sample Preparation-Tools for Protein Research" EMD Bioscience and in the Current Protocols in Protein Sciences (CPPS). An example purification method is affinity chromatography such as metal-ion affinity chromatograph using nickel, cobalt, or zinc affinity resins for histidine-tagged fusion polypeptides. Methods of purifying histidine-tagged recombinant proteins are described by Clontech using their TALON® cobalt resin and by NOVAGEN® in their pET system manual, 10th edition. Another preferred purification strategy is immuno-affinity chromatography, for example, anti-myc antibody conjugated resin can be used to affinity purify myc-tagged fusion polypeptides. When appropriate protease recognition sequences are present, fusion polypeptides can be cleaved from the histidine or myc tag, releasing the fusion polypeptide from the affinity resin while the histidine-tags and myc-tags are left attached to the affinity resin.

Standard protein separation techniques for purifying recombinant and naturally occurring proteins are well known in the art, e.g., solubility fractionation, size exclusion gel filtration, and various column chromatography.

Solubility Fractionation:

Often as an initial step, particularly if the protein mixture is complex, an initial salt fractionation can separate many of the unwanted host cell proteins (or proteins derived from the cell culture media) from the protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Exclusion Filtration:

The molecular weight of the protein of choice can be used to isolate it from proteins of greater and lesser size using ultrafiltration through membranes of different pore size (for example, AMICON® or MILLIPORE® membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column chromatography: The protein of choice can also be separated from other proteins on the basis of its size, net surface charge, hydrophobicity, and affinity for ligands. In addition, antibodies raised against recombinant or naturally occurring proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech). For example, an antigen polypeptide can be purified using a PA63 heptamer affinity column. Singh et al., 269, J. Biol. Chem. 29039 (1994).

In some embodiments, a combination of purification steps comprising, for example: (a) ion exchange chromatography, (b) hydroxyapatite chromatography, (c) hydrophobic interaction chromatography, and (d) size exclusion chromatography can be used to purify the fusion polypeptides described herein.

Cell-free expression systems are also contemplated. Cell-free expression systems offer several advantages over traditional cell-based expression methods, including the easy modification of reaction conditions to favor protein folding, decreased sensitivity to product toxicity and suitability for high-throughput strategies such as rapid expression screening or large amount protein production because of reduced reaction volumes and process time. The cell-free expression system can use plasmid or linear DNA. Moreover, improvements in translation efficiency have resulted in yields that exceed a milligram of protein per milliliter of reaction mix. Commercially available cell-free expression systems include the TNT coupled reticulocyte lysate Systems (Promega) which uses rabbit reticulocyte-based in vitro system.

Formulations of an Immune Composition and Methods of Use

Specific embodiments of the present invention provide for use of the immunogenic compositions as disclosed herein to elicit an immune response in an animal. More specifically, the compositions elicit both humoral and cellular immunity, and in many instance mucosal immunity. Embodiments of the present invention provide at least partial protection from or partial improvement after infection by, in particular, pneumococcus. Pneumococci cause a number of diseases, such as meningitis, pneumonia, bacteremia, and otitis media. Almost one million children die of pneumococcal diseases worldwide every year. *S. pneumoniae* have been studied extensively, and at least some of the genomes sequenced. See, e.g., U.S. Pat. No. 7,141,418. Although antibodies to the capsular polysaccharides, which define the known serotypes, confer serotype-specific protection, other protective mechanisms of immunity have been described. See Malley et al., 88 J. Mol. Med. 135 (2010). These other protective mechanisms include, but are not limited to, antibodies to noncapsular antigens and T cell responses to pneumococcal constituents. The application of protein-polysaccharide conjugate vaccine, PCV7, has reduced diseases significantly. Black et al., 24(S2) Vaccine 79 (2006); Hansen et al., 25 Pediatr. Infect. Dis. J. 779 (2006)). Yet, recent studies have shown that the lack of other serotypes in PCV7 has resulted in emerging replacement pneumococcal serotypes. Pichichero & Casey, 26(S10) Pediatr. Infect. Dis. J. S12 (2007).

Certain pneumococcal antigens common to all serotypes of the species have been shown to have immunoprotective potential despite the encapsulation, e.g., the surface proteins PspA, PspC, PsaA and the cytotoxin pneumolysin or pneumolysoid mutants (Basset et al., 75 Infect. Immun. 5460 (2007); Briles et al., 18 Vaccine 1707 (2000)); the use of genomics and mutational libraries has identified several dozen additional species-common proteins (Hava & Camilli, 45 Mol. Microbiol. 1389 (2002); Wizemann et al., 60 Infect. Immun. 1593 (2001)). Immunity has been induced by individual antigens in animal models (Alexander et al., 62 Infect. Immun. 5683 (1994); Balachandran et al., 70 Infect. Immun. 2526 (2002); Chung et al., 170 J. Immunol. 1958 (2003); Glover et al., 76 Infect. Immun. 2767 (2008); Wu et al., 175 J. Infect. Dis. 839 (1997)), but no vaccine based on a common antigen has been approved for human use to date.

In one embodiment, provided herein is a method of vaccinating a mammal comprising administering the immunogenic composition comprising at least one, or multiple antigens attached to at least one type of polymer scaffold, e.g., a polysaccharide or carbohydrate polymer for use in eliciting an immune response to the one or more antigens attached to the polymer when administered to a subject. In some embodiments, the immune response is a humoral and/or cellular immune response.

Accordingly, one aspect of the present invention relates to methods to elicit an immune response in a subject, comprising administering to the subject an immunogenic composition comprising at least one type of the polymer, e.g., a polysaccharide, at least one antigen, and at least one complementary affinity-molecule pair comprising (i) a first affinity molecule which associates with the polymer, e.g., a polysaccharide, and (ii) a complementary affinity molecule which associates with the antigen, to attach the antigen to the polymer, e.g., a polysaccharide, (e.g., the first affinity molecule associates with the complementary affinity molecule to link the antigen to the polymer, e.g., polysaccharide).

Accordingly, one aspect of the present invention relates to methods to elicit a humoral and/or cellular immunity to multiple antigens at the same time, e.g., where the immunogenic composition administered to the subject comprises a polymer comprising at least 1, or at least 2, or a more, e.g., a plurality of the same or different antigens.

One aspect of the present invention relates to a method of immunization or vaccinating a subject, e.g., a bird or a mammal, e.g., a human against a pathogen comprises administering an immune composition as disclosed herein comprising at least one antigen derived from one or more pathogens. In some embodiments, a subject can be immunized against at least 1, or at least 2, or at least 2, or at least 3, or at least 5, or at least 10, or at least 15, or at least about 20, or at least 50, or at least about 100, or more than 100 different pathogens at the same time, where the polymer of the immunogenic composition as the corresponding different antigens attached.

In some embodiments, a subject can be administered several different immunogenic compositions as disclosed herein, for example, a subject can be administered a composition comprising a polymer with an antigen, or a plurality of antigens, e.g., antigens A, B, C, and D etc., and also administered a composition comprising a polymer comprising a different antigen, or a different set of antigens, e.g., antigens W, X, Y, and Z etc. Alternatively, a subject can be administered a composition comprising a polymer A with an antigen, or a plurality of antigens, e.g., antigens A, B, C, and D, etc., and also administered a composition comprising a polymer B comprising the same e.g., antigens A, B, C, and D etc., or a different set of antigens. It is envisioned that the present invention provides a methods for the immunization of a subject with as many antigens as desired, e.g., with a variety of different immunogenic complexes as described herein, to enable immunization with as many as 100 or more antigens.

In one embodiment, the immunogenic compositions as described herein comprise a pharmaceutically acceptable carrier. In another embodiment, the immunogenic composition composition described herein is formulated for administering to a bird, mammal, or human, as or in a vaccine. Suitable formulations can be found in, for example, Remington's Pharmaceutical Sciences (2006), or Introduction to Pharmaceutical Dosage Forms (4th ed., Lea & Febiger, Philadelphia, 1985).

In one embodiment, the immunogenic compositions as described herein comprise pharmaceutically acceptable carriers that are inherently nontoxic and nontherapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. For all administrations, conventional depot forms are suitably used. Such forms include, for example, microcapsules, nano-capsules, liposomes, plasters, inhalation forms, nose sprays, sublingual tablets, and sustained release preparations. For examples of sustained release compositions, see U.S. Pat. Nos. 3,773,919, 3,887,699, EP 58,481A, EP 158, 277A, Canadian Patent No. 1176565; Sidman et al., 22 Biopolymers 547 (1983); Langer et al., 12 Chem. Tech. 98 (1982). The proteins will usually be formulated at a concentration of about 0.1 mg/ml to 100 mg/ml per application per patient.

In one embodiment, other ingredients can be added to vaccine formulations, including antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

In some embodiments, the present MAPS immunogen compositions are administered with at least one adjuvant. Adjuvants are a heterogeneous group of substances that enhance the immunological response against an antigen that is administered simultaneously. In some instances, adjuvants improve the immune response so that less vaccine is needed. Adjuvants serve to bring the antigen—the substance that stimulates the specific protective immune response—into contact with the immune system and influence the type of immunity produced, as well as the quality of the immune response (magnitude or duration). Adjuvants can also decrease the toxicity of certain antigens; and provide solubility to some vaccine components. Almost all adjuvants used today for enhancement of the immune response against antigens are particles or form particles together with the antigen. In the book Vaccine Design—Subunit & Adjuvant Approach (Powell & Newman, Eds., Plenum Press, 1995), many known adjuvants are described both regarding their immunological activity and regarding their chemical characteristics. The type of adjuvants that do not form particles are a group of substances that act as immunological signal substances and that under normal conditions consist of the substances that are formed by the immune system as a consequence of the immunological activation after administration of particulate adjuvant systems.

Adjuvants for immunogenic compositions and vaccines are well known in the art. Examples include, but not limited to, monoglycerides and fatty acids (e.g. a mixture of monoolein, oleic acid, and soybean oil); mineral salts, e.g., aluminium hydroxide and aluminium or calcium phosphate gels; oil emulsions and surfactant based formulations, e.g., MF59 (microfluidised detergent stabilised oil-in-water emulsion), QS21 (purified saponin), AS02 [SBAS2] (oil-in-water emulsion+MPL+QS-21), MPL-SE, Montanide ISA-51 and ISA-720 (stabilised water-in-oil emulsion); particulate adjuvants, e.g., virosomes (unilamellar liposomal vehicles incorporating influenza haemagglutinin), ASO4 ([SBAS4] Al salt with MPL), ISCOMS (structured complex of saponins and lipids), polylactide co-glycolide (PLG); microbial derivatives (natural and synthetic), e.g., monophosphoryl lipid A (MPL), Detox (MPL+M. Phlei cell wall skeleton), AGP [RC-529] (synthetic acylated monosaccharide), Detox-PC, DC_Chol (lipoidal immunostimulators able to self-organize into liposomes), OM-174 (lipid A derivative), CpG motifs (synthetic oligonucleotides containing immunostimulatory CpG motifs), or other DNA structures, modified LT and CT (genetically modified bacterial toxins to provide non-toxic adjuvant effects); endogenous human immunomodulators, e.g., hGM-CSF or hIL-12 (cytokines that can be administered either as protein or plasmid encoded), Immudaptin (C3d tandem array), MoGM-CSF, TiterMax-G, CRL-1005, GERBU, TERamide, PSC97B, Adjumer, PG-026, GSK-I, GcMAF, B-alethine, MPC-026, Adjuvax, CpG ODN, Betafectin, Alum, and MF59 and inert vehicles, such as gold particles. Additional adjuvants are known in the art, see, e.g., U.S. Pat. No. 6,890,540; U. S. Patent Pub. No. 2005; 0244420; PCT/SE97/01003.

In some embodiments an adjuvant is a particulate and can have a characteristic of being slowly biodegradable. Care must be taken to ensure that that the adjuvant do not form toxic metabolites. Preferably, in some embodiments, such adjuvants can be matrices used are mainly substances originating from a body. These include lactic acid polymers, poly-amino acids (proteins), carbohydrates, lipids and biocompatible polymers with low toxicity. Combinations of these groups of substances originating from a body or combinations of substances originating from a body and biocompatible polymers can also be used. Lipids are the preferred substances since they display structures that make them biodegradable as well as the fact that they are a critical element in all biological membranes.

In one embodiment, the immunogenic compositions as described herein for administration must be sterile for administration to a subject. Sterility is readily accomplished by filtration through sterile filtration membranes (e.g., 0.2 micron membranes), or by gamma irradiation.

In some embodiments, the immunogenic compositions described herein further comprise pharmaceutical excipients including, but not limited to biocompatible oils, physiological saline solutions, preservatives, carbohydrate, protein, amino acids, osmotic pressure controlling agents, carrier gases, pH-controlling agents, organic solvents, hydrophobic agents, enzyme inhibitors, water absorbing polymers, surfactants, absorption promoters and anti-oxidative agents. Representative examples of carbohydrates include soluble sugars such as hydropropyl cellulose, carboxymethyl cellulose, sodium carboxyl cellulose, hyaluronic acid, chitosan, alginate, glucose, xylose, galactose, fructose, maltose, saccharose, dextran, chondroitin sulfate, etc. Representative examples of proteins include albumin, gelatin, etc. Representative examples of amino acids include glycine, alanine, glutamic acid, arginine, lysine, and their salts. Such pharmaceutical excipients are well-known in the art.

In some embodiments, the immunogenic MAPS composition is administered in combination with other therapeutic ingredients including, e.g., γ-interferon, cytokines, chemotherapeutic agents, or anti-inflammatory, or anti-viral agents. In some embodiments, the immunogenic composition as disclosed herein can be administered with one or more co-stimulatory molecules and/or adjuvants as disclosed herein.

In some embodiments, the immunogenic composition is administered in a pure or substantially pure form, but may be administered as a pharmaceutical composition, formulation or preparation. Such formulation comprises MAPS described herein together with one or more pharmaceutically acceptable carriers and optionally other therapeutic ingredients. Other therapeutic ingredients include compounds that enhance antigen presentation, e.g., gamma interferon, cytokines, chemotherapeutic agents, or anti-inflammatory agents. The formulations can conveniently be presented in unit dosage form and may be prepared by methods well known in the pharmaceutical art. For example, Plotkin and Mortimer, in VACCINES (2nd ed., W.B. Saunders Co., 1994) describes vaccination of animals or humans to induce an immune response specific for particular pathogens, as well as methods of preparing antigen, determining a suitable dose of antigen, and assaying for induction of an immune response.

Formulations suitable for intravenous, intramuscular, intranasal, oral, sublingual, vaginal, rectal, subcutaneous, or intraperitoneal administration conveniently comprise sterile aqueous solutions of the active ingredient with solutions which are preferably isotonic with the blood of the recipient. Such formulations may be conveniently prepared by dissolving solid active ingredient in water containing physiologically compatible substances such as sodium chloride (e.g., 0.1M-2.0 M), glycine, and the like, and having a buffered pH compatible with physiological conditions to produce an aqueous solution, and rendering the solution sterile. These may be present in unit or multi-dose containers, for example, sealed ampoules or vials.

Liposomal suspensions can also be used as pharmaceutically acceptable carriers. These can be prepared according to methods known to those skilled in the art, for example, as described in U.S. Pat. No. 4,522,811.

Formulations for an intranasal delivery are described in U.S. Pat. Nos. 5,427,782; 5,843,451; 6,398,774.

The formulations of the immunogenic compositions can incorporate a stabilizer. Illustrative stabilizers are polyethylene glycol, proteins, saccharide, amino acids, inorganic acids, and organic acids which may be used either on their own or as admixtures. Two or more stabilizers may be used in aqueous solutions at the appropriate concentration and/or pH. The specific osmotic pressure in such aqueous solution is generally in the range of 0.1-3.0 osmoses, preferably in the range of 0.80-1.2. The pH of the aqueous solution is adjusted to be within the range of pH 5.0-9.0, preferably within the range of pH 6-8.

When oral preparations are desired, the immunogenic compositions can be combined with typical carriers, such as lactose, sucrose, starch, talc magnesium stearate, crystalline cellulose, methyl cellulose, carboxymethyl cellulose, glycerin, sodium alginate or gum arabic among others.

In some embodiments, the immunogenic compositions as described herein can be administered intravenously, intranasally, intramuscularly, subcutaneously, intraperitoneally, sublingually, vaginal, rectal or orally. In some embodiments, the route of administration is oral, intranasal, subcutaneous, or intramuscular. In some embodiments, the route of administration is intranasal administration.

Vaccination can be conducted by conventional methods. For example, an immunogenic compositions can be used in a suitable diluent such as saline or water, or complete or incomplete adjuvants. The immunogenic composition can be administered by any route appropriate for eliciting an immune response. The immunogenic composition can be administered once or at periodic intervals until an immune response is elicited. Immune responses can be detected by a variety of methods known to those skilled in the art, including but not limited to, antibody production, cytotoxicity assay, proliferation assay and cytokine release assays. For example, samples of blood can be drawn from the immunized mammal, and analyzed for the presence of antibodies against the antigens of the immunogenic composition by ELISA (see de Boer et. al., 115 Arch Virol. 147 (1990) and the titer of these antibodies can be determined by methods known in the art.

The precise dose to be employed in the formulation will also depend on the route of administration and should be decided according to the judgment of the practitioner and each patient's circumstances. For example, a range of 25 μg-900 μg total protein can be administered monthly for three months.

Ultimately, the attending physician will decide the amount of immunogenic composition or vaccine composition to administer to particular individuals. As with all immunogenic compositions or vaccines, the immunologically effective amounts of the immunogens must be determined empirically. Factors to be considered include the immunogenicity, whether or not the immunogen will be complexed with or covalently attached to an adjuvant or carrier protein or other carrier, routes of administrations and the number of immunizing dosages to be administered. Such factors are known in the vaccine art and it is well within the skill of immunologists to make such determinations without undue experimentation.

In one embodiment, an immunogenic composition or vaccine composition as described herein, when administered to mice, can provoke an immune response that prevents a disease symptom in at least 20% of animals challenged with 5 $LD_{50}$ of the immunogenic composition comprising antigens to which the disease symptom is prevented. Methods of vaccination and challenging an immunized animal are known to one skilled in the art. For example, a 10 μg aliquot of an immunogenic composition or vaccine composition as disclosed herein can be prepared in 100 μl PBS and/or with addition of incomplete Freund's adjuvant and injected intramuscularly per mouse per vaccination. Alternatively, parenteral, intraperitoneal and footpad injections can be used. Volumes of footpad injections are reduced to 50 μl. Mice can be immunized with an immunogenic composition or vaccine composition as disclosed herein on three separate occasions with several days, e.g., 14 days interval in between.

Efficacy of vaccination can be tested by challenge with the pathogen. Seven days after the last dose of an immunogenic composition, the immunized mice are challenged intranasally with a pathogenic organism from which the antigen was derived. Ether anaesthetized mice (10 g to 12 g) can be infected intranasally with 50 μl of PBS-diluted allantoic fluid containing 5 LD$_{50}$ of the pathogenic organism. Protection can be measured by monitoring animal survival and body weight, which is assessed throughout an observation period of 21 days. Severely affected mice are euthanized. One LD$_{50}$ of A/Mallard/Pennsylvania/10218/84 is equal to 100-1000 the Tissue Culture Infectious Dose50 (TCID50) assay.

In other embodiments, the immunized mice can be challenged with a variety of different pathogenic organisms, e.g., different pathogenic organisms from which each of the antigens attached to the polymer are derived. For example, of an immunogenic composition comprises five different antigens attached to the polymer, e.g., polysaccharide, where each antigen is derived from five different pathogenic organisms, the immunized mice can be challenged with each of the five different pathogenic organisms, either sequentially (in any order) or concurrently. One skilled in the art would be able to determine the LD$_{50}$ for each pathogenic organism used to challenge the immunized mice by methods known in the art. See, e.g., LaBarre & Lowy, 96 J. Virol. Meths. 107 (2001); Golub, 59 J. Immunol. 7 (1948).

Kits

The present invention also provides for kits for producing an immunogenic composition as disclosed herein which is useful for an investigator to tailor an immunogenic composition with their preferred antigens, e.g., for research purposes to assess the effect of an antigen, or a combination of antigens on immune response. Such kits can be prepared from readily available materials and reagents. For example, such kits can comprise any one or more of the following materials: a container comprising a polymer, e.g., a polysaccharide, cross-linked with a plurality of first affinity molecules; and a container comprising a complementary affinity molecule which associates with the first affinity molecule, wherein the complementary affinity molecule associates with an antigen.

In another embodiment, the kit can comprise a container comprising a polymer, e.g., a polysaccharide, a container comprising a plurality of first affinity molecules, and a container comprising a cross-linking reagent for cross-linking the first affinity molecules to the polymer.

In some embodiments, the kit further comprises a means to attach the complementary affinity molecule to the antigen, where the means can be by a cross-linking reagent or by some intermediary fusion protein. In some embodiments, the kit can comprise at least one co-stimulation factor which can be added to the polymer. In some embodiments, the kit comprises a cross-linking reagent, for example, but not limited to, CDAP (1-cyano-4-dimethylaminopyridinium tetrafluoroborate), EDC (1-Ethyl-3-[3-dimethylaminopropyl] carbodiimide hydrochloride), sodium cyanoborohydride; cyanogen bromide; ammonium bicarbonate/iodoacetic acid for linking the co-factor to the polymer.

A variety of kits and components can be prepared for use in the methods described herein, depending upon the intended use of the kit, the particular target antigen and the needs of the user.

The invention can be further described any of the embodiments in the following numbered paragraphs:

1. A soluble biotin-binding protein, comprising an amino acid sequence (SEQ ID NO: 1)
FDASNFKDFSSIASASSSWQNQSGSTMIIQVDSFGNVSGQYVNRAQGTG

CQNSPYPLTGRVNGTFIAFSVGWNNSTENCNSATGWTGYAQVNGNNTEI

VTSWNLAYEGGSGPAIEQGQDTFQYVPTTENKSLLKD and any functional derivatives thereof.

2. The biotin-binding of paragraph 1, wherein the biotin-binding protein is produced in soluble form at a level of at least 10 mg/L of culture media in *E. coli*.
3. The biotin binding protein of any of claims 1-2, wherein the biotin-binding protein is a dimer.
4. The biotin-binding protein of any of claims 1-3, wherein the biotin-binding protein comprises a bacterial signal sequence at the N-terminus.
5. The biotin-binding protein of paragraph 4, wherein the bacterial signal sequence is (SEQ ID No: 2)
MKKIWLALAGLVLAFSASA.

6. The biotin-binding protein of any of paragraph 4 or 5, wherein the signal sequence is linked to the biotin-protein by a peptide linker.
7. The biotin-binding protein of paragraph 6, wherein the peptide linker comprises the amino acid sequence (SEQ ID NO: 8)
AQDP
or
(SEQ ID NO: 9)
VSDP.

8. The biotin-binding protein of any of claims 1-7, wherein the biotin-binding protein comprises a purification tag at the C-terminus.
9. The biotin-binding protein of paragraph 8, wherein the purification tag is selected from the group consisting of a histidine tag, a c-my tag, a Halo tag, a Flag tag, and any combinations thereof.
10. The biotin-binding protein of paragraph 9, wherein the histidine tag comprises the amino acid sequence (SEQ ID NO: 10)
HHHHHH.

11. The biotin-binding protein of any of claims 8-10, wherein the purification tag is linked to the biotin-binding protein via a peptide linker.
12. The biotin-binding protein of paragraph 11, where the peptide linker comprises the amino acid sequence VDK-LAAALE (SEQ ID NO: 11) or GGGGSSSVDK-LAAALE (SEQ ID NO: 12).
13. The biotin-binding protein of any of paragraph 1-12, wherein the biotin-binding protein comprises the amino acid sequence (SEQ ID NO: 15)
MKKIWLALAGLVLAFSASAAQDPFDASNFKDFSSIASASSSWQNQSGSTM

IIQVDSFGNVSGQYVNRAQGTGCQNSPYPLTGRVNGTFIAFSVGWNNSTE

-continued

NCNSATGWTGYAQVNGNNTEIVTSWNLAYEGGSGPAIEQGQDTFQYVPTT

ENKSLLKDGGGGSSSVDKLAAALEFIREIREIH.

14. A composition comprising a biotin-binding protein of any of claims 1-13.
15. A fusion protein comprising a biotin-binding protein and a protein or a peptide.
16. The fusion protein of paragraph 15, wherein the protein or peptide is fused to the biotin-binding protein by a peptide linker.
17. The fusion protein of paragraph 15, wherein the peptide linker comprises the amino acid sequence (SEQ ID NO: 22)
GGGGSSS.

18. The fusion protein of any of claims 15-17, wherein the protein or peptide is an antigen selected from the group consisting of: pneumococcal antigens, tuberculosis antigens, anthrax antigens, HIV antigens, seasonal or epidemic flu antigens, *influenzae* antigens, Pertussis antigens, *Staphylococcus aureus* antigens, Meningococcal antigens, *Haemophilus* antigens, HPV antigens, or combinations thereof.
19. The fusion protein of any of claims 15-18, wherein the antigen is a non-hemolytic variant of *S. aureus* alpha-hemolysin.
20. The fusion of paragraph 19, wherein the non-hemolytic variant of *S. aureus* alpha-hemolysin comprises a mutation at amino acid residue 205, 213 or 209-211 of wild-type *S. aureus* alpha-hemolysin.
21. The fusion protein of paragraph 19, wherein the non-hemolytic variant of *S. aureus* alpha-hemolysin comprises one of the following mutations in the wild-type *S. aureus* alpha-hemolysin: (i) residue 205 W to A; (ii) residue 213 W to A; or (iii) residues 209-211 DRD to AAA.
22. The fusion protein of paragraph 19, wherein the non-hemolytic variant of *S. aureus* alpha-hemolysin comprises the amino acid sequence selected from the group consisting of:

(i) W205A
(SEQ ID NO: 23)
ADSDINIKTGTTDIGSNTTVKTGDLVTYDKENGMHKKVFYSFIDDKNHN

KKLLVIRTKGTIAGQYRVYSEEGANKSGLAWPSAFKVQLQLPDNEVAQI

SDYYPRNSIDTKEYMSTLTYGFNGNVTGDDTGKIGGLIGANVSIGHTLK

YVQPDFKTILESPTDKKVGWKVIFNNMVNQNAGPYDRDSWNPVYGNQLF

MKTRNGSMKAADNFLDPNKASSLLSSGFSPDFATVITMDRKASKQQTNI

DVIYERVRDDYQLHWTSTNWKGTNTKDKWIDRSSERYKIDWEKEEMTN;

(ii) W213A
(SEQ ID NO: 24)
ADSDINIKTGTTDIGSNTTVKTGDLVTYDKENGMHKKVFYSFIDDKNHN

KKLLVIRTKGTIAGQYRVYSEEGANKSGLAWPSAFKVQLQLPDNEVAQI

SDYYPRNSIDTKEYMSTLTYGFNGNVTGDDTGKIGGLIGANVSIGHTLK

YVQPDFKTILESPTDKKVGWKVIFNNMVNQNWGPYDRDSANPVYGNQLF

MKTRNGSMKAADNFLDPNKASSLLSSGFSPDFATVITMDRKASKQQTNI

DVIYERVRDDYQLHWTSTNWKGTNTKDKWIDRSSERYKIDWEKEEMTN;

(iii) DRD209-211AAA
(SEQ ID NO: 25)
ADSDINIKTGTTDIGSNTTVKTGDLVTYDKENGMHKKVFYSFIDDKNHN

KKLLVIRTKGTIAGQYRVYSEEGANKSGLAWPSAFKVQLQLPDNEVAQI

SDYYPRNSIDTKEYMSTLTYGFNGNVTGDDTGKIGGLIGANVSIGHTLK

YVQPDFKTILESPTDKKVGWKVIFNNMVNQNWGPYAAASWNPVYGNQLF

MKTRNGSMKAADNFLDPNKASSLLSSGFSPDFATVITMDRKASKQQTNI

DVIYERVRDDYQLHWTSTNWKGTNTKDKWIDRSSERYKIDWEKEEMTN;

and functional variants, portions, and derivatives thereof.

23. The fusion protein of any of claims 15-22, wherein the fusion protein comprises a bacterial signal sequence at the N-terminus.
24. The fusion protein of paragraph 23, wherein the bacterial signal sequence is (SEQ ID No: 2)
MKKIWLALAGLVLAFSASA.

25. The fusion protein of any of paragraph 23 or 24, wherein the signal sequence is linked to the biotin-protein by a peptide linker.
26. The fusion protein of paragraph 25, wherein the peptide linker comprises the amino acid sequence (SEQ ID NO: 8)
AQDP
or
(SEQ ID NO: 9)
VSDP.

27. The fusion protein of any of claims 15-26, wherein the fusion protein comprises a purification tag at the C-terminus.
28. The fusion protein of paragraph 27, wherein the purification tag is selected from the group consisting of a histidine tag, a c-my tag, a Halo tag, a Flag tag, and any combinations thereof.
29. The fusion protein of paragraph 27, wherein the histidine tag comprises the amino acid sequence HHHHHH (SEQ ID NO: 10).
30. The fusion protein of any of claims 27-29, wherein the purification tag is linked to the biotin-binding protein via a peptide linker.
31. The fusion protein of paragraph 30, where the peptide linker comprises the amino acid sequence (SEQ ID NO: 11)
VDKLAAALE.

32. The fusion protein of any of claims 15-31, wherein the biotin-binding protein is a biotin-binding protein of any of claims 1-13.
33. The fusion protein of any of claims 15-32, wherein the fusion protein comprises the amino acid sequence selected from the group consisting of:

(i) W205A (SEQ ID NO: 26)
MKKIWLALAGLVLAFSASAAQDPFDASNFKDFSSIASASSSWQNQSGSTM
IIQVDSFGNVSGQYVNRAQGTGCQNSPYPLTGRVNGTFIAFSVGWNNSTE
NCNSATGWTGYAQVNGNNTEIVTSWNLAYEGGSGPAIEQGQDTFQYVPTT
ENKSLLKDGGGGSSSADSDINIKTGTTDIGSNTTVKTGDLVTYDKENGMH
KKVFYSFIDDKNHNKKLLVIRTKGTIAGQYRVYSEEGANKSGLAWPSAFK
VQLQLPDNEVAQISDYYPRNSIDTKEYMSTLTYGFNGNVTGDDTGKIGGL
IGANVSIGHTLKYVQPDFKTILESPTDKKVGWKVIFNNMVNQNAGPYDRD
SWNPVYGNQLFMKTRNGSMKAADNFLDPNKASSLLSSGFSPDFATVITMD
RKASKQQTNIDVIYERVRDDYQLHWTSTNWKGTNTKDKWIDRSSERYKID
WEKEEMTNVDKLAAALEHHHHHH;

(ii) W213A (SEQ ID NO: 27)
MKKIWLALAGLVLAFSASAAQDPFDASNFKDFSSIASASSSWQNQSGSTM
IIQVDSFGNVSGQYVNRAQGTGCQNSPYPLTGRVNGTFIAFSVGWNNSTE
NCNSATGWTGYAQVNGNNTEIVTSWNLAYEGGSGPAIEQGQDTFQYVPTT
ENKSLLKDGGGGSSSADSDINIKTGTTDIGSNTTVKTGDLVTYDKENGMH
KKVFYSFIDDKNHNKKLLVIRTKGTIAGQYRVYSEEGANKSGLAWPSAFK
VQLQLPDNEVAQISDYYPRNSIDTKEYMSTLTYGFNGNVTGDDTGKIGGL
IGANVSIGHTLKYVQPDFKTILESPTDKKVGWKVIFNNMVNQNWGPYDRD
SANPVYGNQLFMKTRNGSMKAADNFLDPNKASSLLSSGFSPDFATVITMD
RKASKQQTNIDVIYERVRDDYQLHWTSTNWKGTNTKDKWIDRSSERYKID
WEKEEMTNVDKLAAALEHHHHHH;

(iii) DRD209-211AA (SEQ ID NO: 28)
MKKIWLALAGLVLAFSASAAQDPFDASNFKDFSSIASASSSWQNQSGSTM
IIQVDSFGNVSGQYVNRAQGTGCQNSPYPLTGRVNGTFIAFSVGWNNSTE
NCNSATGWTGYAQVNGNNTEIVTSWNLAYEGGSGPAIEQGQDTFQYVPTT
ENKSLLKDGGGGSSSADSDINIKTGTTDIGSNTTVKTGDLVTYDKENGMH
KKVFYSFIDDKNHNKKLLVIRTKGTIAGQYRVYSEEGANKSGLAWPSAFK
VQLQLPDNEVAQISDYYPRNSIDTKEYMSTLTYGFNGNVTGDDTGKIGGL
IGANVSIGHTLKYVQPDFKTILESPTDKKVGWKVIFNNMVNQNWGPYAAA
SWNPVYGNQLFMKTRNGSMKAADNFLDPNKASSLLSSGFSPDFATVITMD
RKASKQQTNIDVIYERVRDDYQLHWTSTNWKGTNTKDKWIDRSSERYKID
WEKEEMTNVDKLAAALEHHHHEIH.

34. A composition comprising a fusion protein of any of claims 15-33.
35. A mutant alpha-hemolysin (mHla) protein, comprising a mutation at amino acid residue 205, 213 or 209-211 of wild-type *S. aureus* alpha-hemolysin, wherein the mutant alpha-hemolysin has lower hemolytic activity than an equivalent titer of wild-type alpha-hemolysin (Hla).

36. The mutant alpha-hemolysin of paragraph 35, wherein the hemolytic activity of mutant alpha-hemolysin is at least 25% lower than an equivalent titer of wild-type Hla.

37. The mutant alpha-hemolysin of paragraph 35 or 36, wherein the mutant alpha-hemolysin comprises one of the following mutations in the wild-type *S. aureus* alphs-hemolysin: (i) residue 205 W to A; (ii) residue 213 W to A; or (iii) residues 209-211 DRD to AAA.

38. The mutant alpha-hemolysin any of claims 13-15, wherein the mutant alpha-hemolysin comprises an amino acid sequence selected from the group consisting of:

(i) W205A (SEQ ID NO: 23)

ADSDINIKTGTTDIGSNTTVKTGDLVTYDKENGMHKKVFYSFIDDKNHN
KKLLVIRTKGTIAGQYRVYSEEGANKSGLAWPSAFKVQLQLPDNEVAQI
SDYYPRNSIDTKEYMSTLTYGFNGNVTGDDTGKIGGLIGANVSIGHTLK
YVQPDFKTILESPTDKKVGWKVIFNNMVNQNAGPYDRDSWNPVYGNQLF
MKTRNGSMKAADNFLDPNKASSLLSSGFSPDFATVITMDRKASKQQTNI
DVIYERVRDDYQLHWTSTNWKGTNTKDKWIDRSSERYKIDWEKEEMTN;

(ii) W213A (SEQ ID NO: 24)

ADSDINIKTGTTDIGSNTTVKTGDLVTYDKENGMHKKVFYSFIDDKNHN
KKLLVIRTKGTIAGQYRVYSEEGANKSGLAWPSAFKVQLQLPDNEVAQI
SDYYPRNSIDTKEYMSTLTYGFNGNVTGDDTGKIGGLIGANVSIGHTLK
YVQPDFKTILESPTDKKVGWKVIFNNMVNQNWGPYDRDSANPVYGNQLF
MKTRNGSMKAADNFLDPNKASSLLSSGFSPDFATVITMDRKASKQQTNI
DVIYERVRDDYQLHWTSTNWKGTNTKDKWIDRSSERYKIDWEKEEMTN;

(iii) DRD209-211AAA (SEQ ID NO: 25)

ADSDINIKTGTTDIGSNTTVKTGDLVTYDKENGMHKKVFYSFIDDKNHN
KKLLVIRTKGTIAGQYRVYSEEGANKSGLAWPSAFKVQLQLPDNEVAQI
SDYYPRNSIDTKEYMSTLTYGFNGNVTGDDTGKIGGLIGANVSIGHTLK
YVQPDFKTILESPTDKKVGWKVIFNNMVNQNWGPYAAASWNPVYGNQLF
MKTRNGSMKAADNFLDPNKASSLLSSGFSPDFATVITMDRKASKQQTNI
DVIYERVRDDYQLHWTSTNWKGTNTKDKWIDRSSERYKIDWEKEEMTN;

and functional variants, portions, and derivatives thereof.

39. A composition comprising a mutant alpha-hemolysin of any of claims 35-38.

40. A fusion protein comprising an alpha-hemolysin and a biotin-binding domain, wherein the fusion protein has lower hemolytic activity than an equivalent titer of wild-type alpha-hemolysin (Hla).

41. The fusion protein of paragraph 18, wherein the alpha-hemolysin is a mutant hemolysin of any of claims 35-38 or the alpha-hemolysin consists of the the amino acids sequence of amino acids 27-319 of wild-type alpha-hemolysin of *S. aureus.*

42. The fusion protein of paragraph 19, wherein the biotin-binding domain consists of the amino acid sequence SEQ ID NO: 1.

43. The fusion protein of any of claims 40-42, wherein the biotin binding domain and the mutant alpha-hemolysin are linked by a peptide linker.

44. The fusion protein of paragraph 43, wherein the peptide linker comprises the amino acid sequence

```
                                            (SEQ ID NO: 22)
GGGGSSS.
```

45. The fusion protein of any of claims 40-44, wherein the fusion protein comprises a bacterial signal sequence at the N-terminus.
46. The fusion protein of paragraph 45, wherein the bacterial signal sequence is

```
                                            (SEQ ID No: 2)
MKKIWLALAGLVLAFSASA.
```

47. The fusion protein of any of paragraph 45 or 46, wherein the signal sequence is linked to the biotin-protein by a peptide linker.
48. The fusion protein of paragraph 47, wherein the peptide linker comprises the amino acid sequence

```
                                            (SEQ ID NO: 8)
AQDP
or
                                            (SEQ ID NO: 9)
VSDP.
```

49. The fusion protein of any of claims 40-48, wherein the fusion protein comprises a purification tag at the C-terminus.
50. The fusion protein of paragraph 49, wherein the purification tag is selected from the group consisting of a histidine tag, a c-my tag, a Halo tag, a Flag tag, and any combinations thereof.
51. The fusion protein of paragraph 50, wherein the histidine tag comprises the amino acid sequence

```
                                            (SEQ ID NO: 10)
HHHHHH.
```

52. The fusion protein of any of claims 49-51, wherein the purification tag is linked to the biotin-binding protein via a peptide linker.
53. The fusion protein of paragraph 52, where the peptide linker comprises the amino acid sequence

```
                                            (SEQ ID NO: 11)
VDKLAAALE.
```

54. The fusion protein of any of claims 40-53, wherein the biotin-binding domain is a biotin-binding protein of any of claims 1-13.
55. The fusion protein of any of claims 40-54, wherein the fusion protein comprises the amino acid sequence selected from the group consisting of SEQ ID NO: 26, SEQ ID NO: 27, and SEQ ID NO: 28.
56. The fusion protein of any of claims 40-55, wherein the hemolytic activity of the fusion protein is at least 25% lower than an equivalent titer of wild-type Hla.
57. A composition comprising a fusion protein of any of claims 40-56.
58. A method inducing an immune response in a subject, comprising administering to the subject a composition of paragraph 14, 34, 39, or 57.
59. A method of vaccinating a mammal against at least one antigen-bearing pathogen, the method comprising administering a composition of paragraph 14, 34, 39, or 57.
60. The method of any of claim 58 or 59, wherein the subject is a human.
61. The method of any of claim 58 or 59, wherein the subject is an agricultural or non-domestic animal.
62. The method of any of claim 58 or 59, wherein the subject is a domestic animal.
63. The method of any of claim 58 or 59, wherein administration is via subcutaneous, intranasal, intradermal or intra muscular injection.
64. The method of paragraph 58, wherein the immune response is an antibody/B-cell response.
65. The method of paragraph 58, wherein the immune response is a CD4+ T-cell response, including Th1, Th2, or Th17 response.
66. The method of paragraph 58, wherein the immune response is a CD8+ T-cell response.
67. The composition of any of claim 14, 34, 39, or 57 for use in a diagnostic for exposure to a pathogen or immune threat.
68. A lipidated biotin-binding protein, comprising an amino acid sequence

```
                                            (SEQ ID NO: 1)
FDASNFKDFSSIASASSSWQNQSGSTMIIQVDSFGNVSGQYVNRAQGTG

CQNSPYPLTGRVNGTFIAFSVGWNNSTENCNSATGWTGYAQVNGNNTEI

VTSWNLAYEGGSGPAIEQGQDTFQYVPTTENKSLLKD
``` and any functional derivatives thereof.

69. The lipidated biotin-binding of paragraph 68, wherein the biotin-binding protein is produced in soluble form at a level of at least 10 mg/L of culture media in *E. coli*.
70. The lipidated biotin binding protein of any of claims 68-69, wherein the biotin-binding protein is a dimer.
71. The lipidated biotin-binding protein of any of claims 68-70, wherein the biotin-binding protein comprises a lipidation sequence at the N-terminus.
72. The lipidated biotin-binding protein of paragraph 71, wherein the lipidation sequence is

```
                                            (SEQ ID No: 3)
MKKVAAFVALSLLMAGC
```

73. The lipidated biotin-binding protein of any of paragraph 71 or 72, wherein the lipidation sequence is linked to the biotin-protein by a peptide linker.
74. The lipidated biotin-binding protein of paragraph 73, wherein the peptide linker comprises the amino acid sequence AQDP (SEQ ID NO: 8) or VSDP (SEQ ID NO: 9).
75. The lipidated biotin-binding protein of any of claims 68-74, wherein the biotin-binding protein comprises a purification tag at the C-terminus.
76. The lipidated biotin-binding protein of paragraph 75, wherein the purification tag is selected from the group consisting of a histidine tag, a c-my tag, a Halo tag, a Flag tag, and any combinations thereof.
77. The lipidated biotin-binding protein of paragraph 76, wherein the histidine tag comprises the amino acid sequence 78. The lipidated biotin-binding protein of any of claims 75-77, wherein the purification tag is linked to the biotin-binding protein via a peptide linker.
79. The lipidated biotin-binding protein of paragraph 78, where the peptide linker comprises the amino acid sequence VDKLAAALE (SEQ ID NO: 11) or GGGGSSSVDKLAAALE (SEQ ID NO: 12).
80. The lipidated biotin-binding protein of any of paragraph 68-79, wherein the biotin-binding protein comprises the amino acid sequence

```
                                         (SEQ ID NO: 20)
MKKVAAFVALSLLMAGCVSDPFDASNFKDFSSIASASSSWQNQSGSTMII

QVDSFGNVSGQYVNRAQGTGCQNSPYPLTGRVNGTFIAFSVGWNNSTENC

NSATGWTGYAQVNGNNTEIVTSWNLAYEGGSGPAIEQGQDTFQYVPTTEN

KSLLKD.
```

81. A composition comprising a lipidated biotin-binding protein of any of claims 68-80.
82. A fusion protein comprising a lipidated biotin-binding protein and a protein or a peptide.
83. The fusion protein of paragraph 82, wherein the protein or peptide is fused to the lipidated biotin-binding protein by a peptide linker.
84. The fusion protein of paragraph 83, wherein the peptide linker comprises the amino acid sequence

```
                                         (SEQ ID NO: 22)
GGGGSSS.
```

85. The fusion protein of any of claims 82-84, wherein the protein or peptide is an antigen selected from the group consisting of: pneumococcal antigens, tuberculosis antigens, anthrax antigens, HIV antigens, seasonal or epidemic flu antigens, *influenzae* antigens, Pertussis antigens, *Staphylococcus aureus* antigens, Meningococcal antigens, *Haemophilus* antigens, HPV antigens, or combinations thereof.
86. The fusion protein of any of paragraph 85, wherein the antigen is a non-hemolytic variant of *S. aureus* alpha-hemolysin.
87. The fusion of paragraph 86, wherein the non-hemolytic variant of *S. aureus* alpha-hemolysin comprises a mutation at amino acid residue 205, 213 or 209-211 of wild-type *S. aureus* alpha-hemolysin.
88. The fusion protein of paragraph 86, wherein the non-hemolytic variant of *S. aureus* alpha-hemolysin comprises one of the following mutations in the wild-type *S. aureus* alpha-hemolysin: (i) residue 205 W to A; (ii) residue 213 W to A; or (iii) residues 209-211 DRD to AAA.
89. The fusion protein of paragraph 86, wherein the non-hemolytic variant of *S. aureus* alpha-hemolysin comprises the amino acid sequence selected from the group consisting of:

(iv) W205A

```
                                         (SEQ ID NO: 23)
ADSDINIKTGTTDIGSNTTVKTGDLVTYDKENGMHKKVFYSFIDDKNHN

KKLLVIRTKGTIAGQYRVYSEEGANKSGLAWPSAFKVQLQLPDNEVAQI

SDYYPRNSIDTKEYMSTLTYGFNGNVTGDDTGKIGGLIGANVSIGHTLK

YVQPDFKTILESPTDKKVGWKVIFNNMVNQNAGPYDRDSWNPVYGNQLF

MKTRNGSMKAADNFLDPNKASSLLSSGFSPDFATVITMDRKASKQQTNI

DVIYERVRDDYQLHWTSTNWKGTNTKDKWIDRSSERYKIDWEKEEMTN;
```

(v) W213A

```
                                         (SEQ ID NO: 24)
ADSDINIKTGTTDIGSNTTVKTGDLVTYDKENGMHKKVFYSFIDDKNHN

KKLLVIRTKGTIAGQYRVYSEEGANKSGLAWPSAFKVQLQLPDNEVAQI

SDYYPRNSIDTKEYMSTLTYGFNGNVTGDDTGKIGGLIGANVSIGHTLK

YVQPDFKTILESPTDKKVGWKVIFNNMVNQNWGPYDRDSANPVYGNQLF

MKTRNGSMKAADNFLDPNKASSLLSSGFSPDFATVITMDRKASKQQTNI

DVIYERVRDDYQLHWTSTNWKGTNTKDKWIDRSSERYKIDWEKEEMTN;
```

(vi) DRD209-211AAA

```
                                         (SEQ ID NO: 25)
ADSDINIKTGTTDIGSNTTVKTGDLVTYDKENGMHKKVFYSFIDDKNHN

KKLLVIRTKGTIAGQYRVYSEEGANKSGLAWPSAFKVQLQLPDNEVAQI

SDYYPRNSIDTKEYMSTLTYGFNGNVTGDDTGKIGGLIGANVSIGHTLK

YVQPDFKTILESPTDKKVGWKVIFNNMVNQNWGPYAAASWNPVYGNQLF

MKTRNGSMKAADNFLDPNKASSLLSSGFSPDFATVITMDRKASKQQTNI

DVIYERVRDDYQLHWTSTNWKGTNTKDKWIDRSSERYKIDWEKEEMTN;
``` and
functional variants, portions, and derivatives thereof.
90. The fusion protein of any of claims 82-89, wherein the fusion protein comprises a lipidation sequence at the N-terminus.
91. The fusion protein of paragraph 90, wherein the lipidation sequence is MKKVAAFVALSLLMAGC (SEQ ID No: 3).
92. The fusion protein of any of paragraph 90 or 91, wherein the signal sequence is linked to the biotin-protein by a peptide linker.
93. The fusion protein of paragraph 92, wherein the peptide linker comprises the amino acid sequence AQDP (SEQ ID NO: 8) or VSDP (SEQ ID NO: 9).
94. The fusion protein of any of claims 82-93, wherein the fusion protein comprises a purification tag at the C-terminus.
95. The fusion protein of paragraph 94, wherein the purification tag is selected from the group consisting of a histidine tag, a c-my tag, a Halo tag, a Flag tag, and any combinations thereof.
96. The fusion protein of paragraph 95, wherein the histidine tag comprises the amino acid sequence HHHHHH (SEQ ID NO: 10).
97. The fusion protein of any of claims 93-96, wherein the purification tag is linked to the biotin-binding protein via a peptide linker.
98. The fusion protein of paragraph 97, where the peptide linker comprises the amino acid sequence

```
                                         (SEQ ID NO: 11)
VDKLAAALE.
```

99. The fusion protein of any of claims 82-98, wherein the lipidated biotin-binding protein is a biotin-binding protein of any of claims 68-80.

100. The fusion protein of any of claims 82-99, wherein the fusion protein comprises the amino acid sequence selected from the group consisting of (i)
SEQ ID NO: 53
MKKVAAFVALSLLMAGCVSPDFDASNFKDFSSIASASSSWQNQSGSTMI
IQVDSFGNVSGQYVNRAQGTGCQNSPYPLTGRVNGTFIAFSVGWNNSTE
NCNSATGWTGYAQVNGNNTEIVTSWNLAYEGGSGPAIEQGQDTFQYVPT
TENKSLLKDGGGGSSSADSDINIKTGTTDIGSNTTVKTGDLVTYDKENG
MHKKVFYSFIDDKNHNKKLLVIRTKGTIAGQYRVYSEEGANKSGLAWPS
AFKVQLQLPDNEVAQISDYYPRNSIDTKEYMSTLTYGFNGNVTGDDTGK
IGGLIGANVSIGHTLKYVQPDFKTILESPTDKKVGWKVIFNNMVNQNAG
PYDRDSWNPVYGNQLFMKTRNGSMKAADNFLDPNKASSLLSSGFSPDFA
TVITMDRKASKQQTNIDVIYERVRDDYQLHWTSTNWKGTNTKDKWIDRS
SERYKIDWEKEEMTNVDKLAAALEHHHHHH;

(ii)
SEQ ID NO: 54
MKKVAAFVALSLLMAGCVSPDFDASNFKDFSSIASASSSWQNQSGSTMI
IQVDSFGNVSGQYVNRAQGTGCQNSPYPLTGRVNGTFIAFSVGWNNSTE
NCNSATGWTGYAQVNGNNTEIVTSWNLAYEGGSGPAIEQGQDTFQYVPT
TENKSLLKDGGGGSSSADSDINIKTGTTDIGSNTTVKTGDLVTYDKENG
MHKKVFYSFIDDKNHNKKLLVIRTKGTIAGQYRVYSEEGANKSGLAWPS
AFKVQLQLPDNEVAQISDYYPRNSIDTKEYMSTLTYGFNGNVTGDDTGK
IGGLIGANVSIGHTLKYVQPDFKTILESPTDKKVGWKVIFNNMVNQNWG
PYDRDSANPVYGNQLFMKTRNGSMKAADNFLDPNKASSLLSSGFSPDFA
TVITMDRKASKQQTNIDVIYERVRDDYQLHWTSTNWKGTNTKDKWIDRS
SERYKIDWEKEEMTNVDKLAAALEHHHHHH;
and (iii)
SEQ ID NO: 55
MKKVAAFVALSLLMAGCVSPDFDASNFKDFSSIASASSSWQNQSGSTMI
IQVDSFGNVSGQYVNRAQGTGCQNSPYPLTGRVNGTFIAFSVGWNNSTE
NCNSATGWTGYAQVNGNNTEIVTSWNLAYEGGSGPAIEQGQDTFQYVPT
TENKSLLKDGGGGSSSADSDINIKTGTTDIGSNTTVKTGDLVTYDKENG
MHKKVFYSFIDDKNHNKKLLVIRTKGTIAGQYRVYSEEGANKSGLAWPS
AFKVQLQLPDNEVAQISDYYPRNSIDTKEYMSTLTYGFNGNVTGDDTGK
IGGLIGANVSIGHTLKYVQPDFKTILESPTDKKVGWKVIFNNMVNQNWG
PYAAASWNPVYGNQLFMKTRNGSMKAADNFLDPNKASSLLSSGFSPDFA
TVITMDRKASKQQTNIDVIYERVRDDYQLHWTSTNWKGTNTKDKWIDRS
SERYKIDWEKEEMTNVDKLAAALEHHHHHH (SEQ ID NO: 55).

101. A composition comprising a lipidated biotin-binding protein of any of claims 82-100.
102. A method inducing an immune response in a subject, comprising administering to the subject a composition of paragraph 81 or 101.
103. A method of vaccinating a mammal against at least one antigen-bearing pathogen, the method comprising administering a composition of paragraph 81 or 101.
104. The method of any of claim 102 or 103, wherein the subject is a human.
105. The method of any of claim 102 or 103, wherein the subject is an agricultural or non-domestic animal.
106. The method of any of claim 102 or 103, wherein the subject is a domestic animal.
107. The method of any of claim 102 or 103, wherein administration is via subcutaneous, intranasal, intradermal or intra muscular injection.
108. The method of paragraph 102, wherein the immune response is an antibody/B-cell response.
109. The method of paragraph 102, wherein the immune response is a CD4+ T-cell response, including Th1, Th2, or Th17 response.
110. The method of paragraph 102, wherein the immune response is a CD8+ T-cell response.
111. The composition of any of claim 81 or 101 for use in a diagnostic for exposure to a pathogen or immune threat.

Some Selected Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

As used herein and in the claims, the singular forms include the plural reference and vice versa unless the context clearly indicates otherwise. The term "or" is inclusive unless modified, for example, by "either." Other than in the operating examples, or where otherwise cindicated, all numbers expressing quantities of ingredients or reaction conditions used herein should be understood as modified in all instances by the term "about."

The term "immunogenic composition" used herein is defined as a composition capable of eliciting an immune response, such as an antibody or cellular immune response, when administered to a subject. The immunogenic compositions of the present invention may or may not be immunoprotective or therapeutic. When the immunogenic compositions of the present invention prevent, ameliorate, palliate or eliminate disease from the subject, then the immunogenic composition may optionally be referred to as a vaccine. As used herein, however, the term immunogenic composition is not intended to be limited to vaccines.

As used herein, the term "antigen" refers to any substance that prompts an immune response directed against the substance. In some embodiments, an antigen is a peptide or a polypeptide, and in other embodiments, it can be any chemical or moiety, e.g., a carbohydrate, that elicits an immune response directed against the substance.

The term "associates" as used herein refers to the linkage of two or more molecules by non-covalent or covalent bonds. In some embodiments, where linking of two or more molecules occurs by a covalent bond, the two or more molecules can be fused together, or cross-linked together. In some embodiments, where linking of two or more molecules occurs by a non-covalent bond, the two or more molecules can form a complex.

The term "complex" as used herein refers to a collection of two or more molecules, connected spatially by means other than a covalent interaction; for example they can be connected by electrostatic interactions, hydrogen bound or by hydrophobic interactions (i.e., van der Waals forces).

As used herein, the term "fused" means that at least one protein or peptide is physically associated with a second protein or peptide. In some embodiments, fusion is typically a covalent linkage, however, other types of linkages are encompassed in the term "fused" include, for example, linkage via an electrostatic interaction, or a hydrophobic interaction and the like. Covalent linkage can encompass linkage as a fusion protein or chemically coupled linkage, for example via a disulfide bound formed between two cysteine residues.

As used herein, the term "fusion polypeptide" or "fusion protein" means a protein created by joining two or more polypeptide sequences together. The fusion polypeptides encompassed in this invention include translation products of a chimeric gene construct that joins the DNA sequences encoding one or more antigens, or fragments or mutants thereof, with the DNA sequence encoding a second polypeptide to form a single open-reading frame. In other words, a "fusion polypeptide" or "fusion protein" is a recombinant protein of two or more proteins which are joined by a peptide bond. In some embodiments, the second protein to which the antigens are fused to is a complementary affinity molecule which is capable of interacting with a first affinity molecule of the complementary affinity pair.

The terms "polypeptide" and "protein" can be used interchangeably to refer to a polymer of amino acid residues linked by peptide bonds, and for the purposes of the claimed invention, have a typical minimum length of at least 25 amino acids. The term "polypeptide" and "protein" can encompass a multimeric protein, e.g., a protein containing more than one domain or subunit. The term "peptide" as used herein refers to a sequence of peptide bond-linked amino acids containing less than 25 amino acids, e.g., between about 4 amino acids and 25 amino acids in length. Proteins and peptides can be composed of linearly arranged amino acids linked by peptide bonds, whether produced biologically, recombinantly, or synthetically and whether composed of naturally occurring or non-naturally occurring amino acids, are included within this definition. Both full-length proteins and fragments thereof greater than 25 amino acids are encompassed by the definition of protein. The terms also include polypeptides that have co-translational (e.g., signal peptide cleavage) and post-translational modifications of the polypeptide, such as, for example, disulfide-bond formation, glycosylation, acetylation, phosphorylation, lipidation, proteolytic cleavage (e.g., cleavage by metalloproteases), and the like. Furthermore, as used herein, a "polypeptide" refers to a protein that includes modifications, such as deletions, additions, and substitutions (generally conservative in nature as would be known to a person in the art) to the native sequence, as long as the protein maintains the desired activity. These modifications can be deliberate, as through site-directed mutagenesis, or can be accidental, such as through mutations of hosts that produce the proteins, or errors due to PCR amplification or other recombinant DNA methods.

By "signal sequence" is meant a nucleic acid sequence which, when operably linked to a nucleic acid molecule, facilitates secretion of the product (e.g., protein or peptide) encoded by the nucleic acid molecule. In some embodiments, the signal sequence is preferably located 5' to the nucleic acid molecule.

As used herein, the term "N-glycosylated" or "N-glycosylation" refers to the covalent attachment of a sugar moiety to asparagine residues in a polypeptide. Sugar moieties can include but are not limited to glucose, mannose, and N-acetylglucosamine. Modifications of the glycans are also included, e.g., siaylation.

An "antigen presenting cell" or "APC" is a cell that expresses the Major Histocompatibility complex (MHC) molecules and can display foreign antigen complexed with MHC on its surface. Examples of antigen presenting cells are dendritic cells, macrophages, B-cells, fibroblasts (skin), thymic epithelial cells, thyroid epithelial cells, glial cells (brain), pancreatic beta cells, and vascular endothelial cells.

The term "functional portion" or "functional fragment" as used in the context of a "functional portion of an antigen" refers to a portion of the antigen or antigen polypeptide that mediates the same effect as the full antigen moiety, e.g., elicits an immune response in a subject, or mediates an association with other molecule, e.g., comprises at least on epitope.

A "portion" of a target antigen as that term is used herein will be at least 3 amino acids in length, and can be, for example, at least 6, at least 8, at least 10, at least 14, at least 16, at least 17, at least 18, at least 19, at least 20 or at least 25 amino acids or greater, inclusive.

The terms "Cytotoxic T Lymphocyte" or "CTL" refers to lymphocytes which induce apoptosis in targeted cells. CTLs form antigen-specific conjugates with target cells via interaction of TCRs with processed antigen (Ag) on target cell surfaces, resulting in apoptosis of the targeted cell. Apoptotic bodies are eliminated by macrophages. The term "CTL response" is used to refer to the primary immune response mediated by CTL cells.

The term "cell mediated immunity" or "CMI" as used herein refers to an immune response that does not involve antibodies or complement but rather involves the activation of, for example, macrophages, natural killer cells (NK), antigen-specific cytotoxic T-lymphocytes (T-cells), and the release of various cytokines in response to a target antigen. Stated another way, CMI refers to immune cells (such as T cells and other lymphocytes) which bind to the surface of other cells that display a target antigen (such as antigen presenting cells (APS)) and trigger a response. The response may involve either other lymphocytes and/or any of the other white blood cells (leukocytes) and the release of cytokines. Cellular immunity protects the body by: (i) activating antigen-specific cytotoxic T-lymphocytes (CTLs) that are able to destroy body cells displaying epitopes of foreign antigen on their surface, such as virus-infected cells and cells with intracellular bacteria; (2) activating macrophages and NK cells, enabling them to destroy intracellular pathogens; and (3) stimulating cells to secrete a variety of cytokines that influence the function of other cells involved in adaptive immune responses and innate immune responses.

The term "immune cell" as used herein refers to any cell which can release a cytokine in response to a direct or indirect antigenic stimulation. Included in the term "immune cells" herein are lympocytes, including natural killer (NK) cells, T-cells (CD4+ and/or CD8+ cells), B-cells, macrophages and monocytes, Th cells; Th1 cells; Th2 cells; leukocytes; dendritic cells; macrophages; mast cells and monocytes and any other cell which is capable of producing a cytokine molecule in response to direct or indirect antigen stimulation. Typically, an immune cell is a lymphocyte, for example a T-cell lymphocyte.

The term "cytokine" as used herein refers to a molecule released from an immune cell in response to stimulation with an antigen. Examples of such cytokines include, but are not limited to: GM-CSF; IL-1α; IL-1β; IL-2; IL-3; IL-4; IL-5; IL-6; IL-7; IL-8; IL-10; IL-12; IL-17A, IL-17F or other members of the IL-17 family, IL-22, IL-23, IFN-α;

IFN-β; IFN-γ; MIP-1α; MIP-1β; TGF-β; TNFα, or TNFβ. The term "cytokine" does not include antibodies The term "subject" as used herein refers to any animal in which it is useful to elicit an immune response. The subject can be a wild, domestic, commercial or companion animal such as a bird or mammal. The subject can be a human. Although in one embodiment of the invention it is contemplated that the immunogenic compositions as disclosed herein can also be suitable for the therapeutic or preventative treatment in humans, it is also applicable to warm-blooded vertebrates, e.g., mammals, such as non-human primates, (particularly higher primates), sheep, dog, rodent (e.g., mouse or rat), guinea pig, goat, pig, cat, rabbits, cows, and non-mammals such as chickens, ducks, or turkeys. In another embodiment, the subject is a wild animal, for example a bird such as for the diagnosis of avian flu. In some embodiments, the subject is an experimental animal or animal substitute as a disease model. The subject may be a subject in need of veterinary treatment, where eliciting an immune response to an antigen is useful to prevent a disease and/or to control the spread of a disease, for example SIV, STL1, SFV, or in the case of live-stock, hoof and mouth disease, or in the case of birds Marek's disease or avian influenza, and other such diseases.

As used herein, the term "pathogen" refers to an organism or molecule that causes a disease or disorder in a subject. For example, pathogens include but are not limited to viruses, fungi, bacteria, parasites, and other infectious organisms or molecules therefrom, as well as taxonomically related macroscopic organisms within the categories algae, fungi, yeast, protozoa, or the like.

A "cancer cell" refers to a cancerous, pre-cancerous, or transformed cell, either in vivo, ex vivo, or in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene.

Transformation/cancer is associated with, e.g., morphological changes, immortalization of cells, aberrant growth control, foci formation, anchorage independence, malignancy, loss of contact inhibition and density limitation of growth, growth factor or serum independence, tumor specific markers, invasiveness or metastasis, and tumor growth in suitable animal hosts such as nude mice. See, e.g., Freshney, CULTURE ANIMAL CELLS: MANUAL BASIC TECH. (3rd ed., 1994).

The term "wild type" refers to the naturally-occurring, normal polynucleotide sequence encoding a protein, or a portion thereof, or protein sequence, or portion thereof, respectively, as it normally exists in vivo.

The term "mutant" refers to an organism or cell with any change in its genetic material, in particular a change (i.e., deletion, substitution, addition, or alteration) relative to a wild-type polynucleotide sequence or any change relative to a wild-type protein sequence. The term "variant" may be used interchangeably with "mutant". Although it is often assumed that a change in the genetic material results in a change of the function of the protein, the terms "mutant" and "variant" refer to a change in the sequence of a wild-type protein regardless of whether that change alters the function of the protein (e.g., increases, decreases, imparts a new function), or whether that change has no effect on the function of the protein (e.g., the mutation or variation is silent).

The term "pharmaceutically acceptable" refers to compounds and compositions which may be administered to mammals without undue toxicity. The term "pharmaceutically acceptable carriers" excludes tissue culture medium. Exemplary pharmaceutically acceptable salts include but are not limited to mineral acid salts such as hydrochlorides, hydrobromides, phosphates, sulfates, and the like, and the salts of organic acids such as acetates, propionates, malonates, benzoates, and the like. Pharmaceutically acceptable carriers are well-known in the art.

It will be appreciated that proteins or polypeptides often contain amino acids other than the 20 amino acids commonly referred to as the 20 naturally occurring amino acids, and that many amino acids, including the terminal amino acids, can be modified in a given polypeptide, either by natural processes such as glycosylation and other post-translational modifications, or by chemical modification techniques which are well known in the art. Known modifications which can be present in polypeptides of the present invention include, but are not limited to, acetylation, acylation, ADP-ribosylation, amidation, covalent attachment of flavin, covalent attachment of a heme moiety, covalent attachment of a polynucleotide or polynucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formulation, gamma-carboxylation, glycation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

As used herein, the terms "homologous" or "homologues" are used interchangeably, and when used to describe a polynucleotide or polypeptide, indicate that two polynucleotides or polypeptides, or designated sequences thereof, when optimally aligned and compared, for example using BLAST, version 2. 2. 14 with default parameters for an alignment are identical, with appropriate nucleotide insertions or deletions or amino-acid insertions or deletions, in at least 70% of the nucleotides, usually from about 75% to 99%, such as at least about 98 to 99% of the nucleotides. For a polypeptide, there should be at least 50% of amino acid identity in the polypeptide. The term "homolog" or "homologous" as used herein also refers to homology with respect to structure. Determination of homologs of genes or polypeptides can be easily ascertained by the skilled artisan. When in the context with a defined percentage, the defined percentage homology means at least that percentage of amino acid similarity. For example, 85% homology refers to at least 85% of amino acid similarity.

As used herein, the term "heterologous" reference to nucleic acid sequences, proteins or polypeptides mean that these molecules are not naturally occurring in that cell. For example, the nucleic acid sequence coding for a fusion antigen polypeptide described herein that is inserted into a cell, e.g. in the context of a protein expression vector, is a heterologous nucleic acid sequence.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Where necessary or desired, optimal alignment of sequences for comparison can be conducted by any variety of approaches, as these are well-known in the art.

The term "variant" as used herein may refer to a polypeptide or nucleic acid that differs from the naturally occurring polypeptide or nucleic acid by one or more amino acid or nucleic acid deletions, additions, substitutions or side-chain modifications, yet retains one or more specific functions or biological activities of the naturally occurring molecule. Amino acid substitutions include alterations in which an amino acid is replaced with a different naturally-occurring or a non-conventional amino acid residue. Such substitutions may be classified as "conservative," in which case an amino acid residue contained in a polypeptide is replaced with another naturally occurring amino acid of similar character either in relation to polarity, side chain functionality or size. Substitutions encompassed by variants as described herein may also be "non conservative," in which an amino acid residue which is present in a peptide is substituted with an amino acid having different properties (e.g., substituting a charged or hydrophobic amino acid with alanine), or alternatively, in which a naturally-occurring amino acid is substituted with a non-conventional amino acid. Also encompassed within the term "variant," when used with reference to a polynucleotide or polypeptide, are variations in primary, secondary, or tertiary structure, as compared to a reference polynucleotide or polypeptide, respectively (e.g., as compared to a wild-type polynucleotide or polypeptide).

The term "substantially similar," when used in reference to a variant of an antigen or a functional derivative of an antigen as compared to the original antigen means that a particular subject sequence varies from the sequence of the antigen polypeptide by one or more substitutions, deletions, or additions, but retains at least 50%, or higher, e.g., at least 60%, 70%, 80%, 90% or more, inclusive, of the function of the antigen to elicit an immune response in a subject. In determining polynucleotide sequences, all subject polynucleotide sequences capable of encoding substantially similar amino acid sequences are considered to be substantially similar to a reference polynucleotide sequence, regardless of differences in codon sequence. A nucleotide sequence is "substantially similar" to a given antigen nucleic acid sequence if: (a) the nucleotide sequence hybridizes to the coding regions of the native antigen sequence, or (b) the nucleotide sequence is capable of hybridization to nucleotide sequence of the native antigen under moderately stringent conditions and has biological activity similar to the native antigen protein; or (c) the nucleotide sequences are degenerate as a result of the genetic code relative to the nucleotide sequences defined in (a) or (b). Substantially similar proteins will typically be greater than about 80% similar to the corresponding sequence of the native protein.

Variants can include conservative or non-conservative amino acid changes, as described below. Polynucleotide changes can result in amino acid substitutions, additions, deletions, fusions and truncations in the polypeptide encoded by the reference sequence. Variants can also include insertions, deletions or substitutions of amino acids, including insertions and substitutions of amino acids and other molecules) that do not normally occur in the peptide sequence that is the basis of the variant, for example but not limited to insertion of ornithine which do not normally occur in human proteins. "Conservative amino acid substitutions" result from replacing one amino acid with another having similar structural and/or chemical properties. Conservative substitution tables providing functionally similar amino acids are well known in the art. For example, the following six groups each contain amino acids that are conservative substitutions for one another: (1) Alanine (A), Serine (S), Threonine (T); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); and (6) Phenylalanine (F), Tyrosine (Y), Tryptophan (W). See, e.g., Creighton, PROTEINS (W. H. Freeman & Co., 1984).

The choice of conservative amino acids may be selected based on the location of the amino acid to be substituted in the peptide, for example if the amino acid is on the exterior of the peptide and exposed to solvents, or on the interior and not exposed to solvents. Selection of such conservative amino acid substitutions is within the skill of one of ordinary skill in the art. Accordingly, one can select conservative amino acid substitutions suitable for amino acids on the exterior of a protein or peptide (i.e. amino acids exposed to a solvent). These substitutions include, but are not limited to the following: substitution of Y with F, T with S or K, P with A, E with D or Q, N with D or G, R with K, G with N or A, T with S or K, D with N or E, I with L or V, F with Y, S with T or A, R with K, G with N or A, K with R, A with S, K or P.

Alternatively, one can also select conservative amino acid substitutions suitable for amino acids on the interior of a protein or peptide (i.e., the amino acids are not exposed to a solvent). For example, one can use the following conservative substitutions: where Y is substituted with F, T with A or S, I with L or V, W with Y, M with L, N with D, G with A, T with A or S, D with N, I with L or V, F with Y or L, S with A or T and A with S, G, T or V. In some embodiments, LF polypeptides including non-conservative amino acid substitutions are also encompassed within the term "variants." As used herein, the term "non-conservative" substitution refers to substituting an amino acid residue for a different amino acid residue that has different chemical properties. Non-limiting examples of non-conservative substitutions include aspartic acid (D) being replaced with glycine (G); asparagine (N) being replaced with lysine (K); and alanine (A) being replaced with arginine (R).

The term "derivative" as used herein refers to peptides which have been chemically modified, for example by ubiquitination, labeling, pegylation (derivatization with polyethylene glycol) or addition of other molecules. A molecule is also a "derivative" of another molecule when it contains additional chemical moieties not normally a part of the molecule. Such moieties can improve the molecule's solubility, absorption, biological half-life, etc. The moieties can alternatively decrease the toxicity of the molecule, or eliminate or attenuate an undesirable side effect of the molecule, etc. Moieties capable of mediating such effects are disclosed in REMINGTON'S PHARMACEUTICAL SCIENCES (21st ed., Tory, ed., Lippincott Williams & Wilkins, Baltimore, Md., 2006).

The term "functional" when used in conjunction with "derivative" or "variant" refers to a protein molecule which possesses a biological activity that is substantially similar to a biological activity of the entity or molecule of which it is a derivative or variant. "Substantially similar" in this context means that the biological activity, e.g., antigenicity of a polypeptide, is at least 50% as active as a reference, e.g., a corresponding wild-type polypeptide, e.g., at least 60% as active, 70% as active, 80% as active, 90% as active, 95% as active, 100% as active or even higher (i.e., the variant or derivative has greater activity than the wild-type), e.g., 110% as active, 120% as active, or more, inclusive.

The term "recombinant" when used to describe a nucleic acid molecule, means a polynucleotide of genomic, cDNA, viral, semisynthetic, and/or synthetic origin, which, by virtue of its origin or manipulation, is not associated with all or a portion of the polynucleotide sequences with which it is associated in nature. The term recombinant as used with respect to a peptide, polypeptide, protein, or recombinant fusion protein, means a polypeptide produced by expression from a recombinant polynucleotide. The term recombinant as used with respect to a host cell means a host cell into which a recombinant polynucleotide has been introduced. Recombinant is also used herein to refer to, with reference to material (e.g., a cell, a nucleic acid, a protein, or a vector) that the material has been modified by the introduction of a heterologous material (e.g., a cell, a nucleic acid, a protein, or a vector).

The term "vectors" refers to a nucleic acid molecule capable of transporting or mediating expression of a heterologous nucleic acid to which it has been linked to a host cell; a plasmid is a species of the genus encompassed by the term "vector." The term "vector" typically refers to a nucleic acid sequence containing an origin of replication and other entities necessary for replication and/or maintenance in a host cell. Vectors capable of directing the expression of genes and/or nucleic acid sequence to which they are operatively linked are referred to herein as "expression vectors". In general, expression vectors of utility are often in the form of "plasmids" which refer to circular double stranded DNA molecules which, in their vector form are not bound to the chromosome, and typically comprise entities for stable or transient expression or the encoded DNA. Other expression vectors that can be used in the methods as disclosed herein include, but are not limited to plasmids, episomes, bacterial artificial chromosomes, yeast artificial chromosomes, bacteriophages or viral vectors, and such vectors can integrate into the host's genome or replicate autonomously in the particular cell. A vector can be a DNA or RNA vector. Other forms of expression vectors known by those skilled in the art which serve the equivalent functions can also be used, for example self replicating extrachromosomal vectors or vectors which integrates into a host genome. Preferred vectors are those capable of autonomous replication and/or expression of nucleic acids to which they are linked.

The term "reduced" or "reduce" or "decrease" as used herein generally means a decrease by a statistically significant amount relative to a reference. For avoidance of doubt, "reduced" means statistically significant decrease of at least 10% as compared to a reference level, for example a decrease by at least 20%, at least 30%, at least 40%, at least t 50%, or least 60%, or least 70%, or least 80%, at least 90% or more, up to and including a 100% decrease (i.e., absent level as compared to a reference sample), or any decrease between 10-100% as compared to a reference level, as that term is defined herein.

The term "low" as used herein generally means lower by a statically significant amount; for the avoidance of doubt, "low" means a statistically significant value at least 10% lower than a reference level, for example a value at least 20% lower than a reference level, at least 30% lower than a reference level, at least 40% lower than a reference level, at least 50% lower than a reference level, at least 60% lower than a reference level, at least 70% lower than a reference level, at least 80% lower than a reference level, at least 90% lower than a reference level, up to and including 100% lower than a reference level (i.e., absent level as compared to a reference sample).

The terms "increased" or "increase" as used herein generally mean an increase by a statically significant amount; such as a statistically significant increase of at least 10% as compared to a reference level, including an increase of at least 20%, at least 30%, at least 40%, at least 50%, at least 60%, at least 70%, at least 80%, at least 90%, at least 100% or more, inclusive, including, for example at least 2-fold, at least 3-fold, at least 4-fold, at least 5-fold, at least 10-fold increase or greater as compared to a reference level, as that term is defined herein.

The term "high" as used herein generally means a higher by a statically significant amount relative to a reference; such as a statistically significant value at least 10% higher than a reference level, for example at least 20% higher, at least 30% higher, at least 40% higher, at least 50% higher, at least 60% higher, at least 70% higher, at least 80% higher, at least 90% higher, at least 100% higher, inclusive, such as at least 2-fold higher, at least 3-fold higher, at least 4-fold higher, at least 5-fold higher, at least 10-fold higher or more, as compared to a reference level.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment of the invention.

It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described herein.

As used herein the term "biotin" refers to the compound biotin itself and analogues, derivatives and variants thereof. Thus, the term "biotin" includes biotin (cis-hexahydro-2-oxo-1H-thieno [3,4]imidazole-4-pentanoic acid) and any derivatives and analogs thereof, including biotin-like compounds. Such compounds include, for example, biotin-e-N-lysine, biocytin hydrazide, amino or sulfhydryl derivatives of 2-iminobiotin and biotinyl-E-aminocaproic acid-N-hydroxysuccinimide ester, sulfosuccinimideiminobiotin, biotinbromoacetylhydrazide, p-diazobenzoyl biocytin, 3-(N-maleimidopropionyl)biocytin, desthiobiotin, and the like. The term "biotin" also comprises biotin variants that can specifically bind to one or more of a Rhizavidin, avidin, streptavidin, tamavidin moiety, or other avidin-like peptides.

Although the foregoing invention has been described in some detail by way of illustration and example for purposes of clarity of understanding it will be readily apparent to one of ordinary skill in the art in light of the teachings of this invention that certain changes and modifications may be made thereto without departing from the spirit or scope of the appended claims. The following is meant to be illustrative of the present invention; however, the practice of the invention is not limited or restricted in any way by the examples.

EXAMPLES

Example 1: Expressing High Yield and Soluble Recombinant Biotin-Binding Protein and Fusion Proteins Thereof in E. coli The recombinant Rhizavidin (rRhavi) used in these studies is an N-terminal modified version that contains only the residues 45 to 179 of the wild type protein. To optimize the expression level of rRhavi in *E. coli*, the gene sequence that encodes Rhizavidin polypeptides (45-179) was re-designed by using *E. coli*-preferred expression codons, then synthesized and cloned into the PET21b vector. To facilitate the correct folding and obtain a high yield of soluble recombinant protein, a DNA sequence encoding an *E. coli* periplasmic localization signal sequence (19 amino acids, MKKIWLALAGLVLAFSASA, SEQ ID NO: 2) was introduced at the 5' end of the synthetic gene of rRhavi. This signal sequence is predicted to be deleted automatically from the recombinant protein after its targeting to the periplasm of *E. coli* during the process of expression.

A DNA sequence encoding a flexible linker region and His-tag (GGGGSSSVDKLAAALEHHHHHH, SEQ ID NO: 14) was directly inserted into the 3' end of the synthetic rRhavi gene. This helps for the purification of recombinant biotin-binding protein. Furthermore, an antigen can be inserted in the linker having a flexible linker on both sides, e.g., the antigen can be inserted between amino acids S and V of the linker. As such the antigen is separated from the biotin-binding protein by the peptide linker (GGGGSSS, SEQ ID NO: 22) and from the His-tag by the peptide linker (VDKLAAALE, SEQ ID NO: 11) this can stabilize the fusion protein.

To construct Rhizavidin-antigen fusion proteins, a DNA sequence encoding a flexible linker region consisting of seven amino acids (GGGGSSS, SEQ ID NO: 22) can be directly inserted into the 3' end of the synthetic rRhavi gene, to help stabilize the fusion protein. The genes encoding candidate antigens (full length or desired fragment) were amplified from the genomic DNA of interested pathogens by routine PCR procedures and inserted into the rRhavi expression vector just beyond the linker region.

For protein expression, the plasmids containing target constructs were transformed into *E. coli* strain BL21 (DE3) using standard heat-shock procedure. A single colony was picked freshly from the plate (or a glycerol stock was used later) and inoculated into 30 ml Luria-Bertani (LB) medium containing Ampicillin (Amp+) for an overnight culture at 37° C. On day 2, a 5 ml starting culture was inoculated into 1 liter of LB medium/Amp+ and grown at 37° C. until $OD_{600}=1$ was reached. After cooling the medium to 16° C., 0.2 mM final concentration of IPTG was added into the cultures for an overnight induction.

Proteins were purified from the periplasmic fraction using a modified osmotic shock protocol. Briefly, the bacterial cells from the 6 liter culture were collected and re-suspended in 120 ml buffer containing 30 mM Tris (pH 8.0), 20% sucrose and 1 mM EDTA. After stirring at room temperature for 20 min, the cells were re-pelleted by centrifugation at 10,000 rpm for 10 min. The supernatant was collected as fraction 1, and the cells were re-suspended in 80 ml ice cold solution containing 5 mM MgCl2, proteinase inhibitor and DNase. After stirring at 4° for 20 min, the mixture was subjected to centrifugation at 13,000 rpm for 20 min and the supernatant was collected as fraction 2. After adding a final concentration of 150 mM NaCl, 10 mM $MgCl_2$ and 10 mM Imidazole, the supernatant combining fraction 1 and fraction 2 was applied onto a Ni-NTA column. The proteins eluted from the Ni-NTA column were further purified by gel-filtration using superdex 200 column running on AKTA purifier. The peak fractions containing target protein were pooled and concentrated. The protein concentration was measured by using BCA protein assay kit from Bio-Rad. Purified proteins were aliquoted, flash-frozen in liquid nitrogen and kept at −80° C. for future use.

The construct of biotin-binding protein is shown schematically in FIG. 1, and SDS-PAGE of the purified biotin-binding protein is shown in FIG. 2.

The construct of fusion proteins comprising biotin-binding protein is shown schematically in FIG. 3, and the exemplary SDS-PAGE of the purified fusion proteins are shown in FIG. 4.

Example 2: Lipidated Derivative of Biotin-Binding Proteins

A lipidated derivate of recombinant biotin-binding protein was produced using a method similar to the one described in Example 1. The lipidated derivate used in this study is an N-terminal modified version of wild type Rhizavidin that contains only the residues 45 to 179 of the wild type protein. To optimize the expression level of rRhavi in *E. coli*, the gene sequence that encodes Rhizavidin polypeptides (45-179) was re-designed by using *E. coli* preferred expression codons, then synthesized and cloned into the PET21b vector. To facilitate the lipidation, correct folding and obtain a high yield of soluble recombinant protein, a DNA sequence encoding lipidation sequence (19 amino acids, MKKVAAFVALSLLMAGC, SEQ ID NO: 3) was introduced at the 5' end of the synthetic gene of rRhavi. The lipidation will be added on the Cys residue of lipidation sequence by bacreria, e.g., *E. coli*, during the process of expression.

For protein expression, the plasmid containing target constructs was transformed into *E. coli* strain BL21 (DE3) using standard heat-shock procedure. A single colony was picked freshly from the plate (or a glycerol stock was used later) and inoculated into 30 ml Luria-Bertani (LB) medium containing Ampicillin (Amp+) for an overnight culture at 37° C. On day 2, a 5 ml starting culture was inoculated into 1 liter of LB medium/Amp+ and grown at 37° C. until $OD_{600}=1$ was reached. After cooling the medium to 16° C., 0.2 mM final concentration of IPTG was added into the cultures for an overnight induction.

Lipidated rhizavidin was purified from *E. coli* membrane fraction. *E coli* cells were collected and resuspended in lysis buffer (20 mM Tris, 500 mM NaCl, pH 8.0) containing protease inhibitors, Dnase, 10 mM $Mg^{2+}$ and lysozyme. Cells were disrupted by one freeze-thaw cycle and the supernatant was removed after centrifugation at 13,000 rpm for 45 min. Cell pellets were then resuspended in lysis buffer containing 0.5% SDOC, and homogenized by beads beater. The lysates were then applied for centrifugation at 13,000 rpm for 45 min, and the supernatant was collected for affinity purification. Lipidated rhavi was eluted with lysis buffer containing 0.5% SDOC and 300 mM Im.

The proteins eluted from the Ni-NTA column were further purified by gel-filtration using superdex 200 column running on AKTA purifier. The peak fractions containing target protein were pooled and concentrated. The protein concentration was measured by using BCA protein assay kit from Bio-Rad. Purified proteins were aliquoted, flash-frozen in liquid nitrogen and kept at −80° C. for future use.

The lipidated biotin-binding protein produced is shown schematically in FIG. 5, and SDS-PAGE of the purified lipidated biotin-binding protein is shown in FIG. 6.

Example 3: TLR2 Activity of Lipidated Biotin-Binding Protein

TLR2 activity of lipidated biotin-binding protein was tested in HEK TLR2 cells. HEK TLR2 cells were plated in 24 well plate at $5\times10^5$ cells/per well in 500 µl volume. Lipidated biotin-binding protein was added at different concentrations for stimulation at 37° C. overnight. The supernatants were collected the second day for IL-8 measurement by ELISA. As a control, HEK 293 cells were used for stimulation at the same condition.

Figure 7:
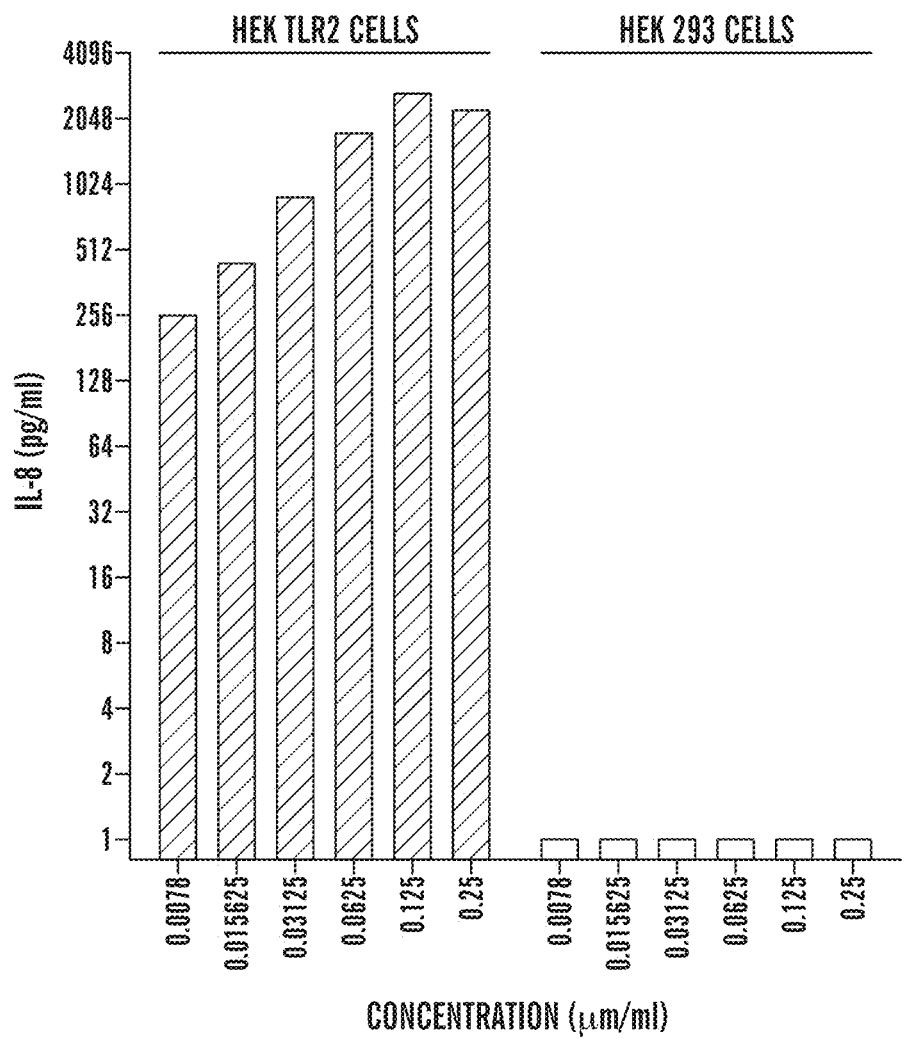
FIG. 7 is a bar graph showing dose-dependent TLR2 activity of the lipidated biotin-binding protein.
Figures 8, 9:
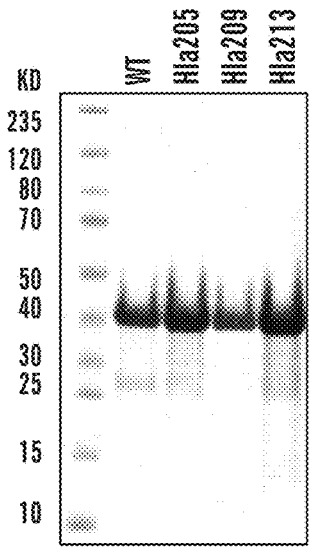
FIG. 8 is a schematic representation of recombinant WT or mutant S. aureus alpha-hemolysin (Hla) and their rhizavidin fusion proteins described herein. In the non-hemolytic Hla, point mutations were made as follow: (i) residue 205 W to A; (ii) residue 213 W to A; or (iii) residues 209-211 from DRD to AAA.
FIG. 9 is a SDS-PAGE of purified wild-type Hla or non-hemolytic variants thereof.
Figure 10:
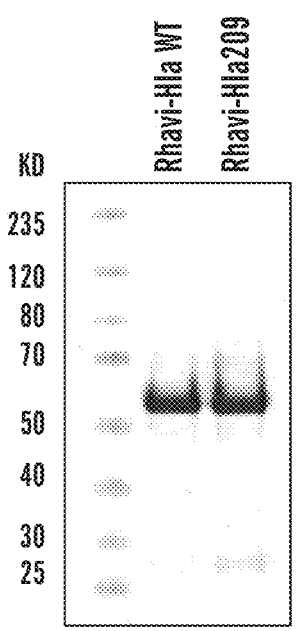
FIG. 10 is SDS-PAGE of purified biotin-binding fusion proteins of wild-type Hla or non-hemolytic variants thereof.
Figure 11:
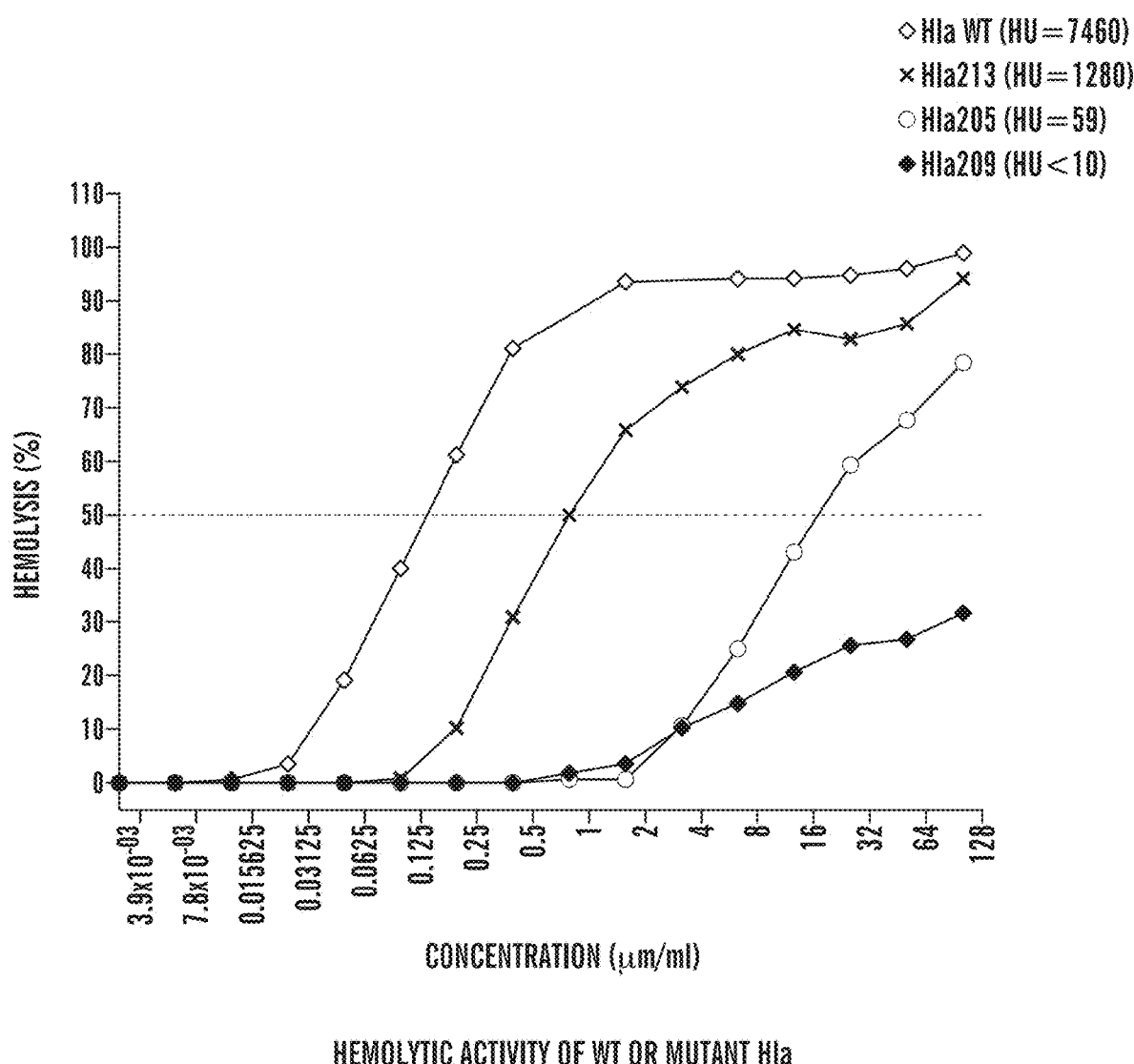
FIG. 11 is a line graph showing hemolytic activity of WT Hla and non-hemolytic variants thereof.
Figure 12:
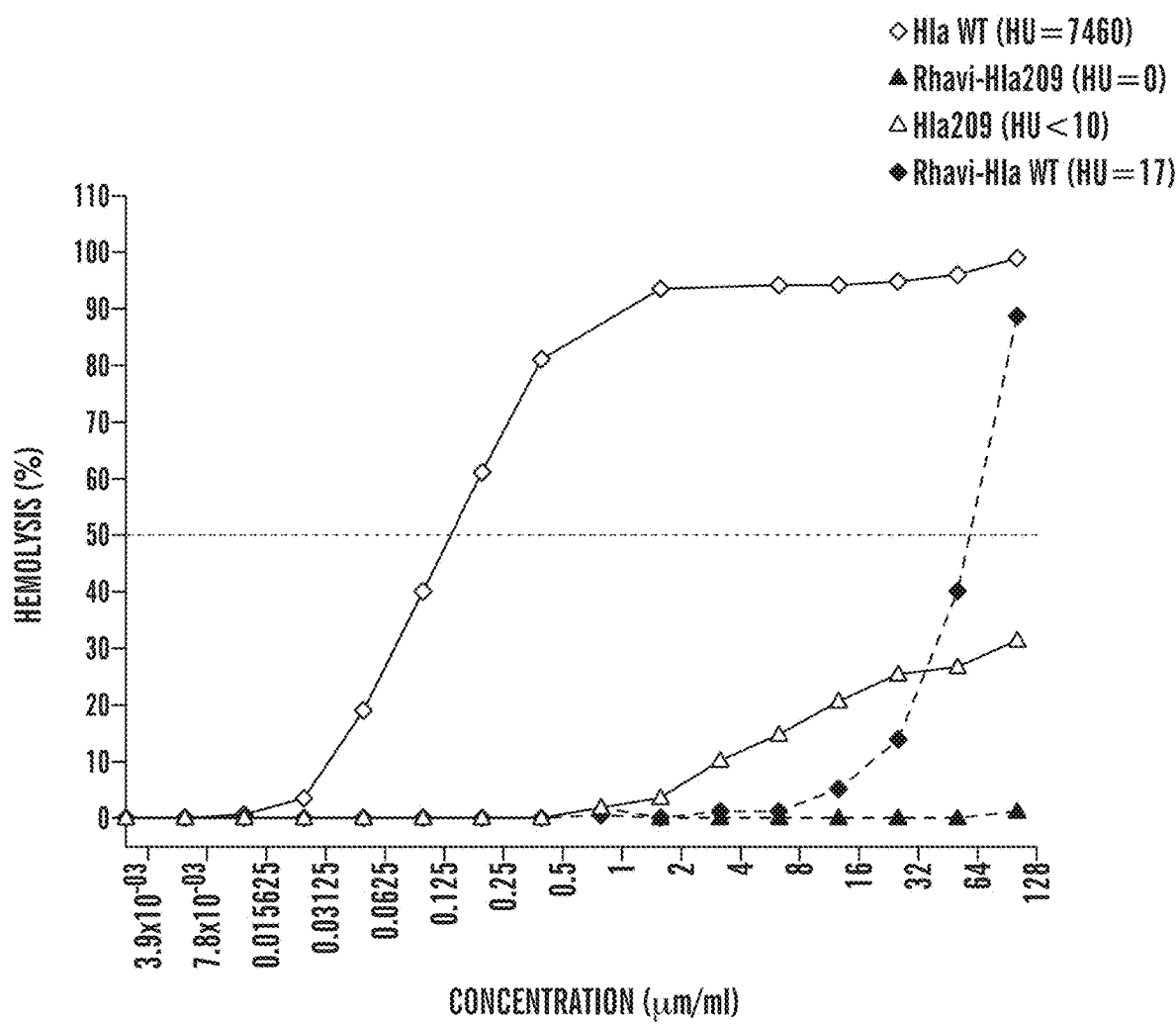
FIG. 12 is a line graph showing hemolytic activity of wild-type Hla, non-hemoytic variants of Hla, and biotin-binding fusion proteins of wild-type Hla and non-hemoytic variants of thereof.
Figure 13:
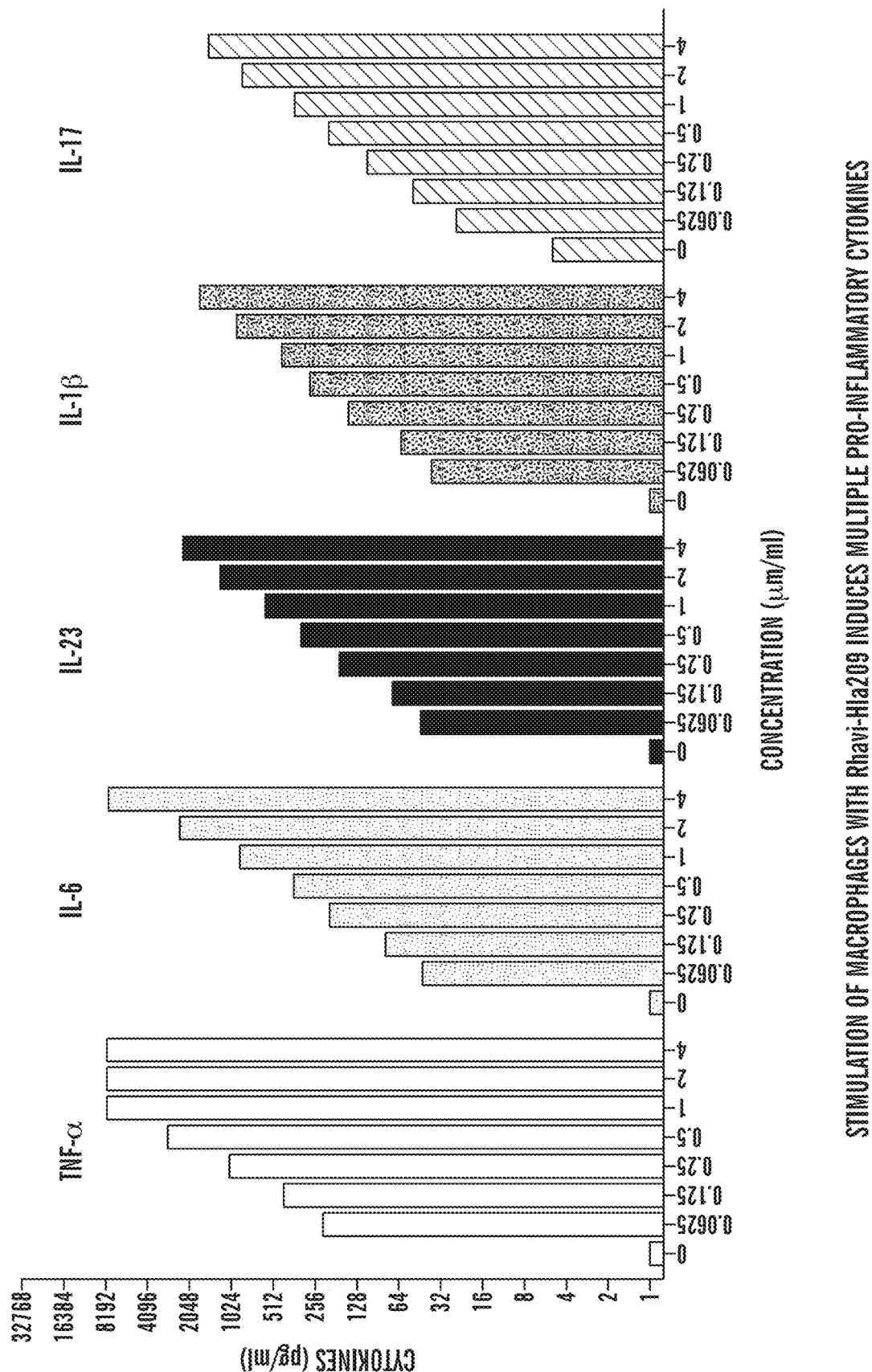
FIG. 13 is a bar graph showing that stimulation of macrophages with biotin-binding fusion protein (rhavi-Hla209) induces multiple pro-inflammatory cytokines.

TLR2 activity of lipidated biotin-binding-protein was determined. Results showed that lipidated biotin-binding protein induced production of IL-8 from HEK TLR2 but not from HEK 293 cells (FIG. 7).

Example 4: Non-Hemolytic Mutants of Hla and Fusion Proteins

The DNA sequence encoding wild type Hla mature polypeptide (amino acid 27 to 319) was cloned from *Staphylococcus aurues* genome. All non-hemolytic mutants of Hla were generated by site-directed mutagenesis using quickchange. To make Hla-biotin binding fusion proteins, the DNA sequence encoding wild type Hla or mutant Hla was inserted beyond the linker region followed biotin-binding protein gene. All constructs were cloned into PET21b and transformed into *E. coli* for expression as described above.

Non-hemolytic mutants of Hla were produced. The exemplary non-hemolytic variants of Hla are shown schematically in FIG. 8. SDS-PAGE of the purified wild-type or non-hemolytic variants of Hla and fusion protein is shown in FIGS. 9 and 10.

Example 5: Hemolytic Activity of Wild Type Hla, Mutant Hla and Fusion Proteins

The hemolytic activity of wild type Hla, mutant Hla and their fusion proteins with biotin-binding protein was analyzed using rabbit blood cells. Red blood cells from 250 μl of rabbit blood were pelleted, washed with PBS twice and then resuspended in 10 ml of PBS. Wild type Hla, mutant Hla and fusion proteins were diluted with PBS at indicated concentrations and then added into 96 well plate at 100 μl per well. Blood cells were added into 96 well plate containing Hla or fusion proteins at 25 μl per well and then incubated at 37° C. for 30 min. Supernatants were collected after centrifugation at 2000 rpm for 5 min and analyzed by ELISA reader at OD450.

hemolytic activity of wild type Hla, mutant Hla and their fusion proteins was assayed. Results demonstrate that mutant Hla have much lower hemolytic activity relative to wild-type Hla (FIG. 11). Further, the Hla fusion proteins comprising a biotin-binding protein had even lower hemolytic activity relative to the non-fusion mutant Hla protein (FIG. 12).

Example 6: Stimulatory Activity of Mutant Hla Fusion Protein

C57 WT macrophage cells were stimulated with non-hemolytic Hla mutant fusion protein. Cells were seeded in 24 well plate at $5\times10^5$ cells per well. Mutant Hla fusion protein was diluted with growth medium and added into wells at indicated concentration for stimulation at 37° C. overnight. Supernatants were collected the second day after centrifugation at 2000 rpm for 5 min and then analyzed for cytokine secretion by ELISA.

Stimulatory activity of mutant Hla fusion protein was analyzed. Results showed that mutant Hla fusion protein (rhavi-Hla209) induced production of multiple pro-inflammatory cytokines, including TNF-α, IL-6, 11-23, IL-1β, and IL-17 (FIG. 13).

Example 7. Lipidated Biotin-Binding Proteins and Mutant Hla Fusion Proteins Facilitate the Immune Response to Other Antigens MAPS based vaccine constructs were made from biotinylated serotype-1 pneumococcal capsular polysaccharide, rhizavidin fused TB antigens and either one from non-lipidated rhizavidin, lipidated rhizavidin or rhavi-Hla209. Mice were immunized with different MAPS constructs and the T cell responses against TB antigens in different immunization groups were analyzed and compared after 3 immunizations. Briefly, the whole blood from different mice groups were stimulated with purified TB proteins in vitro at 37° C. for 6 days and the cytokine concentration in the supernatant was detected by ELISA.

The results showed that the mice groups received MAPS complex containing lipidated rhizavidin or containing rhavi-Hla209 generated better Th17 (IL-17A) and Th1 cell (IFN-γ) responses to the TB antigens (FIG. 14). This indicated that lipidated rhizavidin and rhavi-Hla209 can act as a co-stimulator/adjuvant in MAPS vaccine formulation.

It is understood that the foregoing detailed description and examples are illustrative only and are not to be taken as limitations upon the scope of the invention. Various changes and modifications to the disclosed embodiments, which will be apparent to those of skill in the art, may be made without departing from the spirit and scope of the present invention. Further, all patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

Further, to the extent not already indicated, it will be understood by those of ordinary skill in the art that any one of the various embodiments herein described and illustrated can be further modified to incorporate features shown in any of the other embodiments disclosed herein.

We claim:

1. A polynucleotide encoding a fusion protein comprising a biotin-binding protein fused to an antigenic protein or a peptide, wherein the biotin-binding protein comprises an amino acid sequence having at least 90% sequence identity to SEQ ID NO: 1.

2. The polynucleotide of claim 1, wherein the antigenic protein or peptide is fused to the biotin-binding protein by a peptide linker.

3. The polynucleotide of claim 1, wherein the antigenic protein or peptide is selected from the group consisting of: pneumococcal antigens, tuberculosis antigens, anthrax antigens, HIV antigens, seasonal or epidemic influenza antigens, *Pertussis* antigens, *Staphylococcus aureus* antigens, *Meningococcal* antigens, *Haemophilus* antigens, HPV antigens, *E. coli* antigens, *Salmonella* antigens, *Enterobacter* antigens, *Acinetobacter* antigens, *Pseudomonas* antigens, *Klebsiella* antigens, *Citrobacter* antigens, *Serratia* antigens, *Clostridia* antigens, *Shigella* antigens, *Campylobacter* antigens, *Vibrio cholera* antigens, enteric or non-enteric Gram-negative bacterial antigens, toxoids, toxins, toxin portions, and combinations thereof.

4. The polynucleotide of claim 1, wherein the fusion protein comprises a bacterial signal sequence at the N-terminus.

5. A method of producing a fusion protein, comprising expressing in a host cell the polynucleotide of claim 1.

6. The polynucleotide of claim 2, wherein the peptide linker comprises the amino acid sequence of SEQ ID NO: 22.

7. The polynucleotide of claim 1, wherein the antigenic protein or peptide is a non-hemolytic *S. aureus* alpha-hemolysin.

8. The polynucleotide of claim 7, wherein the non-hemolytic *S. aureus* alpha hemolysin comprises a mutation at amino acid residue 205, 213, or 209-211 of wild-type *S. aureus* alpha-hemolysin.

9. The polynucleotide of claim 7, wherein the non-hemolytic *S. aureus* alpha-hemolysin comprises one of the following mutations in wild-type *S. aureus* alpha-hemolysin: (i) residue 205 W to A; (ii) residue 213 W to A; or (iii) residues 209-211 DRD to AAA.

10. The polynucleotide of claim 7, wherein the non-hemolytic *S. aureus* alpha-hemolysin comprises the amino acid sequence selected from the group consisting of SEQ ID NO: 23, SEQ ID NO: 24, and SEQ ID NO: 25.

11. The polynucleotide of claim 1, comprising the amino acid sequence of SEQ ID NO: 15.

12. The polynucleotide of claim 1, wherein the fusion protein comprises the amino acid sequence selected from the group consisting of: SEQ ID NO: 26, SEQ ID NO: 27, and SEQ ID NO: 28.

13. The polynucleotide of claim 7, wherein the fusion protein has lower hemolytic activity than an equivalent titer of wild-type alpha-hemolysin (Hla).

14. The polynucleotide of claim 1, wherein the antigenic protein or peptide consists of amino acids 27-319 of wild-type alpha-hemolysin of *S. aureus*.

* * * * *